United States Patent
Von Nussbaum et al.

(10) Patent No.: US 9,359,362 B2
(45) Date of Patent: Jun. 7, 2016

(54) TRIAZOLO AND TETRAZOLO PYRIMIDINE DERIVATIVES AS HNE INHIBITORS FOR TREATING COPD

(71) Applicant: BAYER INTELLECTUAL PROPERTY GmbH, Monheim (DE)

(72) Inventors: Franz Von Nussbaum, Düsseldorf (DE); Dagmar Karthaus, Solingen (DE); Sonja Anlauf, Wermelskirchen (DE); Martina Delbeck, Essen (DE); Volkhart Min-Jian Li, Velbert (DE); Daniel Meibom, Leverkusen (DE); Klemens Lustig, Wuppertal (DE)

(73) Assignee: Bayer Intellectual Property Gmbh, Monheim (DE)

( * ) Notice: Subject to any disclaimer, the term of this patent is extended or adjusted under 35 U.S.C. 154(b) by 0 days.

(21) Appl. No.: 14/047,458

(22) Filed: Oct. 7, 2013

(65) Prior Publication Data

US 2014/0038988 A1    Feb. 6, 2014

Related U.S. Application Data

(62) Division of application No. 13/143,323, filed as application No. PCT/EP2009/009296 on Dec. 29, 2009, now Pat. No. 8,569,314.

(30) Foreign Application Priority Data

Jan. 9, 2009 (DE) .......................... 10 2009 004 197

(51) Int. Cl.
| | | |
|---|---|---|
| *A01N 43/90* | (2006.01) | |
| *A61K 31/519* | (2006.01) | |
| *C07D 487/00* | (2006.01) | |
| *C07D 487/04* | (2006.01) | |
| *A61K 45/06* | (2006.01) | |
| *C07D 487/14* | (2006.01) | |

(52) U.S. Cl.
CPC ............ *C07D 487/04* (2013.01); *A61K 31/519* (2013.01); *A61K 45/06* (2013.01); *C07D 487/14* (2013.01)

(58) Field of Classification Search
None
See application file for complete search history.

(56) References Cited

U.S. PATENT DOCUMENTS

| | | | |
|---|---|---|---|
| 7,566,723 B2 | 7/2009 | Gielen-Haertwig et al. | |
| 7,687,510 B2 | 3/2010 | Gielen-Haertwig et al. | |
| 7,893,073 B2 | 2/2011 | Gielen-Haertwig et al. | |
| 8,569,314 B2 * | 10/2013 | Von Nussbaum et al. ........................ | 514/259.31 |
| 2008/0064704 A1 | 3/2008 | Gielen-Haertwig et al. | |
| 2010/0010024 A1 | 1/2010 | Von Nussbaum et al. | |

FOREIGN PATENT DOCUMENTS

| | | |
|---|---|---|
| CA | 2656307 A1 | 1/2008 |
| WO | 0140231 A1 | 6/2001 |
| WO | 2004024700 A1 | 3/2004 |
| WO | 2004024701 A1 | 3/2004 |
| WO | 2005082863 A2 | 9/2005 |
| WO | 2005082864 A1 | 9/2005 |
| WO | 2007129060 A1 | 11/2007 |
| WO | 2008135537 A1 | 11/2008 |

OTHER PUBLICATIONS

Stockley et al., Am. J. Respir. Crit. Care Med., 1999, vol. 160, S49-S52.
Liou et al., Biochemistry 1995, vol. 34, No. 49, 16171-16177.
Stockley et al., Am. J. Respir. Crit. Care Med. 1999, vol. 160, 49-52.
Humbert et al., J. Am. Coll. Cardiol. 2004, vol. 43, 13S-24S.
D'Alonzo et al., Ann. Intern. Med. 1991, vol. 115, 343-349.
Ghofrani et al., Herz 2005, vol. 30, 296-302.
Rosenzweig, Expert Opin. Emerging Drugs 2006, vol. 11, 609-619.
Ito et al., Curr. Med. Chem. 2007, vol. 14, 719-733.
Rabinovitch et al., Lab. Invest. 1986, vol. 55, 632-653.
Todorovich-Hunter et al., Am. Rev. Respir. Dis. 1992, vol. 146, 213-223.
Rabinovitch et al., Am. J. Physiol. 1999, vol. 277, L5-L12.
Zaidi et al., Circulation 2002, vol. 105, 516-521.
Cowan et al., Nature Med. 2000, vol. 6, 698-702.
Simonneau et al., J. Am. Coll. Cardiol. 2004, vol. 43, 5S-12S.
Barnes et al., N. Engl. J. Med. 2000, vol. 343, 269-280.
Gadek et al., J. Clin. Invest. 1981, vol. 68, 889-898.
Werb et al., J. Invest. Dermatol. 1982, vol. 79, 154-159.
Janoff et al., Am. Rev. Respir. Dis. 1985, vol. 132, 417-433.
Liou et al., Biochemistry 1995, vol. 34, Nr. 49, 16171-16177.
Schaaf et al., Respiration 2000, vol. 67, 52-59.
Elssner et al., Transpl. Infect. Dis. 2001, vol. 3, 168-176.
Luhr et al., Am. J. Respir. Crit. Care Med. 1999, vol. 159, 1849-1861.
Chollet-Martin et al., Am. J. Respir. Crit. Care Med. 1996, 154, 594-601.

* cited by examiner

*Primary Examiner* — Jeffrey H Murray
(74) *Attorney, Agent, or Firm* — Aseem V. Mehta

(57) ABSTRACT

The present invention relates to novel heterocyclically fused diaryldihydropyrimidine derivatives, to processes for their preparation, to their use alone or in combination for the treatment and/or prevention of diseases and also to their use for preparing medicaments for the treatment and/or prevention of diseases, in particular for the treatment and/or prevention of disorders of the lung and the cardiovascular system.

12 Claims, No Drawings

TRIAZOLO AND TETRAZOLO PYRIMIDINE DERIVATIVES AS HNE INHIBITORS FOR TREATING COPD

The present invention relates to novel heterocyclically fused diaryldihydropyrimidine derivatives, to processes for their preparation, to their use alone or in combination for the treatment and/or prevention of diseases and also to their use for preparing medicaments for the treatment and/or prevention of diseases, in particular for the treatment and/or prevention of disorders of the lung and the cardiovascular system.

Human leukocyte elastase (HLE, EC 3.4.21.37), also called human neutrophil elastase (HNE, hNE), belongs to the family of the serine proteases. The proteolytic enzyme is found in the azurophilic granules of polymorphonuclear leukocytes (PMN leukocytes). Intracellular elastase performs an important function in defense against pathogens by breaking down the foreign particles taken by phagocytosis. Activated neutrophilic cells release the HNE from the granules into the extracellular space (extracellular HNE), with some of the released HNE remaining on the outside of the neutrophilic cell membrane (membrane-associated HNE). The highly active enzyme is able to break down a large number of connective tissue proteins, for example the proteins elastin, collagen and fibronectin. Elastin occurs in high concentrations in all tissue types showing high elasticity, for example in the lung and the arteries. HNE is involved in the tissue breakdown and transformation (tissue remodeling) associated with a large number of pathological processes (for example tissue injuries). HNE is also an important modulator of inflammatory processes. HNE induces for example increased interleukin-8 (IL-8) gene expression.

Accordingly, it is presumed that HNE plays an important role in many disorders, injuries and pathological changes whose formation and/or progression are/is associated with inflammatory events and/or proliferative and hypertrophic tissue and vessel transformation. This can be in particular disorders and/or injuries of the lung or the cardiovascular system, or it may be sepsis, cancerous disorders or other inflammatory disorders.

Disorders and injuries of the lung which may be mentioned in this context are in particular chronic obstructive pulmonary disease (COPD), acute respiratory distress syndrome (ARDS), cystic fibrosis (CF; also referred to as mucoviscidosis), lung emphysema and acute lung injury (ALI). Disorders and injuries of the cardiovascular system where HNE is involved are, for example, tissue transformations during heart failure and reperfusion damage after acute myocardial infarction (AMI), cardiogenic shock, acute coronary syndrome (ACS), and also aneurysms. Disorders associated with sepsis are, for example, systemic inflammatory response syndrome (SIRS), severe sepsis, septic shock and multi-organ failure (MOF; multi-organ dysfunction, MODS) and also disseminated intravascular coagulation (DIC). Examples of tissue breakdown and transformation in cancerous processes are the migration of cancer cells into healthy tissue (formation of metastases) and the formation of new supply blood vessels (neo-angiogenesis). Other inflammatory diseases where HNE plays a role are rheumatoid disorders, for example rheumatoid arthritis, inflammatory bowel disease (IBD), Crohn's disease (CD) and arteriosclerosis.

It is generally assumed that elastase-mediated pathological processes are based on a displaed equilibrium between free elastase and endogenous elastase inhibitor protein (mainly alpha-1 antitrypsin, AAT) [*Neutrophils and protease/antiprotease imbalance*, Stockley, Am. J. Respir. Crit. Care Med. 160, 49-52 (1999)]. AAT is present in large excess in the plasma and thus very rapidly neutralizes free HNE. The concentration of free elastase is elevated in various pathological processes, so that there is a local shift in the balance between protease and protease inhibitor in favor of the protease. In addition, membrane-associated elastase of the activated PMN cells is very substantially protected from inhibition by AAT. The same applies to free elastase, which is located in a microcompartment which is difficult to access between the neutrophilic cell and the adjoining tissue cell (for example endothelial cell). In addition, strong oxidizing conditions prevail in the vicinity of activated leukocytes (oxidative burst), and thus AAT is oxidized and loses several orders of magnitude in the inhibitory effect.

Novel elastase-inhibiting active compounds (exogenously administered inhibitors of HNE) ought accordingly to have a low molecular weight in order to be able also to reach and inhibit the membrane-associated HNE and the HNE present in the protected microcompartment (see above). Also necessary for this purpose is good in vivo stability of the substances (low in vivo clearance). In addition, these compounds ought to be stable under oxidative conditions in order not to lose inhibitory power in the pathological process.

Pulmonary arterial hypertension (PAH) is a progressive lung disorder which, untreated, leads to death on average within 2.8 years after being diagnosed. An increasing constriction of the pulmonary circulation leads to increased stress on the right heart, which may develop into right heart failure. By definition, the mean pulmonary aterial pressure (mPAP) in case of chronic pulmonary hypertension is >25 mmHg at rest or >30 mmHg during exertion (normal value <20 mmHg). The pathophysiology of pulmonary arterial hypertension is characterized by vasoconstriction and remodeling of the pulmonary vessels. In chronic PAH there is neomuscularization of initially unmuscularized pulmonary vessels, and the vascular muscles of the already muscularized vessels increase in circumference. This increasing obliteration of the pulmonary circulation results in progressive stress on the right heart, which leads to a reduced output from the right heart and eventually ends in right heart failure (M. Humbert et al., *J. Am. Coll. Cardiol.* 2004, 43, 13S-24S). PAH is an extremely rare disorder, with a prevalence of 1-2 per million. The average age of the patients has been estimated to be 36 years, and only 10% of the patients were over 60 years of age. Distinctly more women than men are affected (G. E. D'Alonzo et al., *Ann. Intern. Med.* 1991, 115, 343-349).

Despite all the advances in the therapy of pulmonary arterial hypertension there is as yet no prospect of cure of this serious disorder. Standard therapies available on the market (for example prostacyclin analogs, endothelin receptor antagonists, phosphodiesterase inhibitors) are able to improve the quality of life, the exercise tolerance and the prognosis of the patients. The principles of these therapies are primarily hemodynamic, influencing vessel tone but having no direct influence on the pathogenic remodeling processes. In addition, the possibility of using these medicaments is restricted through the sometimes serious side effects and/or complicated types of administration. The period over which the clinical situation of the patients can be improved or stabilized by specific monotherapy is limited (for example owing to the development of tolerance). Eventually the therapy escalates and thus a combination therapy is applied, where a plurality of medicaments must be given concurrently.

Novel combination therapies are one of the most promising future therapeutic options for the treatment of pulmonary arterial hypertension. In this connection, the finding of novel pharmacological mechanisms for the treatment of PAH is of particular interest (Ghofrani et al., *Herz* 2005, 30, 296-302; E.

B. Rosenzweig, *Expert Opin. Emerging Drugs* 2006, 11, 609-619; T. Ito et al., *Curr. Med. Chem.* 2007, 14, 719-733). Therapeutic options which intervene directly in the remodeling event (antiremodeling mechanisms reverse remodeling mechanisms) in particular might form the basis for a more causal treatment and thus be of great advantage for the patients. In this connection, it will be possible to combine known and novel therapies. In order to minimize the risk of interfering medicament-medicament interactions in such a combination therapy, these novel active compounds ought to inhibit metabolizing P450 CYP enzymes only to a very small extent or not at all.

These days, one proceeds on the assumption that elastase plays a central role in pathological remodeling. It has been possible to find a fragmentation of connective tissue (internal elastic lamina) in animal models and in patients with elevated pulmonary arterial blood pressure (pulmonary arterial hypertension) [Rabinovitch et al., *Lab. Invest.* 55, 632-653 (1986)], and it was possible to show in animal models of pulmonary arterial hypertension (hypoxic rat and mouse model, monocrotaline rat model) that elastase activity was increased and was associated with the fragmentation of connective tissue [Todorovich-Hunter et al., *Am. Rev. Respir. Dis.* 146, 213-223 (1992)]. It is suspected that the tissue remodeling to be observed during the disease process of pulmonary arterial hypertension is induced by an elastase-mediated release of connective tissue-associated growth factors, for example of basic fibroblast growth factor (bFGF) [Rabinovitch, *Am. J. Physiol.* 277, L5-L12 (1999)]. It was possible to show a positive effect with an overexpressed elastase inhibitor protein in the hypoxic mouse model of pulmonary arterial hypertension [Zaidi et al., *Circulation* 105, 516-521 (2002)]. It was possible to show a positive effect with synthetic low-molecular-weight elastase inhibitors in the monocrotaline rat model of pulmonary arterial hypertension; in this case a beneficial effect on tissue remodeling was also to be noted [Cowan et al., *Nature Med.* 6, 698-702 (2000)]. However, all previously disclosed low-molecular-weight elastase inhibitors have low selectivity, are chemically reactive and/or have only limited oral availability, thus to date thwarting clinical development of an oral elastase inhibitor for these indications.

The term "pulmonary arterial hypertension" includes particular types of pulmonary hypertension as have been specified for example by the World Health Organization (WHO) (*Clinical Classification of Pulmonary Hypertension*, Venice 2003; G. Simonneau et al., *J. Am. Coll. Cardiol.* 2004, 43, 5S-12S).

According to this classification, pulmonary arterial hypertension includes idiopathic pulmonary arterial hypertension (IPAH, formerly also called primary pulmonary hypertension, PPH), familial pulmonary arterial hypertension (FPAH), persistent pulmonary hypertension in neonates and also associated pulmonary arterial hypertension (APAH) which is associated with collagenoses, congenital systemic-pulmonary shunt vitiae, portal hypertension, HIV infections, intake of particular drugs and medicaments (for example anorectics), with disorders having a significant venous/capillary involvement, such as pulmonary venal-occlusive disease and pulmonary capillary hemangiomatosis, or with other disorders such as thyroid disorders, glycogen storage diseases, Gaucher's disease, hereditary teleangiectasia, hemoglobinopathies, myeloproliferative disorders and splenectomy.

Other types of pulmonary hypertension include, for example, the pulmonary hypertension associated with left heart disorders, for example with ventricular or valvular disorders, the pulmonary hypertension associated with disorders of the respiratory tract and/or of the lungs, for example with chronic obstructive lung disease, interstitial lung disease or pulmonary fibrosis, the pulmonary hypertension attributable to chronic thrombotic and/or embolic disorders, for example associated with thromboembolic obstruction of pulmonary arteries, and the pulmonary hypertension caused by generally inflammatory disease processes or by special causes (for example associated with schistosomiasis, sarcoidosis and neoplastic diseases).

Chronic obstructive pulmonary disease (COPD) is a pulmonary disease which progresses slowly and is characterized by obstruction of breathing caused by pulmonary emphysema and/or chronic bronchitis. First symptoms of the disorder generally appear from the fourth to the fifth decade of life onwards. In the years that follow, the short breath frequently worsens and a cough, associated with extensive and sometimes prolonged discharge and obstructed breathing up to breathlessness (dyspnea), manifests itself. COPD is primarily a smoker's disease: smoking is responsible for 90% of all cases of COPD and 80-90% of all deaths caused by COPD. COPD is a major medical problem and represents the sixth most frequent cause of death world-wide. About 4-6% of people over the age of 45 are affected.

Although the obstruction of breathing may only be partial and temporal, COPD cannot be cured. Accordingly, the target of the treatment is to improve the quality of life, to ameliorate the symptoms, to prevent acute worsening and to slow the progressive impairment of pulmonary function. Existing pharmacotherapies, which have hardly changed over the last two to three decades, are the use of bronchodilators to open up blocked respiratory paths, and in certain situations corticosteroids to control the inflammation of the lung [P. J. Barnes, *N. Engl. J. Med.* 343, 269-280 (2000)]. The chronic inflammation of the lung, caused by cigarette smoke or other irritants, is the force behind the development of the disease. The mechanism on which it is based involves immune cells which, during the course of the inflammatory reaction of the lung, secrete various chemokines. This attracts neutrophilic cells and subsequently alveolar macrophages to the connective tissue of the lung and the lumen. Neutrophilic cells secrete a protease cocktail which contains mainly HNE and protease 3. This causes the local protease/antiprotease balance to shift in favor of the proteases, resulting inter alia in an unchecked elastase activity and as a consequence thereof an excess degradation of the elastins of the alveolar cells [J. E. Gadek et al., *J. Clin. Invest.* 68, 889-898 (1981); Z. Werb et al., *J. Invest. Dermatol.* 79, 154-159 (1982); A. Janoff, *Am. Rev. Respir. Dis.* 132, 417-433 (1985); P. J. Barnes, *N. Engl. J. Med.* 343, 269-280 (2000)]. This tissue degradation causes the bronchii to collapse. This is associated with a reduced elasticity of the lung, which leads to obstructed breathing and impaired respiration. In addition, frequent and persistent inflammation of the lung may lead to remodeling of the bronchii and as a consequence to the formation of lesions. Such lesions contribute to chronic cough, which characterizes chronic bronchitis.

Alpha-1 antitrypsin (AAT) is a small endogenous protein and represents, as mentioned above, the most important endogenous elastase inhibitor. In patients having a genetic deficiency of this protein (AATD), the protease/antiprotease balance is shifted. Accordingly, in AADT patients, the effective radius and the duration of action of HNE is increased by a factor of 2.5 and 6.5, respectively [T. G. Liou and E. J. Campbell, *Biochemistry* 1995, 16171-16177]. AADT patients have an increased risk of developing pulmonary emphysema or COPD, and in many AADT patients a lung transplant is indicated.

Bronchiectasis is understood as an abnormal dilation of the bronchial tree. Two forms may be distinguished: sack-shaped localized bronchiectases and generalized, cylindrical bronchiectases. Bronchiectases may be congenital; however, in most cases they are acquired and are found in particular in smokers. Owing to the dilation, drainage of the bronchial secretions is rendered more difficult, and the retained bronchial secretions promote infections. Frequently, bronchiectases are also encountered in the case of congenital disorders of the mucosa such as mucoviscidosis with abnormal viscosity of the bronchial secretions and in the case of ciliary dyskinesia syndrome. In the case of this syndrome (Kartagener syndrome), the architecture and function of the cilia and thus drainage of the secretions are impaired. Other causes of bronchiectases may be obstructions proximal to the ectasis, for example by tumours or foreign bodies. Recurrent and persisting infections weakening the bronchial walls are also thought to be causal. Furthermore, there are bronchiectasias which can not be connected unambiguously to states of infection or exogenic noxa (idiopathic bronchiectasias).

Bronchiectasia is characterized by migration of neutrophils into the pulmonary tissue. The patients show a marked imbalance between neutrophilic activity and protective inhibitor proteins, resulting in damage to the pulmonary tissue by the proteases (mainly HNE) secreted by the neutrophils [Schaaf et al., *Respiration* 67, 52-59 (2000)].

Bronchiolitis obliterans is an inflammation of the bronchioli with destruction of the epithelium and formation of a fibrin-rich exudate in the bronchioli and the neighbouring alveoli. Organization of the exudate results in plugs of connective tissue reaching from the bronchioli into the alveoli. The disease is characterized by an increased number of neutrophils in the respiratory tract and an imbalance between free elastase and the endogenous elastase inhibitor protein [Elssner et al., *Transpl. Infect. Dis.* 3, 168-176 (2001)] Prior infections and medicaments are being discussed as possible causes. The disease may also occur in the context of a transplant rejection.

Acute lung injury (ALI) and the more pronounced form thereof, acute respiratory distress syndrome (ARDS), are serious disorders associated with a mortality of 50-60%. According to the definition of the North American-European Consensus Conference (NAECC) of 1994, ALI and ARDS are defined by an acute onset, bilateral radiologically visible infiltrates, a $PaO_2/FiO_2$ index of ≤300 mmHg (ALI) or ≤200 mmHg (ARDS), a pulmonary capillary wedge pressure of <18 mmHg and no clinical evidence of left atrial hypertension.

The development of acute lung injury may be preceded both by pulmonary and extrapulmonary disorders. Aspiration of stomach content, pneumonias, smoke poisoning, pulmonary contusion and near-drowning are considered to be lung-specific predisposing factors. In particular the aspiration of stomach content and pneumonias are frequently seen as initial disorders of ALI/ARDS of pulmonary origin. The most frequent indirect events are polytrauma, sepsis, repeated blood transfusions, acute pancreatitis and burns. The incidence is 17.9 cases of ALI and 13.5 cases of ARDS per 100 000 inhabitants and year [Luhr et al., *Am. J. Respir. Crit. Care Med.* 159, 1849-1861 (1999)].

A central role in the development of these disorders is played by the massive inflammatory changes in the lung, which are triggered by a widely branched system of mediators. An important role in the development of lung injury is also played by neutrophilic granulocytes, the number of which increases permanently during the inflammatory process [Chollet-Martin et al., *Am. J. Respir. Crit. Care Med.* 154, 594-601 (1996)]. The action of the mediators causes damage to the alveolocapillary membranes, and this results in an increased permeability of the alveolar capillary barrier. Owing to the increased permeability, protein-rich fluid can permeate into the alveolae and also into the interstitial space; a low-pressure pulmonary edema develops. Characteristic for ALI/ARDS, this is a noncardiogenic edema. The edema fluid contains mainly fibrin, erythrocytes, leukocytes, hyaline membranes and other proteins. Together with the products of activated neutrophils, the protein-rich exudate leads to dysfunction of the surfactant. The inflammatory processes cause damage and loss of pneumocytes of type II, which form surfactant, resulting in a reduced surfactant production. The surfactant deficit increases the surface tension in the alveolae; the alveolae collapse and atelectases are formed. With perfusion being maintained, there is thus a ventilation/perfusion imbalance resulting in an increase of the pulmonary right-left shunt. Furthermore, compliance is reduced, and in contrast the alveolar dead space is increased because there are areas which are ventilated but, owing to pulmonary hypertension, no longer sufficiently perfused.

An increased elastase activity, which correlates to the severity of the lung injury, could be measured in the bronchoalveolar lavage fluid (BALF) of ARDS patients. In animal models where the lung is injured (for example by administration of LPS), this effect can be reproduced. Here, treatment with elastase inhibitors (for example sivelestat or elafin, vide infra,) reduces the elastase activity in the BALF considerably and improves lung function.

In Japan and South Korea, an elastase inhibitor (sivelestat, Elaspol®) is approved for the treatment of acute lung injury associated with SIRS. The reversible, but reactive compound has only a relatively weak effect on HNE ($K_i$ 200 nM) and also acts on the pancreas elastase ($IC_{50}$ 5.6 μM). The active compound is administered intravenously, oral administration is not possible.

Elafin and structural analogs are also investigated as therapeutically useful elastase inhibitors. Elafin is an endogenous small protein which inhibits both elastase and proteinase 3. However, owing to the proteinergic character, oral administration of elafin is not possible.

It is an object of the present invention to provide novel substances acting as low-molecular-weight, non-reactive and selective inhibitors of human neutrophil elastase (HNE), which are suitable as such for the treatment and/or prevention in particular of pulmonary disorders and disorders of the cardiovascular system.

WO 2004/024700, WO 2004/024701, WO 2005/082863, WO 2005/082864 and WO 2008/003412 disclose various 1,4-diaryldihydropyrimidin-2-one derivatives as HNE inhibitors for the treatment of chronic obstructive pulmonary disease, acute coronary syndrome, myocardial infarction, heart failure and pulmonary hypertension. WO 2007/129060 and WO 2008/135537 claim tetrahydropyrrolopyrimidinediones as HNE inhibitors. WO 01/40231 describes heterocyclically fused dihydropyrimidines as potassium channel inhibitors for the treatment of atrial arrhythmias.

The present invention provides compounds of the general formula (I)

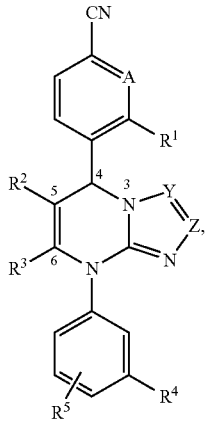

(I)

in which
A represents C—R$^6$ or N in which
  R$^6$ represents hydrogen, fluorine or chlorine,
Y represents C—R$^7$ or N in which
  R$^7$ represents hydrogen, (C$_1$-C$_6$)-alkyl, amino or a group of the formula —NH—C(=O)—R$^8$ or —NH—SO$_2$—R$^8$ in which
    R$^8$ represents (C$_1$-C$_6$)-alkyl, (C$_3$-C$_6$)-cycloalkyl or phenyl,
      where (C$_1$-C$_6$)-alkyl may be substituted by hydroxyl, (C$_1$-C$_4$)-alkoxy, (C$_3$-C$_6$)-cycloalkyl or phenyl and up to three times by fluorine
      and where
        the cycloalkyl groups mentioned may be substituted up to two times by identical or different substituents from the group consisting of (C$_1$-C$_4$)-alkyl and up to two times by fluorine
      and
        the phenyl groups mentioned may be substituted up to two times by identical or different substituents from the group consisting of fluorine, chlorine, cyano, (C$_1$-C$_4$)-alkyl, difluoromethyl, trifluoromethyl, (C$_1$-C$_4$)-alkoxy, difluoromethoxy and trifluoromethoxy,
Z represents C—R$^9$ or N in which
  R$^9$ represents hydrogen, (C$_1$-C$_6$)-alkyl, (C$_1$-C$_6$)-alkoxy, (C$_1$-C$_6$)-alkoxycarbonyl, (C$_3$-C$_6$)-cycloalkyl, phenyl or 5- or 6-membered heteroaryl,
    where (C$_1$-C$_6$)-alkyl may be substituted by hydroxyl, (C$_1$-C$_4$)-alkoxy, (C$_3$-C$_6$)-cycloalkyl or phenyl and up to three times by fluorine
    and where
      the cycloalkyl groups mentioned may be substituted up to two times by identical or different substituents from the group consisting of (C$_1$-C$_4$)-alkyl and up to two times by fluorine
    and
      the phenyl and heteroaryl groups mentioned may be substituted up to two times by identical or different substituents from the group consisting of fluorine, chlorine, cyano, (C$_1$-C$_4$)-alkyl, difluoromethyl, trifluoromethyl, (C$_1$-C$_4$)-alkoxy, difluoromethoxy and trifluoromethoxy,
or
R$^9$ represents a group of the formula —SO$_2$—NR$^{10}$R$^{11}$ or —NR$^{12}$R$^{13}$ in which
  R$^{10}$ and R$^{11}$ are identical or different and independently of one another represent hydrogen, (C$_1$-C$_6$)-alkyl, (C$_3$-C$_6$)-cycloalkyl, phenyl or 5- or 6-membered heteroaryl,
  R$^{12}$ represents hydrogen, (C$_1$-C$_6$)-alkyl, (C$_3$-C$_6$)-cycloalkyl, phenyl or (C$_1$-C$_6$)-alkylsulfonyl,
    where (C$_1$-C$_6$)-alkyl may be substituted by cyano, hydroxyl, (C$_1$-C$_4$)-alkoxy, hydroxycarbonyl, (C$_1$-C$_4$)-alkoxycarbonyl, aminocarbonyl, mono-(C$_1$-C$_4$)-alkylaminocarbonyl, di-(C$_1$-C$_4$)-alkylaminocarbonyl, (C$_3$-C$_6$)-cycloalkyl or phenyl and up to three times by fluorine
    and where
      the cycloalkyl groups mentioned may be substituted up to two times by identical or different substituents from the group consisting of (C$_1$-C$_4$)-alkyl and up to two times by fluorine
    and
      the phenyl groups mentioned may be substituted up to two times by identical or different substituents from the group consisting of fluorine, chlorine, cyano, (C$_1$-C$_4$)-alkyl, difluoromethyl, trifluoromethyl, (C$_1$-C$_4$)-alkoxy, difluoromethoxy and trifluoromethoxy,
  R$^{13}$ represents hydrogen, (C$_1$-C$_6$)-alkyl or a group of the formula —C(=O)—R$^{14}$, —C(=O)—O—R$^{15}$ or —C(=O)—NR$^{16}$R$^{17}$ in which
    R$^{14}$ represents hydrogen, (C$_1$-C$_8$)-alkyl, (C$_3$-C$_6$)-cycloalkyl, 4- to 6-membered heterocyclyl, phenyl or 5- or 6-membered heteroaryl,
      where (C$_1$-C$_8$)-alkyl may be substituted by hydroxyl, (C$_1$-C$_4$)-alkoxy, benzyloxy, phenoxy, (C$_1$-C$_4$)-acyloxy, amino, mono-(C$_1$-C$_4$)-alkylamino, di-(C$_1$-C$_4$)-alkylamino, (C$_1$-C$_4$)-acylamino, (C$_1$-C$_4$)-alkoxycarbonylamino, (C$_3$-C$_6$)-cycloalkyl or phenyl and up to three times by fluorine and up to two CH$_2$ groups in (C$_1$-C$_8$)-alkyl may be exchanged for an oxygen atom provided this results in a stable compound
      and where
        the cycloalkyl and heterocyclyl groups mentioned may be substituted up to two times by identical or different substituents from the group consisting of (C$_1$-C$_4$)-alkyl and up to two times by fluorine
      and
        the phenyl and heteroaryl groups mentioned may be substituted up to two times by identical or different substituents from the group consisting of fluorine, chlorine, cyano, (C$_1$-C$_4$)-alkyl, difluoromethyl, trifluoromethyl, (C$_1$-C$_4$)-alkoxy, difluoromethoxy, trifluoromethoxy and hydroxycarbonyl,
    R$^{15}$ represents (C$_1$-C$_6$)-alkyl which may be substituted by (C$_3$-C$_6$)-cycloalkyl or phenyl,
    R$^{16}$ and R$^{17}$ are identical or different and independently of one another represent hydrogen or (C$_1$-C$_6$)-alkyl which may be substituted by hydroxyl or (C$_1$-C$_4$)-alkoxy,
or
  R$^{12}$ and R$^{13}$ together with the nitrogen atom to which they are attached form a 5- or 6-membered heterocycle which may contain a further ring heteroatom from the group consisting of N, O and S and which may be substituted up to two times by identical or different substituents from the group consisting of $(C_1-C_4)$-alkyl, hydroxyl, $(C_1-C_4)$-alkoxy and oxo and may be fused to a phenyl ring, or in which $R^7$ and $R^9$, if both are present, are attached to one another and together with the carbon atoms to which they are attached form a fused phenyl, pyridyl or pyrimidyl ring which may in each case be substituted up to two times by identical or different substituents from the group consisting of fluorine, chlorine, cyano, $(C_1-C_4)$-alkyl, difluoromethyl, trifluoromethyl, $(C_1-C_4)$-alkoxy, difluoromethoxy and trifluoromethoxy, $R^1$ represents hydrogen, halogen, cyano, nitro, $(C_1-C_6)$-alkyl, difluoromethyl, trifluoromethyl, $(C_1-C_6)$-alkoxy, difluoromethoxy, trifluoromethoxy, amino, mono- or di-$(C_1-C_6)$-alkylamino or represents a group of the formula —NH—C(=O)—$R^{18}$, —NH—C(=O)—NHR$^{18}$, —NH—SO$_2$—$R^{19}$ or —S(O)$_n$—$R^{20}$ in which $R^{18}$ represents hydrogen or $(C_1-C_6)$-alkyl, $R^{19}$ represents $(C_1-C_6)$-alkyl, $R^{20}$ represents $(C_1-C_6)$-alkyl which may be substituted by hydroxyl, $(C_1-C_4)$-alkoxy, amino, mono- or di-$(C_1-C_4)$-alkylamino, hydroxycarbonyl, aminocarbonyl, $(C_3-C_6)$-cycloalkyl or phenyl and up to three times by fluorine, or $(C_2-C_6)$-alkenyl, $(C_3-C_6)$-cycloalkyl or phenyl, where the cycloalkyl groups mentioned may be substituted up to two times by identical or different substituents from the group consisting of $(C_1-C_4)$-alkyl, hydroxyl and $(C_1-C_4)$-alkoxy and the phenyl groups mentioned may be substituted up to two times by identical or different substituents from the group consisting of fluorine, chlorine, cyano, $(C_1-C_4)$-alkyl, difluoromethyl, trifluoromethyl, $(C_1-C_4)$-alkoxy, difluoromethoxy and trifluoromethoxy, and n represents the number 0, 1 or 2, $R^2$ represents cyano or a group of the formula —C(=O)—$R^{21}$, —C(=O)—O—$R^{21}$ or —C(=O)—NH—$R^{21}$ in which $R^{21}$ represents hydrogen, $(C_1-C_6)$-alkyl, $(C_3-C_6)$-alkenyl or $(C_3-C_6)$-cycloalkyl, where $(C_1-C_6)$-alkyl and $(C_3-C_6)$-cycloalkyl for their part may be substituted up to two times by identical or different substituents from the group consisting of hydroxyl, $(C_1-C_4)$-alkoxy, hydroxycarbonyl, $(C_1-C_4)$-alkoxycarbonyl, amino, mono- and di-$(C_1-C_4)$-alkylamino and in $(C_1-C_6)$-alkyl and $(C_3-C_6)$-cycloalkyl in each case one CH$_2$ group may be replaced by an oxygen atom provided this results in a chemically stabile compound, $R^3$ represents methyl or ethyl or $R^2$ and $R^3$ are attached to one another and together form a fused group of the formula

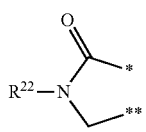

in which

* denotes the point of attachment to the 5-position, marked in formula (I), of the dihydropyrimidine ring and

** denotes the point of attachment to the 6-position, marked in formula (I), of the dihydropyrimidine ring and $R^{22}$ represents hydrogen, $(C_1-C_6)$-alkyl or $(C_3-C_6)$-cycloalkyl, where $(C_1-C_6)$-alkyl may be substituted by hydroxyl, $(C_1-C_4)$-alkoxy, aminocarbonyl, aminocarbonylamino, $(C_1-C_4)$-acylamino or $(C_3-C_6)$-cycloalkyl, $R^4$ represents nitro or trifluoromethyl and $R^5$ represents hydrogen, fluorine or chlorine, and their salts, solvates and solvates of the salts.

Compounds according to the invention are the compounds of the formula (I) and the salts, solvates and solvates of the salts thereof, the compounds of the formulae mentioned hereinafter and encompassed by formula (I) and the salts, solvates and solvates of the salts thereof, and the compounds which are mentioned hereinafter as exemplary embodiments and encompassed by formula (I) and the salts, solvates and solvates of the salts thereof, insofar as the compounds encompassed by formula (I) and mentioned hereinafter are not already salts, solvates and solvates of the salts.

The compounds according to the invention may, depending on their structure, exist in stereoisomeric forms (enantiomers, diastereomers, including those in the case of atropisomers). The present invention therefore relates to the enantiomers and diastereomers and to their respective mixtures. The stereoisomerically pure constituents can be isolated in a known manner from such mixtures of enantiomers and/or diastereomers.

If the compounds according to the invention may occur in tautomeric forms, the present invention encompasses all tautomeric forms.

Salts which are preferred for the purposes of the present invention are physiologically acceptable salts of the compounds according to the invention. Also encompassed are salts which are themselves unsuitable for pharmaceutical uses but can be used for example for isolating or purifying the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases such as, by way of example and preferably, alkali metal salts (for example sodium salts and potassium salts), alkaline earth metal salts (for example calcium salts and magnesium salts) and ammonium salts derived from ammonia or organic amines having 1 to 16 carbon atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refers for the purposes of the invention to those forms of the compounds according to the invention which form, in the solid or liquid state, a complex by coordination with solvent molecules. Hydrates are a specific form of solvates in which the coordination takes place with water. Hydrates are preferred solvates in the context of the present invention.

The present invention additionally encompasses prodrugs of the compounds of the invention. The term "prodrugs" encompasses compounds which themselves may be biologically active or inactive, but are converted during their residence time in the body into compounds according to the invention (for example by metabolism or hydrolysis).

In the context of the present invention, the substituents have the following meaning, unless specified otherwise:

$(C_1-C_8)$-Alkyl, $(C_1-C_6)$-alkyl and $(C_1-C_4)$-alkyl stand for the purposes of the invention for a straight-chain or branched alkyl radical having respectively 1 to 8, 1 to 6 and 1 to 4 carbon atoms. A straight-chain or branched alkyl radical having 1 to 6, particularly preferably 1 to 4, carbon atoms is preferred. Examples which may be preferably mentioned are: methyl, ethyl, n-propyl, isopropyl, n-butyl, isobutyl, sec-butyl, tert-butyl, 1-ethylpropyl, n-pentyl, neopentyl, n-hexyl, n-heptyl and n-octyl.

$(C_2-C_6)$-Alkenyl and $(C_3-C_6)$-alkenyl stand for the purposes of the invention for a straight-chain or branched alkenyl radical having respectively 2 to 6 and 3 to 6 carbon atoms and one or two double bonds. A straight-chain or branched alkenyl radical having 3 to 6 carbon atoms and one double bond is preferred. Examples which may be preferably mentioned are: allyl, isopropenyl, n-but-2-en-1-yl, n-but-3-en-1-yl, n-pent-2-en-1-yl, n-pent-3-en-1-yl, n-pent-4-en-1-yl, 3-methylbut-2-en-1-yl and 4-methylpent-3-en-1-yl.

$(C_1-C_6)$-Alkoxy and $(C_1-C_4)$-alkoxy stand for the purposes of the invention for a straight-chain or branched alkoxy radical having respectively 1 to 6 and 1 to 4 carbon atoms. A straight-chain or branched alkoxy radical having 1 to 4 carbon atoms is preferred. Examples which may be preferably mentioned are: methoxy, ethoxy, n-propoxy, isopropoxy, n-butoxy, tert-butoxy, n-pentoxy and n-hexoxy.

$(C_1-C_6)$-Alkoxycarbonyl and $(C_1-C_4)$-alkoxycarbonyl stand for the purposes of the invention for a straight-chain or branched alkoxy radical which has respectively 1 to 6 and 1 to 4 carbon atoms and is attached via a carbonyl group. A straight-chain or branched alkoxycarbonyl group having 1 to 4 carbon atoms in the alkoxy radical is preferred. Examples which may be preferably mentioned are: methoxycarbonyl, ethoxycarbonyl, n-propoxycarbonyl, isopropoxycarbonyl, n-butoxycarbonyl, tert-butoxycarbonyl, n-pentoxycarbonyl and n-hexoxycarbonyl.

$(C_1-C_4)$-Alkoxycarbonylamino stands for the purposes of the invention for an amino group having a straight-chain or branched alkoxycarbonyl substituent which has 1 to 4 carbon atoms in the alkoxy radical and is attached via the carbonyl group to the nitrogen atom. Examples which may be preferably mentioned are: methoxycarbonylamino, ethoxycarbonylamino, n-propoxycarbonyl-amino, isopropoxycarbonylamino, n-butoxycarbonylamino and tert-butoxycarbonylamino.

$(C_1-C_6)$-Alkylsulfonyl and $(C_1-C_4)$-alkylsulfonyl stand for the purposes of the invention for a straight-chain or branched alkylsulfonyl radical having respectively 1 to 6 and 1 to 4 carbon atoms. A straight-chain or branched alkylsulfonyl radical having 1 to 4 carbon atoms is preferred.

Examples which may be preferably mentioned are: methylsulfonyl, ethylsulfonyl, n-propyl-sulfonyl, isopropylsulfonyl, n-butylsulfonyl, tert-butylsulfonyl, n-pentylsulfonyl and n-hexylsulfonyl.

Mono-$(C_1-C_6)$-alkylamino and mono-$(C_1-C_4)$-alkylamino stand for the purposes of the invention for an amino group having a straight-chain or branched alkyl substituent having respectively 1 to 6 and 1 to 4 carbon atoms. A straight-chain or branched monoalkylamino radical having 1 to 4 carbon atoms is preferred. Examples which may be preferably mentioned are: methylamino, ethylamino, n-propylamino, isopropylamino, n-butylamino, tert-butylamino, n-pentylamino and n-hexylamino.

Di-$(C_1-C_6)$-alkylamino and di-$(C_1-C_4)$-alkylamino stand for the purposes of the invention for an amino group having two identical or different straight-chain or branched alkyl substituents having in each case respectively 1 to 6 and 1 to 4 carbon atoms. A straight-chain or branched dialkylamino radical having in each case 1 to 4 carbon atoms is preferred. Examples which may be preferably mentioned are: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, N-tert-butyl-N-methylamino, N-methyl-N-n-pentylamino and N-n-hexyl-N-methylamino.

Mono- and di-$(C_1-C_4)$-alkylaminocarbonyl stand for the purposes of the invention for an amino group which is attached via a carbonyl group and has respectively one straight-chain or branched and two identical or different straight-chain or branched alkyl substituents having in each case 1 to 4 carbon atoms. Examples which may be preferably mentioned are: methylaminocarbonyl, ethyl-aminocarbonyl, n-propylaminocarbonyl, isopropylaminocarbonyl, n-butylaminocarbonyl, tert-butylaminocarbonyl, N,N-dimethylaminocarbonyl, N,N-diethylaminocarbonyl, N-ethyl-N-methyl-aminocarbonyl, N-methyl-N-n-propylaminocarbonyl, N-isopropyl-N-methylaminocarbonyl, N-n-butyl-N-methylaminocarbonyl and N-tert-butyl-N-methylaminocarbonyl.

$(C_1-C_4)$-Acyl [$(C_1-C_4)$-alkanoyl] stands for the purposes of the invention for a straight-chain or branched alkyl radical which has 1 to 4 carbon atoms, carries a doubly attached oxygen atom in the 1-position and is attached at the 1-position. Examples which may be preferably mentioned are: formyl, acetyl, propionyl, n-butyryl and isobutyryl.

$(C_1-C_4)$-Acylamino stands for the purposes of the invention for an amino group having a straight-chain or branched acyl substituent which has 1 to 4 carbon atoms and is attached via the carbonyl group to the nitrogen atom. Examples which may be preferably mentioned are: formylamino, acetylamino, propionylamino, n-butyrylamino and isobutyrylamino.

$(C_1-C_4)$-Acyloxy stands for the purposes of the invention for a straight-chain or branched alkyl radical which has 1 to 4 carbon atoms, which carries a doubly attached oxygen atom in the 1-position and is attached at the 1-position through a further oxygen atom. Examples which may be preferably mentioned are: acetoxy, propionoxy, n-butyroxy and isobutyroxy.

$(C_3-C_6)$-Cycloalkyl stands for the purposes of the invention for a monocyclic saturated cycloalkyl group having 3 to 6 ring carbon atoms. Examples which may be preferably mentioned are: cyclopropyl, cyclobutyl, cyclopentyl and cyclohexyl.

4- to 6-membered heterocyclyl stands for the purposes of the invention for a monocyclic saturated heterocycle which has a total of 4 to 6 ring atoms comprising one or two ring heteroatoms from the group consisting of N, O, S, SO and $SO_2$ and is attached via a ring carbon atom or, if appropriate, via a ring nitrogen atom. Preference is given to a 5- or 6-membered heterocycle having one or two ring heteroatoms from the group consisting of N, O and S. Examples which may be mentioned are: azetidinyl, oxetanyl, pyrrolidinyl, pyrazolidinyl, tetrahydrofuranyl, thiolanyl, piperidinyl, piperazinyl, tetrahydropyranyl, tetrahydrothiopyranyl, morpholinyl and thiomorpholinyl. Pyrrolidinyl, tetrahydrofuranyl, piperidinyl, piperazinyl, tetrahydropyranyl and morpholinyl are preferred.

5- or 6-membered heteroaryl stands for the purposes of the invention for an aromatic heterocycle (heteroaromatic) which has a total of 5 or 6 ring atoms comprising one or two ring heteroatoms from the group consisting of N, O and S and is attached via a ring carbon atom or, if appropriate, via a ring nitrogen atom. Examples which may be mentioned are: furyl, pyrrolyl, thienyl, pyrazolyl, imidazolyl, oxazolyl, thiazolyl, isoxazolyl, isothiazolyl, pyridyl, pyrimidinyl, pyridazinyl and pyrazinyl. Thienyl, pyrazolyl, imidazolyl, oxazolyl, thiazolyl, pyridyl and pyrimidinyl are preferred.

Halogen embraces for the purposes of the invention fluorine, chlorine, bromine and iodine. Preference is given to chlorine, fluorine or bromine; particular preference is given to fluorine or chlorine.

For the purposes of the invention, an oxo substituent is an oxygen atom which is attached via a double bond to a carbon atom.

When radicals in the compounds according to the invention are substituted, the radicals may be mono- or polysubstituted, unless specified otherwise. For the purposes of the present invention, the meanings of all radicals which occur more than once are independent of one another. Preference is given to substitution by one or two identical or different substituents. Very particularly preferred is substitution by one substituent.

Preference is given to compounds of the formula (I) in which
A represents CH or N,
and to their salts, solvates and solvates of the salts.

Preference is also given to compounds of the formula (I) in which
Y represents C—$R^7$
and
Z represents N,
and to their salts, solvates and solvates of the salts.

Preference is also given to compounds of the formula (I) in which
Y represents N
and
Z represents C—$R^9$,
and to their salts, solvates and solvates of the salts.

Preference is also given to compounds of the formula (I) in which
Y and Z both represent N,
and to their salts, solvates and solvates of the salts.

Preference is also given to compounds of the formula (I) in which
$R^1$ represents hydrogen, fluorine, chlorine, cyano, nitro, ($C_1$-$C_4$)-alkyl, difluoromethyl, trifluoromethyl, ($C_1$-$C_4$)-alkoxy, difluoromethoxy, trifluoromethoxy or a group of the formula —$SO_2$—$R^{20}$,
and to their salts, solvates and solvates of the salts.

Preference is also given to compounds of the formula (I) in which
$R^2$ represents cyano or a group of the formula —C(=O)—$R^{21}$, —C(=O)—O—$R^{21}$, —C(=O)—$NH_2$ or —C(=O)—NH—$R^{21}$ in which
$R^{21}$ represents ($C_1$-$C_4$)-alkyl which may be substituted by hydroxyl,
and
$R^3$ represents methyl,
and to their salts, solvates and solvates of the salts.

Preference is also given to compounds of the formula (I) in which
$R^4$ represents trifluoromethyl
and
$R^5$ represents hydrogen,
and to their salts, solvates and solvates of the salts.

Particular preference is given to compounds of the formula (I) in which
A represents CH,
Y represents C—$R^7$ or N,
Z represents C—$R^9$ or N,
where at least one of the two ring members Y and Z represents N
and in which
$R^7$ represents hydrogen, amino or a group of the formula —NH—C(=O)—$R^8$ or —NH—$SO_2$—$R^8$ in which
$R^8$ represents ($C_1$-$C_4$)-alkyl or ($C_3$-$C_6$)-cycloalkyl,
where ($C_1$-$C_4$)-alkyl may be substituted by hydroxyl, ($C_1$-$C_4$)-alkoxy or ($C_3$-$C_6$)-cycloalkyl and up to three times by fluorine
and
the cycloalkyl groups mentioned may be substituted up to two times by identical or different substituents from the group consisting of ($C_1$-$C_4$)-alkyl and up to two times by fluorine,
and
$R^9$ represents hydrogen, ($C_1$-$C_4$)-alkyl, ($C_1$-$C_4$)-alkoxy, ($C_1$-$C_4$)-alkoxycarbonyl, ($C_3$-$C_6$)-cycloalkyl or 5- or 6-membered heteroaryl,
where ($C_1$-$C_4$)-alkyl may be substituted by hydroxyl, ($C_1$-$C_4$)-alkoxy or ($C_3$-$C_6$)-cycloalkyl and up to three times by fluorine
and where
the cycloalkyl groups mentioned may be substituted up to two times by identical or different substituents from the group consisting of ($C_1$-$C_4$)-alkyl and up to two times by fluorine
and
the heteroaryl group mentioned may be substituted up to two times by identical or different substituents from the group consisting of fluorine, chlorine, cyano, ($C_1$-$C_4$)-alkyl, difluoromethyl, trifluoromethyl, ($C_1$-$C_4$)-alkoxy, difluoromethoxy and trifluoromethoxy,
or
$R^9$ represents a group of the formula —$SO_2$—$NR^{10}R^{11}$ or —$NR^{12}R^{13}$ in which
$R^{10}$ and $R^{11}$ are identical or different and independently of one another represent hydrogen, ($C_1$-$C_4$)-alkyl or ($C_3$-$C_6$)-cycloalkyl,
$R^{12}$ represents hydrogen, ($C_1$-$C_4$)-alkyl, ($C_3$-$C_6$)-cycloalkyl or ($C_1$-$C_4$)-alkylsulfonyl,
where ($C_1$-$C_4$)-alkyl may be substituted by cyano, hydroxyl, ($C_1$-$C_4$)-alkoxy, hydroxycarbonyl, ($C_1$-$C_4$)-alkoxycarbonyl, aminocarbonyl, mono-($C_1$-$C_4$)-alkylaminocarbonyl, di-($C_1$-$C_4$)-alkylaminocarbonyl or ($C_3$-$C_6$)-cycloalkyl and up to three times by fluorine
and
the cycloalkyl groups mentioned may be substituted up to two times by identical or different substituents from the group consisting of ($C_1$-$C_4$)-alkyl and up to two times by fluorine,
$R^{13}$ represents hydrogen, ($C_1$-$C_4$)-alkyl or a group of the formula —C(=O)—$R^{14}$, —C(=O)—O—$R^{15}$ or —C(=O)—$NR^{16}R^{17}$ in which
$R^{14}$ represents ($C_1$-$C_6$)-alkyl, ($C_3$-$C_6$)-cycloalkyl, 4- to 6-membered heterocyclyl or 5- or 6-membered heteroaryl, where (C₁-C₆)-alkyl may be substituted by hydroxyl, (C₁-C₄)-alkoxy, (C₁-C₄)-acyloxy, amino, mono-(C₁-C₄)-alkylamino, di-(C₁-C₄)-alkylamino, (C₁-C₄)-acylamino, (C₁-C₄)-alkoxycarbonylamino or (C₃-C₆)-cycloalkyl and up to three times by fluorine and where the cycloalkyl and heterocyclyl groups mentioned may be substituted up to two times by identical or different substituents from the group consisting of ($C_1$-$C_4$)-alkyl and up to two times by fluorine and the heteroaryl group mentioned may be substituted up to two times by identical or different substituents from the group consisting of fluorine, chlorine, cyano, ($C_1$-$C_4$)-alkyl, difluoromethyl, trifluoromethyl, ($C_1$-$C_4$)-alkoxy, difluoromethoxy and trifluoromethoxy, $R^{15}$ represents ($C_1$-$C_4$)-alkyl which may be substituted by ($C_3$-$C_6$)-cycloalkyl or phenyl, and $R^{16}$ and $R^{17}$ are identical or different and independently of one another represent hydrogen or ($C_1$-$C_4$)-alkyl which may be substituted by hydroxyl or ($C_1$-$C_4$)-alkoxy, $R^1$ represents hydrogen, fluorine, chlorine, nitro, methyl, difluoromethyl, trifluoromethyl or a group of the formula —$SO_2$—$R^{20}$ in which $R^{20}$ represents ($C_1$-$C_4$)-alkyl which may be substituted by hydroxyl, methoxy or ethoxy or up to three times by fluorine, $R^2$ represents cyano or a group of the formula —C(=O)—$R^{21}$ or —C(=O)—O—$R^{21}$ in which $R^{21}$ represents methyl, ethyl or 2-hydroxyethyl, $R^3$ represents methyl, $R^4$ represents trifluoromethyl and $R^5$ represents hydrogen, and to their salts, solvates and solvates of the salts.

Special preference is given to compounds of the formula (I) in which

A represents CH,

Y represents C—$R^7$ or N,

Z represents C—$R^9$ or N, where either Y represents C—$R^7$ and Z represents N or Y represents N and Z represents C—$R^9$ and in which $R^7$ represents amino or a group of the formula —NH—C(=O)—$R^8$ in which $R^8$ represents ($C_1$-$C_4$)-alkyl or ($C_3$-$C_6$)-cycloalkyl, where ($C_1$-$C_4$)-alkyl may be substituted by hydroxyl, methoxy, ethoxy or ($C_3$-$C_6$)-cycloalkyl and up to three times by fluorine and the cycloalkyl groups mentioned may be substituted up to two times by methyl and up to two times by fluorine, and $R^9$ represents ($C_1$-$C_4$)-alkyl, ($C_1$-$C_4$)-alkoxy or ($C_3$-$C_6$)-cycloalkyl, where ($C_1$-$C_4$)-alkyl may be substituted by hydroxyl, methoxy, ethoxy or ($C_3$-$C_6$)-cycloalkyl and up to three times by fluorine and the cycloalkyl groups mentioned may be substituted up to two times by methyl and up to two times by fluorine, or $R^9$ represents a group of the formula —$SO_2$—$NR^{10}R^{11}$ or —$NR^{12}R^{13}$ in which $R^{10}$ and $R^{11}$ are identical or different and independently of one another represent hydrogen, methyl, ethyl or cyclopropyl, $R^{12}$ represents hydrogen, ($C_1$-$C_4$)-alkyl, ($C_3$-$C_6$)-cycloalkyl or ($C_1$-$C_4$)-alkylsulfonyl, where ($C_1$-$C_4$)-alkyl may be substituted by cyano, hydroxyl, ($C_1$-$C_4$)-alkoxy, hydroxycarbonyl, ($C_1$-$C_4$)-alkoxycarbonyl, aminocarbonyl, mono-($C_1$-$C_4$)-alkylaminocarbonyl, di-($C_1$-$C_4$)-alkylaminocarbonyl or ($C_3$-$C_6$)-cycloalkyl and up to three times by fluorine and the cycloalkyl groups mentioned may be substituted up to two times by methyl and up to two times by fluorine, $R^{13}$ represents hydrogen or a group of the formula —C(=O)—$R^{14}$ or —C(=O)—$NR^{16}R^{17}$ in which $R^{14}$ represents ($C_1$-$C_4$)-alkyl, ($C_3$-$C_6$)-cycloalkyl or 5- or 6-membered heteroaryl, where ($C_1$-$C_4$)-alkyl may be substituted by hydroxyl, ($C_1$-$C_4$)-alkoxy, amino, mono-($C_1$-$C_4$)-alkylamino, di-($C_1$-$C_4$)-alkylamino, ($C_1$-$C_4$)-acylamino or ($C_3$-$C_6$)-cycloalkyl and up to three times by fluorine and where the cycloalkyl groups mentioned may be substituted up to two times by methyl and up to two times by fluorine and the heteroaryl group mentioned may be substituted up to two times by identical or different substituents from the group consisting of fluorine, cyano, methyl, difluoromethyl, trifluoromethyl, methoxy and trifluoromethoxy, and $R^{16}$ and $R^{17}$ are identical or different and independently of one another represent hydrogen or ($C_1$-$C_4$)-alkyl which may be substituted by hydroxyl, methoxy or ethoxy, $R^1$ represents hydrogen, nitro, trifluoromethyl, methylsulfonyl or trifluoromethylsulfonyl, $R^2$ represents cyano, acetyl, ethoxycarbonyl or (2-hydroxyethoxy)carbonyl, $R^3$ represents methyl, $R^4$ represents trifluoromethyl and $R^5$ represents hydrogen, and to their salts, solvates and solvates of the salts.

Very particular preference is given to compounds of the formula (I) in which

A represents CH,

Y represents N,

Z represents C—$R^9$ in which $R^9$ represents a group of the formula —$NHR^{12}$ or —NH—C(=O)—$R^{14}$ in which $R^{12}$ represents a group of the formula —$CH_2$—C(=O)—OH or —$CH_2$—C(=O)—$NH_2$ and $R^{14}$ represents ($C_3$-$C_6$)-cycloalkyl which may be substituted up to two times by methyl and up to two times by fluorine, or ($C_1$-$C_4$)-alkyl, $R^1$ represents hydrogen or methylsulfonyl,
$R^2$ represents cyano,
$R^3$ represents methyl,
$R^4$ represents trifluoromethyl
and
$R^5$ represents hydrogen,
and to their salts, solvates and solvates of the salts.

Of particular importance are compounds according to formula (I) having the configuration shown in formula (I-ent) at the 4-position of the dihydropyrimidine ring

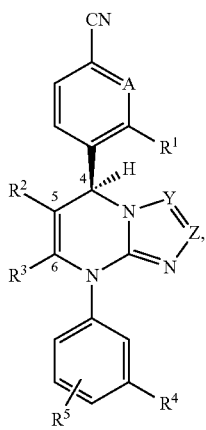
(I-ent)

in which A, Y, Z, $R^1$, $R^2$, $R^3$, $R^4$ and $R^5$ each have the meanings given above,
and their salts, solvates and solvates of the salts.

Specific radical definitions given in the respective combinations or preferred combinations of radicals are, independently of the combinations of radicals given in each case, also replaced by any radical definitions of other combinations.

Very particular preference is given to combinations of two or more of the preferred ranges mentioned above.

The invention furthermore provides a process for preparing the compounds of the formula (I) according to the invention, characterized in that initially a compound of the formula (II)

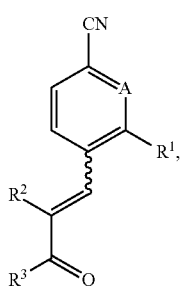
(II)

in which A, $R^1$, $R^2$ and $R^3$ each have the meanings given above, is reacted in the presence of a base with a compound of the formula (III)

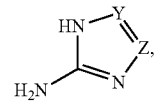
(III)

in which Y and Z have the meanings given above,
to give an intermediate of the formula (IV)

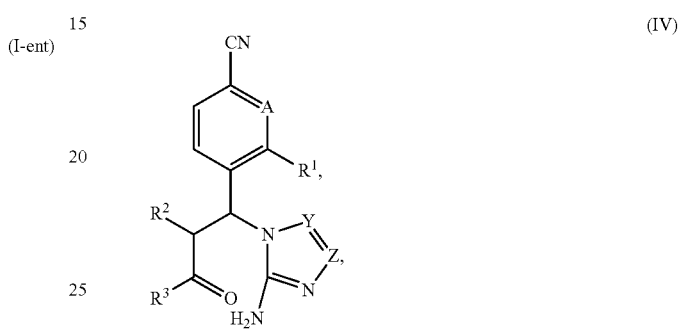
(IV)

in which A, Y, Z, $R^1$, $R^2$ and $R^3$ each have the meanings given above,
this is then cyclized in situ or in a separate acid-catalyzed reaction step to give a compound of the formula (V)

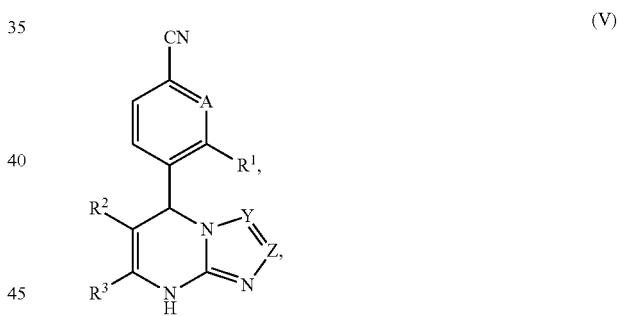
(V)

in which A, Y, Z, $R^1$, $R^2$ and $R^3$ each have the meanings given above,
and the compound (V) is then coupled in the presence of a copper(II) catalyst and a base with a phenylboronic acid of the formula (VI)

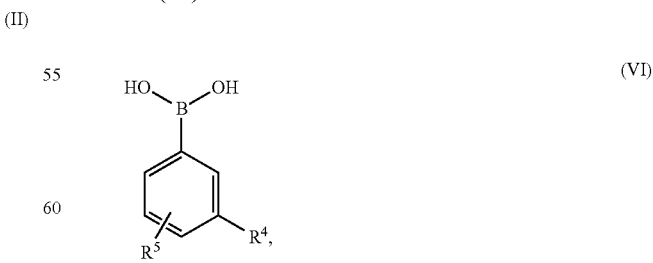
(VI)

in which $R^4$ and $R^5$ have the meanings given above,
to give a compound of the formula (I)
and the compounds of the formula (I) obtained in this manner are, if appropriate, separated by methods known to the person skilled in the art into their enantiomers and/or diastereomers and/or converted with the appropriate (i) solvents and/or (ii) bases or acids into their solvates, salts and/or solvates of the salts.

Solvents suitable for the process step (II)+(III)→(IV) are customary organic solvents which do not change under the reaction conditions. These include in particular halogenated hydrocarbons such as dichloromethane, trichloromethane, carbon tetrachloride, 1,2-dichloroethane or chlorobenzene, or solvents such as pyridine, dimethyl sulfoxide (DMSO), N,N-dimethylformamide (DMF), N,N-diethylformamide, N,N-dimethylacetamide (DMA), N,N'-dimethylpropyleneurea (DMPU) or N-methylpyrrolidinone (NMP). It is also possible to use mixtures of the solvents mentioned. Preference is given to using dichloromethane, pyridine, N,N-dimethylformamide or mixtures thereof.

Suitable bases for process step (II)+(III)→(IV) are in particular proline (in racemic or enantiomerically pure form) and also customary organic amine bases such as, for example, triethylamine, N,N-diisopropylethylamine, piperidine, N-methylpiperidine or N-methylmorpholine. Preference is given to using D,L-proline.

The process step (II)+(III)→(IV) is generally carried out in a temperature range of from 0° C. to +100° C., preferably at from +20° C. to +50° C. The reaction can be carried out at normal, elevated or reduced pressure (for example from 0.5 to 5 bar); in general, the reaction is carried out at atmospheric pressure.

The cyclization in process step (IV)→(V) is preferably carried out in solvents such as benzene, toluene, xylene or pyridine or in mixtures thereof at the respective reflux temperature. If appropriate, it may be advantageous to carry out the reaction under microwave irradiation.

Suitable acid catalysts for this reaction are customary inorganic or organic acids such as, for example, sulfuric acid, hydrogen chloride/hydrochloric acid, trifluoroacetic acid, methanesulfonic acid, trifluoromethanesulfonic acid, camphorsulfonic acid, benzenesulfonic acid, p-toluenesulfonic acid or pyridinium p-toluenesulfonate. Preference is given to using p-toluenesulfonic acid.

With sufficiently electron-rich compounds of the formula (III), the reaction sequence (II)+(III)→(IV)→(V) can also be carried out in one step. Suitable bases for such a one-step reaction are in particular weak bases such as sodium bicarbonate or potassium bicarbonate or sodium dihydrogen phosphate or potassium dihydrogen phosphate. Preference is given to using sodium bicarbonate.

The reaction is preferably carried out in dipolar aprotic solvents such as dimethyl sulfoxide (DMSO), N,N-dimethylformamide (DMF), N,N-diethylformamide, N,N-dimethylacetamide (DMA), N,N'-dimethylpropyleneurea (DMPU) or N-methylpyrrolidinone (NMP) in a temperature range of from +50° C. to +80° C. Preference is given to using N,N-dimethylformamide. The reaction can be carried out at atmospheric, elevated or reduced pressure (for example from 0.5 to 5 bar); in general, the reaction is carried out at atmospheric pressure.

Inert solvents for process step (V)+(VI)→(I) are, for example, ethers such as diethyl ether, diisopropyl ether, methyl tert-butyl ether, 1,2-dimethoxyethane, dioxane or tetrahydrofuran, hydrocarbons such as pentane, hexane, cyclohexane, benzene, toluene or xylene, halogenated hydrocarbons such as dichloromethane, 1,2-dichloroethane or trichloromethane, or other solvents such as pyridine, acetonitrile, dimethyl sulfoxide (DMSO), N,N-dimethylformamide (DMF), N,N'-dimethylpropyleneurea (DMPU) or N-methylpyrrolidinone (NMP). It is also possible to use mixtures of the solvents mentioned. Preference is given to using dichloromethane or a mixture of dichloromethane and pyridine.

Suitable bases for the process step (V)+(VI)→(I) are customary inorganic or organic bases. These include in particular alkali metal bicarbonates such as sodium bicarbonate or potassium bicarbonate, alkali metal carbonates or alkaline earth metal carbonates such as lithium carbonate, sodium carbonate, potassium carbonate, calcium carbonate or cesium carbonate, alkali metal hydrogen phosphates such as disodium hydrogen phosphate or dipotassium hydrogen phosphate, alkali metal hydroxides or alkaline earth metal hydroxides such as lithium hydroxide, sodium hydroxide, potassium hydroxide or barium hydroxide, amides such as lithium bis(trimethylsilyl)-amide or potassium bis(trimethylsilyl)amide or lithium diisopropylamide (LDA), or organic amine bases such as triethylamine, N-methylmorpholine, N-methylpiperidine, N,N-diisopropylethylamine, 1,5-diazabicyclo[4.3.0]non-5-ene (DBN), 1,8-diazabicyclo[5.4.0]undec-7-ene (DBU), pyridine or 2,6-lutidine. Preference is given to using triethylamine, if appropriate in combination with pyridine.

Preferred catalysts for the transition metal-catalyzed N-arylation reaction (V)+(VI)→(I) copper(II) salts such as copper(II) acetate, carbonate, chloride or sulfate, optionally in combination with activated elemental copper. Alternatively, it is also possible to use palladium(0) or palladium(II) compounds such as, for example palladium black, tetrakis(triphenylphosphine)palladium(0), bis(dibenzylideneaceton) palladium(0), palladium(II) chloride, palladium(II) acetate or palladium(II) trifluoroacetate, if appropriate in combination with complex ligands such as acetonitrile, benzonitrile, tri-n-butylphosphine, tri-tert-butylphosphine, triphenylphosphine, tri-o-tolylphosphine, 1,2-bis(diphenylphosphino)ethane, 1,1'-bis(diphenylphosphino)ferrocene or dicyclohexyl-(2',4',6'-triisopropylbiphenyl-2-yl)phosphine. Mixed palladium/copper systems are also suitable. The catalyst used is preferably copper(II) acetate, alone or in combination with activated copper.

The coupling reaction (V)+(VI)→(I) is generally carried out in a temperature range of from +20° C. to +150° C., preferably at from +20° C. to +60° C. If appropriate, a reaction under microwave irradiation may be advantageous.

If in the compound of the formula (V) Z represents C—$R^9$ in which $R^9$ represents amino, it is necessary to deactivate this amino group with a protective group prior to the coupling reaction with the phenylboronic acid (VI). Suitable for this purpose are customary amino protective groups such as, for example, a phthalimide, trityl, benzylidene, diphenylmethylene, trifluoroacetyl, benzyloxycarbonyl or tert-butoxycarbonyl group. Introduction and removal of these protective groups are carried out by known methods familiar to the person skilled in the art [see, for example, T. W. Greene and P. G. M. Wuts, *Protective Groups in Organic Synthesis*, Wiley, New York, 1999]. Preference is given to using a phthalimide or a trifluoroacetyl group.

Some of the thus N-protected compounds obtained after coupling with phenylboronic acid (VI) also show significant HNE-inhibitory action, and they are therefore included in the scope of the present invention, i.e. the compounds of the formula (I).

In these N-arylation reactions, instead of phenylboronic acid (VI), it is also possible to use the corresponding phenyl bromides, iodides or trifluormethanesulfonates as coupling partners. Here, the reaction parameters described above, such as solvents, bases, catalysts, reaction temperatures and any protective groups, are applied analogously.

The compounds of the formula (II) can be obtained by processes known from the literature by acid- and/or base-catalyzed condensation of an aldehyde of the formula VII) with a keto compound of the formula (VIII)

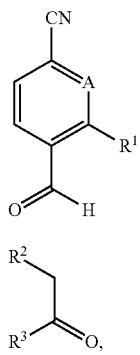

(VII)

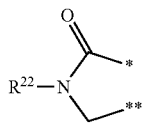

(VIII)

in which A and $R^1$ and $R^2$ and $R^3$, respectively, have the meanings given above,

[cf. also Reaction Schemes 4, 5 and 7 below].

Compounds of the formula (I) according to the invention in which $R^2$ and $R^3$ are attached to one another and together form a fused group of the formula $$R^{22}-N\underset{**}{\overset{O}{\underset{\phantom{|}}{\bigvee}}}*$$

in which * and ** denote the points of attachment described above and $R^{22}$ has the meaning given above can also be prepared by brominating a compound of the formula (I-A)

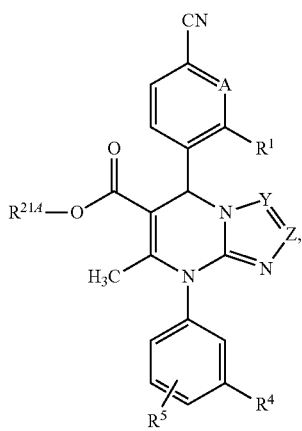

(I-A)

in which A, Y, Z, $R^1$, $R^4$ and $R^5$ each have the meanings given above and $R^{214}$ represents $(C_1-C_6)$-alkyl, $(C_3-C_6)$-alkenyl or $(C_3-C_6)$-cycloalkyl in an inert solvent to give a compound of the formula (IX)

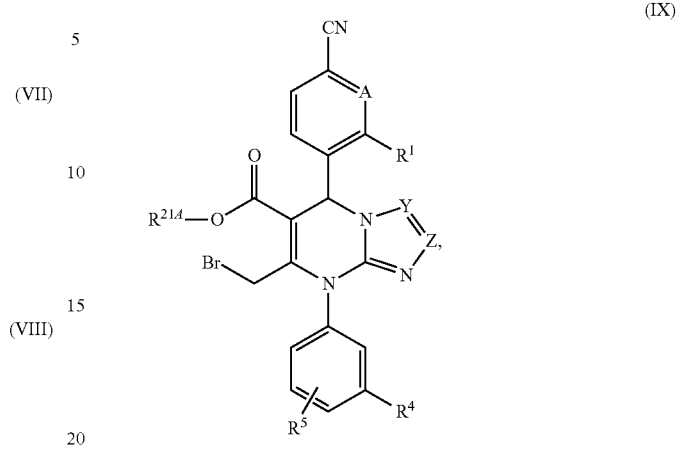

(IX)

in which A, Y, Z, $R^1$, $R^4$, $R^5$ and $R^{214}$ each have the meanings given above, and then reacting with a compound of the formula (X)

$$R^{22}-NH_2 \qquad (X),$$

in which $R^{22}$ has the meaning given above,
with cyclization to give a compound of the formula (I-B)

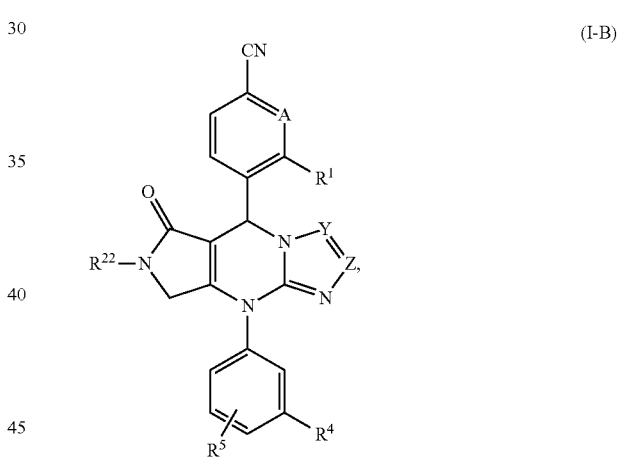

(I-B)

in which A, Y, Z, $R^1$, $R^4$, $R^5$ and $R^{22}$ each have the meanings given above.

The bromination in process step (I-A)→(IX) is preferably carried out using elemental bromine in a customary inert solvent such as chloroform at a temperature of from −20° C. to +40° C. Under these reaction conditions, any CC double bonds [$R^{214}=(C_3-C_6)$-alkenyl] present in the radical $R^{214}$ may also be brominated; however, this does not have any interfering effect in the subsequent ring closure reaction with the compound (X).

The lactam formation in process step (IX)+(X)→(I-B) is preferably carried out in acetone or an ether such as tetrahydrofuran or dioxane as inert solvent at a temperature of from −20° C. to +60° C. If appropriate, the use of a tertiary amine such as triethylamine, N-methylmorpholine, N-methylpiperidine or N,N-diisopropylethylamine as auxiliary base may be advantageous.

For its part, the compound of the formula (I-A) can be obtained analogously to the reactions (II)+(III)→(IV)→(V) and (V)+(VI)→(I) described above.

Compounds of the formula (I) according to the invention in which Y represents C—R⁷, in which R⁷ represents amino, and Z represents N can be prepared by converting a compound of the formula (XI)

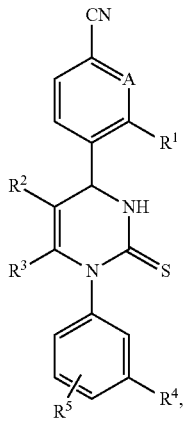

(XI)

in which A, R¹, R², R³, R⁴ and R⁵ each have the meanings given above
with hydrazine hydrate in the presence of a suitable oxidizing agent into a compound of the formula (XII)

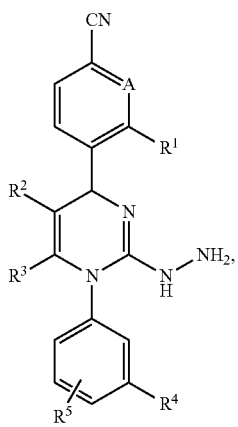

(XII)

in which A, R¹, R², R³, R⁴ and R⁵ each have the meanings given above,
and then reacting this with cyanogen bromide with cyclization to a compound of the formula (I—C)

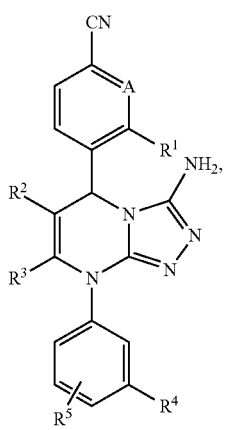

(I-C)

in which A, R¹, R², R³, R⁴ and R⁵ each have the meanings given above.

The desulfurization during the process step (XI)→(XII) is preferably carried out under oxidative conditions. A particularly suitable oxidizing agent is tert-butyl hydroperoxide (TBHP); alternatively, it is also possible to use, for example, hydrogen peroxide or m-chloroperbenzoic acid.

Suitable inert solvents for this reaction are in particular alcohols such as methanol, ethanol, n-propanol, isopropanol, n-butanol or tert-butanol, or hydrocarbons such as pentane, hexane, nonane, decane, cyclohexane, benzene, toluene or xylene, or else water. It is also possible to use mixtures of such solvents. Preference is given to using toluene in a mixture with methanol or ethanol.

The transformation (XI)→(XII) is generally carried out in a temperature range of from −20° C. to +100° C., preferably at from 0° C. to +60° C. If appropriate, it may be advantageous to carry out the reaction under microwave irradiation.

Inert solvents for the reaction with cyanogen bromide in process step (XII)→(I-C) are, for example, alcohols such as methanol, ethanol, n-propanol, isopropanol, n-butanol, tert-butanol or 2-methoxyethanol, ethers such as diethyl ether, diisopropyl ether, methyl tert-butyl ether, 1,2-dimethoxyethane, dioxane or tetrahydrofuran, halogenated hydrocarbons such as dichloromethane, 1,2-dichloroethane or trichloromethane, or dipolar aprotic solvents such as acetone, acetonitrile, dimethyl sulfoxide (DMSO), N,N-dimethylformamide (DMF), N,N'-dimethylpropyleneurea (DMPU) or N-methylpyrrolidinone (NMP), and also mixtures of these solvents. Preference is given to using methanol.

The reaction with cyanogen bromide and the subsequent cyclisation to the compound (I-C) can be carried out without addition of an auxiliary base; however, if appropriate, it may be advantageous to use a customary inorganic or organic base such as, for example, sodium carbonate or potassium carbonate, sodium acetate, sodium hydroxide or potassium hydroxide, lithium bis(trimethylsilyl)-amide or potassium bis(trimethylsilyl)amide, triethylamine, N-methylmorpholine, N-methylpiperidine or N,N-diisopropylethylamine.

The transformation (XII)→(I-C) is generally carried out in a temperature range of from −20° C. to +80° C., preferably at from 0° C. to +40° C. Here, too, it may be advantageous to carry out the reaction under microwave irradiation.

For their part, the compounds of the formula (XI) can be prepared analogously to processes known from the literature, for example by polyphosphoric ester-catalyzed condensation of an aldehyde of the formula (VII) with a keto compound of the formula (VIII) and a thiourea derivative of the formula (XIII)

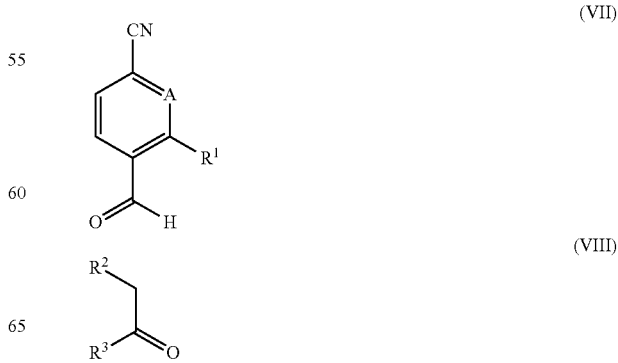

(VII)

(VIII)

-continued

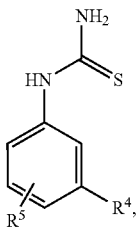
(XIII)

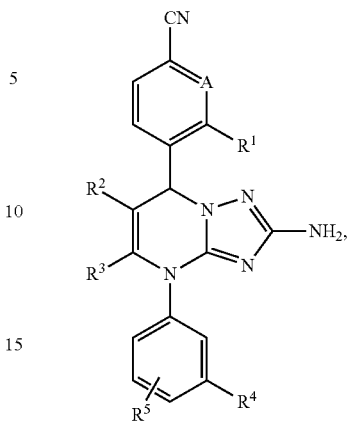
(I-D)

in which A, $R^1$, $R^2$, $R^3$, $R^4$ and $R^5$ each have the meanings given above,
[cf. also the subsequent Reaction Scheme 8 and the processes described in WO 2004/024701].

If expedient, further compounds of the formula (I) according to the invention can also be prepared by transformations of functional groups of individual substituents, in particular those listed under $R^1$, $R^2$, $R^7$ and $R^9$, starting with other compounds of the formula (I) obtained by the above process. These transformations are carried out according to customary methods known to the person skilled in the art and include, for example, reactions such as nucleophilic or electrophilic substitution reactions, transition metal-mediated coupling reactions (for example Suzuki or Heck reaction), oxidation, reduction, hydrogenation, alkylation, acylation, amination, hydroxylation, etherification, esterification, ester cleavage and ester hydrolysis, formation of nitriles, carboxamides, sulphonamides, carbamates and ureas, and also the introduction and removal of temporary protective groups [cf. also the Reaction Schemes 6 and 8 below and the exemplary embodiments].

Thus, for example, compounds of the formula (I) in which Y represents N and Z represents C—$R^9$, in which $R^9$ represents —$NR^{12}R^{13}$, and $R^{12}$ and $R^{13}$ for their part have the meanings given above, can be obtained by appropriate N-alkylation or N-acylation reactions starting with a compound of the formula (I-D)

in which A, $R^1$, $R^2$, $R^3$, $R^4$ and $R^5$ each have the meanings given above,
where the compound (I-D) for its part can be obtained by the general process described above [cf. also Reaction Schemes 5 and 6 below].

Separation of the compounds according to the invention into the corresponding enantiomers and/or diastereomers is possible, as expedient, at the stage of the compounds (I), (I-A), (I-B), (I-C) or (I-D) or even as early as at the stage of the compounds (V), (XI) or (XII), where the latter can then, in separated form, be reacted further according to the process steps described above. Such a separation of stereoisomers can be carried out by customary methods known to the person skilled in the art; preference is given to chromatographic methods, in particular to HPLC chromatography on a chiral phase.

The compounds of the formulae (III), (VI), (VIII), (X) and (XIII) are commercially available, known per se from the literature or can be prepared by customary methods described in the literature.

Some of the compounds of the formula (VII) are commercially available or known from the literature, or they can be prepared analogously to processes described in the literature [cf. also Reaction Schemes 1-3 below and the literature cited therein].

The processes described above can be illustrated in an exemplary manner by the reaction schemes below:

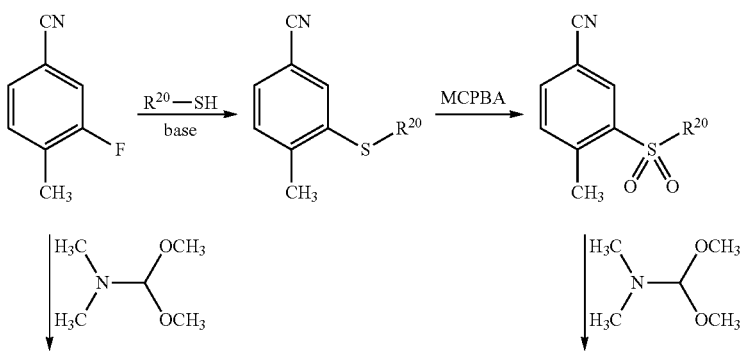

Scheme 1

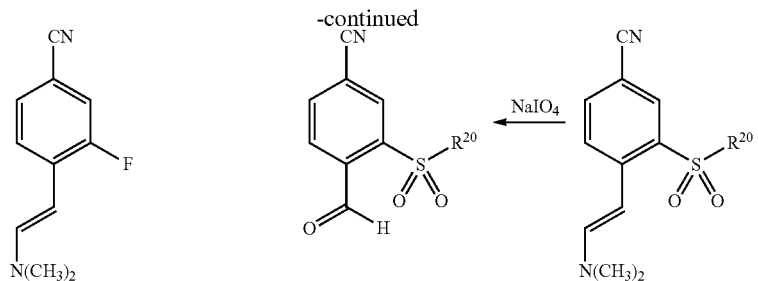
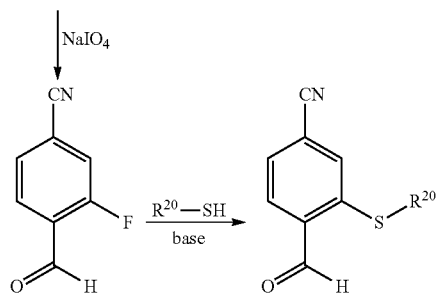
Scheme 2
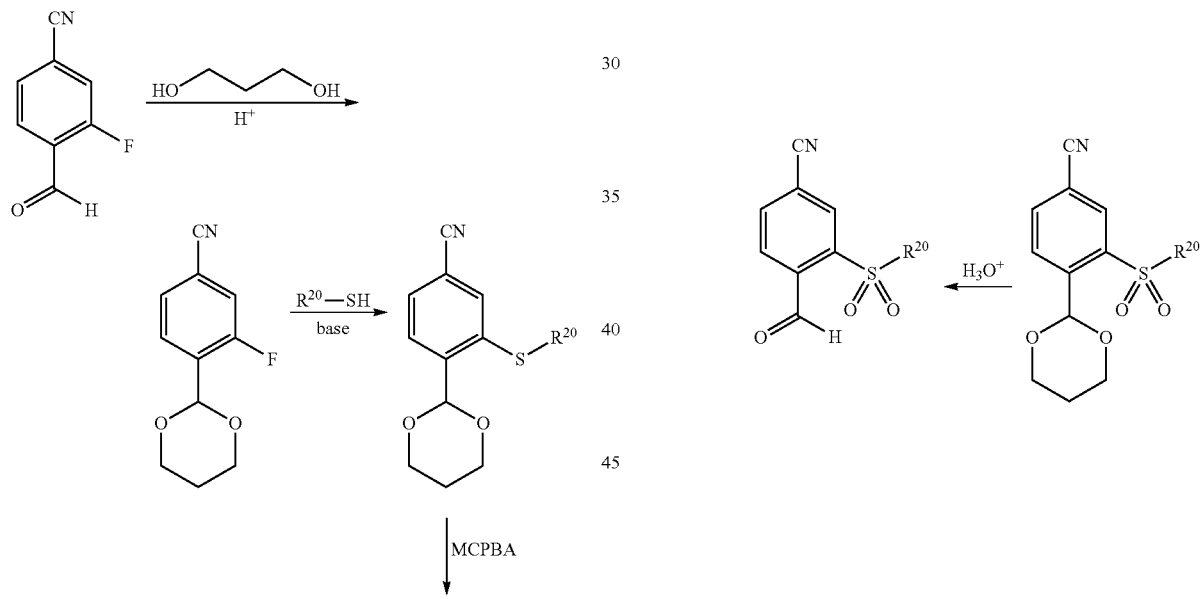
Scheme 3
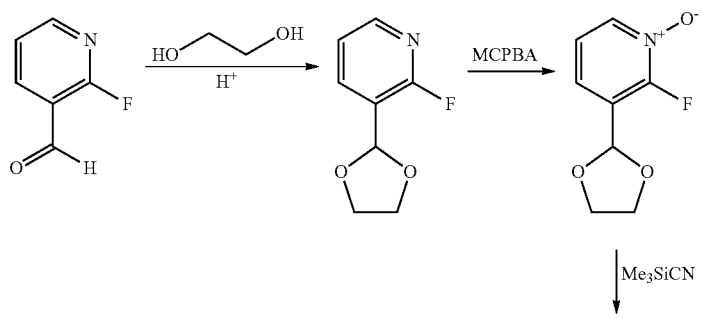

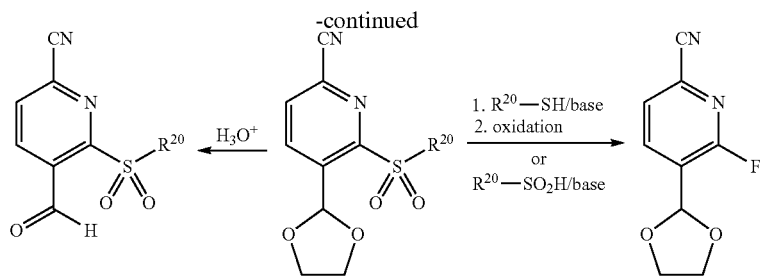
[cf., for example, W. K. Fife, *J. Org. Chem.* 48, 1375 (1983); H. Vorbrüggen and K. Krolikiewicz, *Synthesis*, 316 (1983); R. T. Shuman et al., *J. Org. Chem.* 55, 738 (1990); C. S. Burgey et al., *J. Med. Chem.* 46 (4), 461 (2003); J. J. Li et al., *J. Med. Chem.* 39, 1846 (1996); K. N. Dack et al., *Bioorg. Med. Chem. Lett.* 8 (16), 2061 (1998)].
Scheme 4
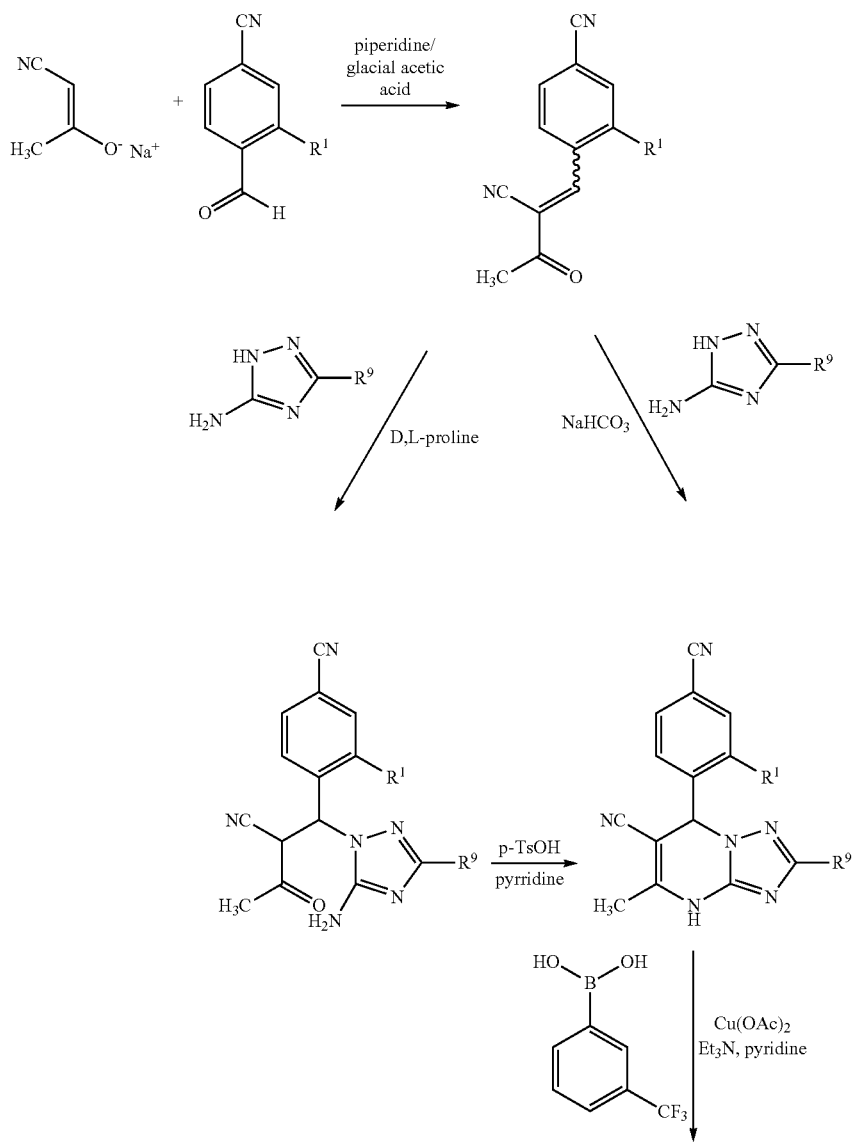

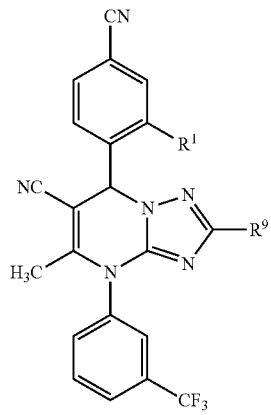
Scheme 5
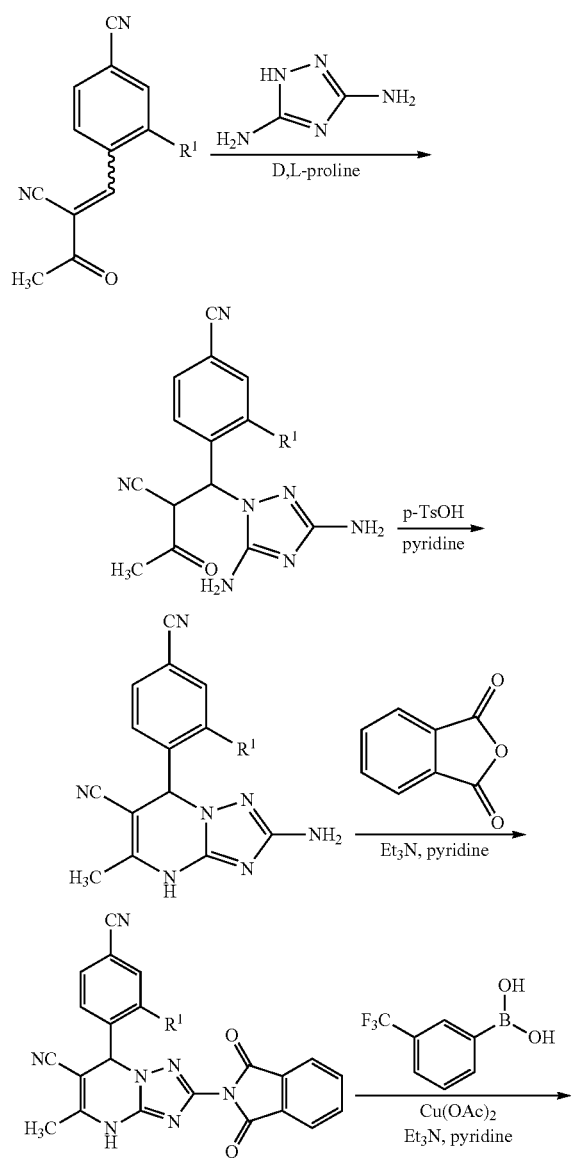
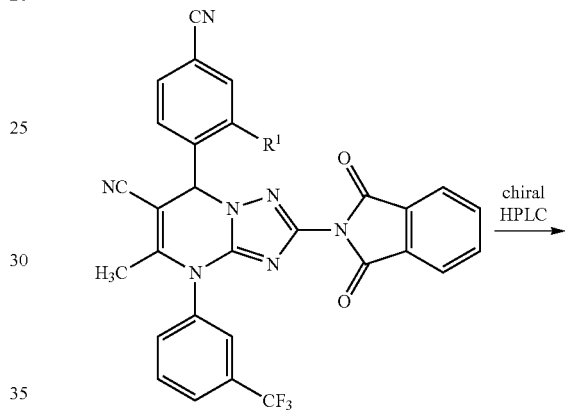
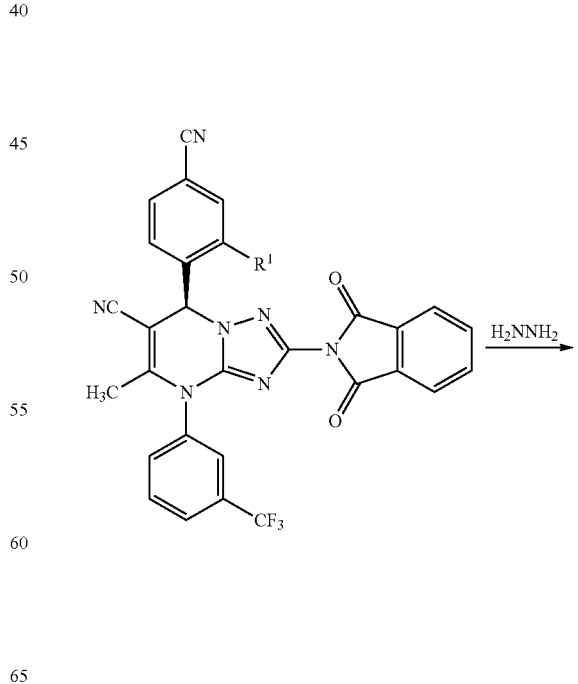

Scheme 6
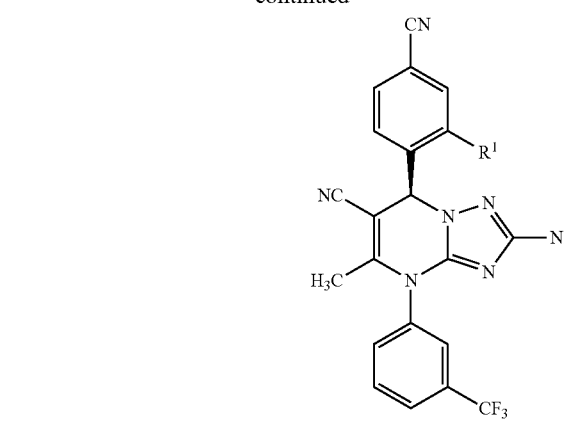
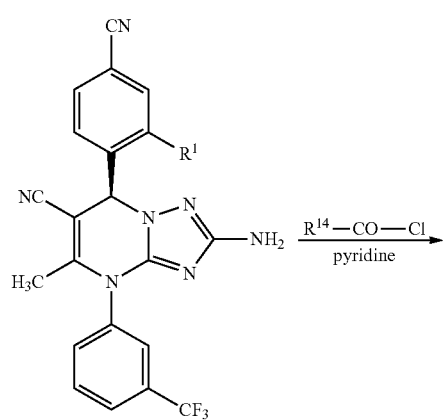
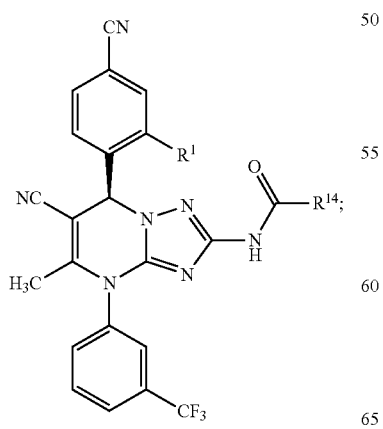
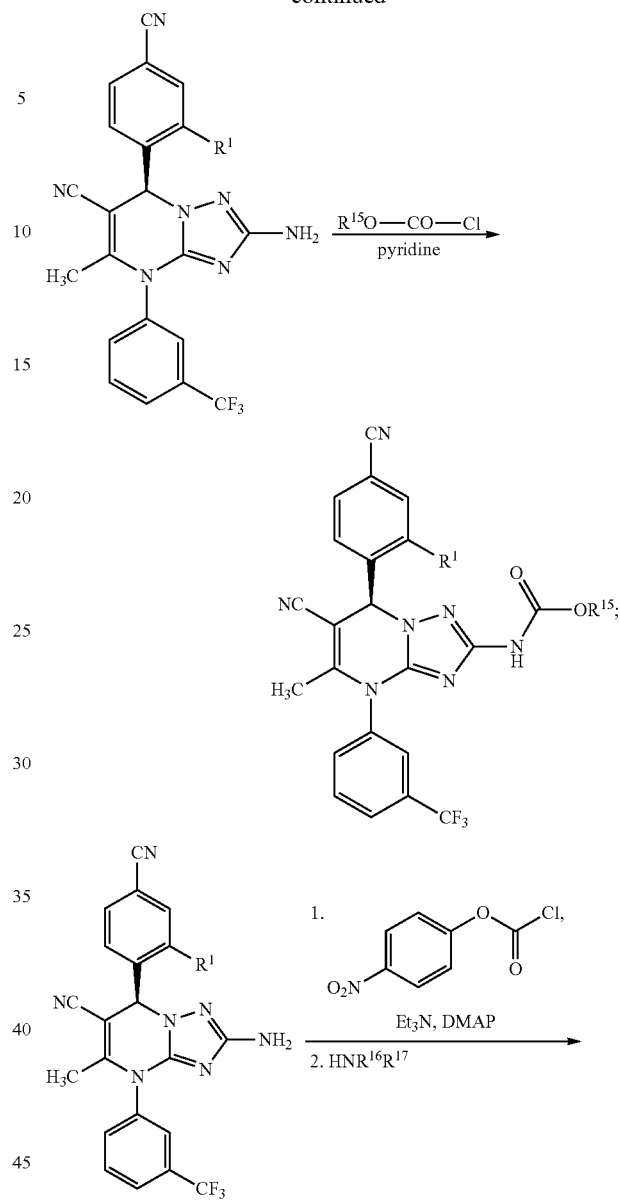
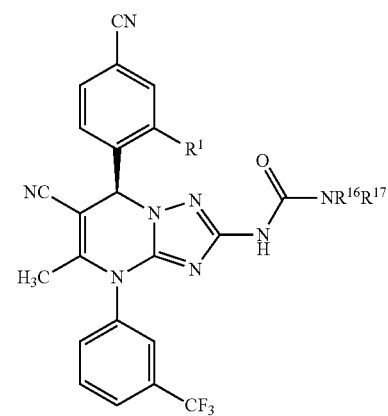

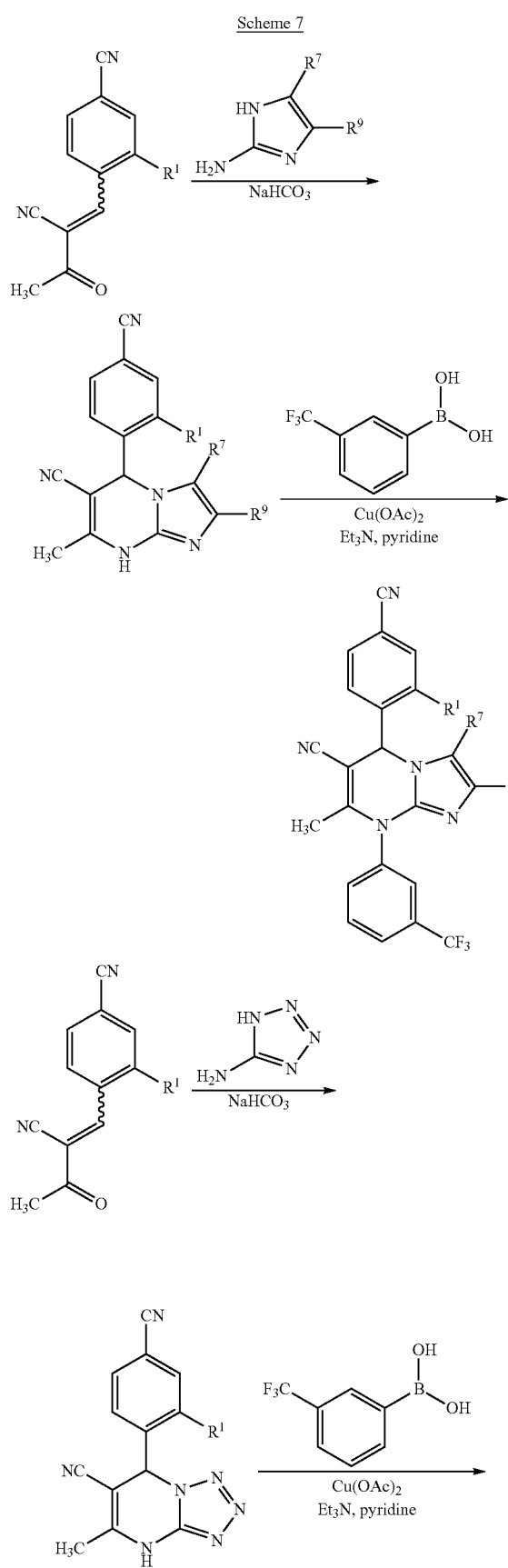
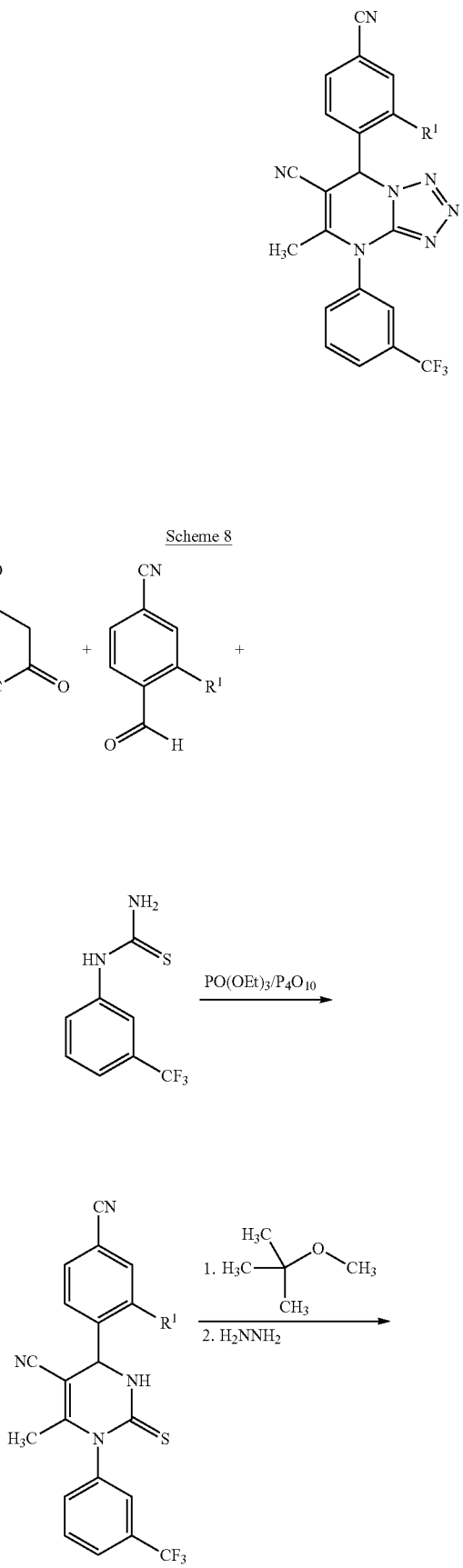
Scheme 7
Scheme 8

-continued

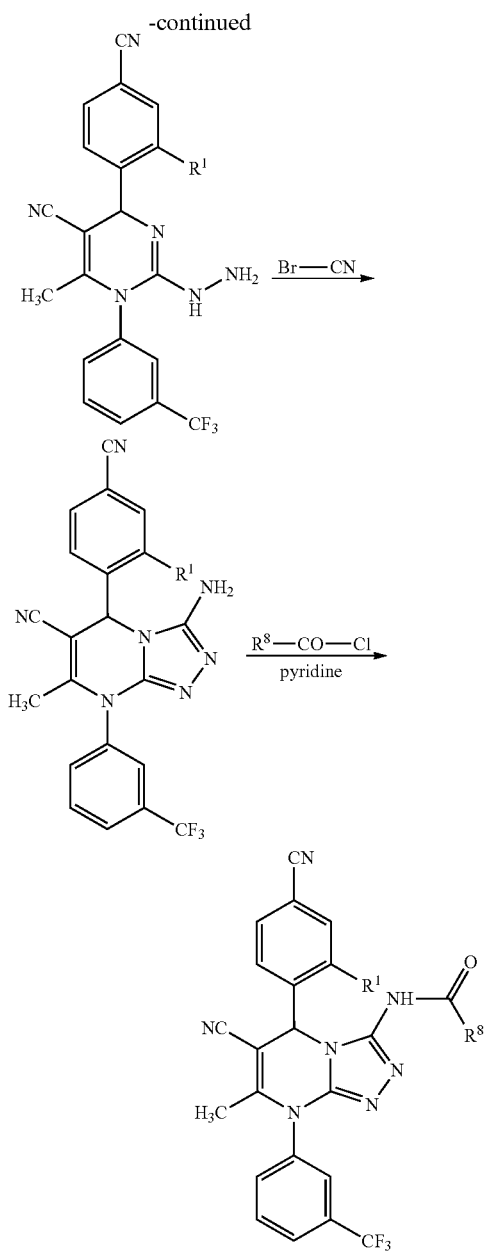

The compounds according to the invention have useful pharmacological properties and can be used for prevention and treatment of disorders in humans and animals.

The compounds according to the invention are potent low-molecular-weight, unreactive and selective inhibitors of human neutrophil elastase (HNE) and are therefore suitable for the treatment and/or prevention in particular of those disorders and pathological processes where neutrophil elastase is involved in an inflammatory event and/or a tissue or vessel remodeling.

For the purposes of the present invention, this includes in particular disorders such as pulmonary arterial hypertension (PAH) and other forms of pulmonary hypertension (PH), chronic obstructive pulmonary disease (COPD), acute respiratory distress syndrome (ARDS), acute lung injury (ALI), alpha-1-antitrypsin deficiency (AATD), pulmonary fibrosis, pulmonary emphysema, cystic fibrosis (CF), acute coronary syndrome (ACS), inflammations of the heart muscle (myo- carditis), and other autoimmune disorders of the heart (pericarditis, endocarditis, valvulitis, aortitis, cardiomyopathies), myocardial infarction, cardiogenic shock, heart failure, aneurysms, sepsis (SIRS), multi-organ failure (MODS, MOF), arteriosclerosis, inflammatory disorders of the kidney, chronic inflammations of the intestine (IBD, CD, UC), pancreatitis, peritonitis, rheumatoid disorders, inflammatory skin disorders and also inflammatory eye disorders.

The compounds according to the invention can furthermore be used for the treatment and/or prevention of asthmatic disorders of various degrees of severity with intermittent or persistent course (refractive asthma, bronchial asthma, allergic asthma, intrinsic asthma, extrinsic asthma, asthma induced by medicaments or by dust), of various forms of bronchitis (chronic bronchitis, infectious bronchitis, eosinophilic bronchitis), of Bronchiolitis obliterans, bronchiectasia, pneumonia, farmer's lung and related diseases, coughs and colds (chronic inflammatory cough, iatrogenic cough), inflammations of the nasal mucosa (including medicament-related rhinitis, vasomotoric rhinitis and seasonal allergic rhinitis, for example hay fever) and of polyps.

In addition, the compounds according to the invention can also be used for the treatment and/or prevention of micro- and macrovascular injuries (vasculitis), reperfusion damage, arterial and venous thromboses, diabetic and non-diabetic nephropathy, glomerulonephritis, glomerulosclerosis, nephrotic syndrome, hypertensive nephrosclerosis, microalbuminuria, acute and chronic renal insufficiency, acute and chronic renal failure, cystitis, urethritis, prostatitis, epidymitis, oophoritis, salpingitis, vulvovaginitis, erectile dysfunction, Hunner's ulcer, Peyronie's disease, arterial hypertension, shock, atrial and ventricular arrhythmias, transitory and ischemic attacks, heart failure, stroke, endothelial dysfunction, peripheral and cardiovascular disorders, impaired peripheral perfusion, edema formation such as, for example, pulmonary edema, brain edema, renal edema and heart failure-related edema, restenoses, for example after thrombolysis therapies, percutaneous transluminal angioplasties (PTA), transluminal coronary angioplasties (PTCA), heart transplants and bypass operations, for increased levels of fibrinogen and low-density LDL and also for increased concentrations of plasminogen activator inhibitor 1 (PAI-1), of dyslipidemias (hypercholesterolemia, hypertriglyceridemia, increased concentrations of postprandial plasma triglycerides, hypoalphalipoproteinemia, combined hyperlipidemias) and also metabolic disorders (metabolic syndrome, hyperglycemia, insulin-dependent diabetes, non-insulin-dependent diabetes, gestational diabetes, hyperinsulinemia, insulin resistance, glucose intolerance, adipositas and diabetic sequelae, such as retinopathy, nephropathy and neuropathy), neoplastic disorders (skin cancer, brain tumours, breast cancer, bone marrow tumours, leukaemias, liposarcomas, carcinomas of the gastrointestinal tract, the liver, the pancreas, the lungs, the kidneys, the urethra, the prostate and the genital tract and also malignant tumours of the lymphoproliferative system, such as, for example, Hodgkin's and non-Hodgkin's lymphoma), of disorders of the gastrointestinal tract and the abdomen (glossitis, gingivitis, periodontitis, oesophagitis, eosinophilic gastroenteritis, mastocytosis, Crohn's disease, colitis, proctitis, anus pruritis, diarrhoea, coeliac disease, hepatitis, hepatic fibrosis, cirrhosis of the liver, pancreatitis and cholecystitis), of disorders of the central nervous system and neurodegenerative disorders (stroke, Alzheimer's disease, Parkinson's disease, dementia, epilepsy, depressions, multiple sclerosis), immune disorders, thyroid disorders (hyperthyreosis), skin disorders (psoriasis, acne, eczema, neurodermitis, various forms of dermatitis, such as, for example, dermatitis abacribus, actinic dermatitis, allergic dermatitis, ammonia dermatitis, facticial dermatitis, autogenic dermatitis, atopic dermatitis, dermatitis calorica, dermatitis combustionis, dermatitis congelationis, dermatitis cosmetica, dermatitis escharotica, exfoliative dermatitis, dermatitis gangraenose, stasis dermatitis, dermatitis herpetiformis, lichenoid dermatitis, dermatitis linearis, dermatitis maligna, medicinal eruption dermatitis, dermatitis palmaris and plantaris, parasitic dermatitis, photoallergic contact dermatitis, phototoxic dermatitis, dermatitis pustularis, seborrhoeic dermatitis, sunburn, toxic dermatitis, Meleney's ulcer, dermatitis veneata, infectious dermatitis, pyrogenic dermatitis and perioral dermatitis, and also keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), viral diseases (caused by influenza, adeno and corona viruses, such as, for example, HPV, HCMV, HIV, SARS), of disorders of the skeletal bone and the joints and also the skeletal muscle (multifarious forms of arthritis, such as, for example, arthritis alcaptonurica, arthritis ankylosans, arthritis dysenterica, arthritis exsudativa, arthritis fungosa, arthritis gonorrhoica, arthritis mutilans, arthritis psoriatica, arthritis purulenta, arthritis rheumatica, arthritis serosa, arthritis syphilitica, arthritis tuberculosa, arthritis urica, arthritis villonodularis pigmentosa, atypical arthritis, haemophilic arthritis, juvenile chronic arthritis, rheumatoid arthritis and metastatic arthritis, furthermore Still syndrome, Felty syndrome, Sjörgen syndrome, Clutton syndrome, Poncet syndrome, Pott syndrome and Reiter syndrome, multifarious forms of arthropathias, such as, for example, arthropathie deformans, arthropathie neuropathica, arthropathie ovaripriva, arthropathie psoriatica and arthropathie tabica, systemic scleroses, multifarious forms of inflammatory myopathies, such as, for example, myopathie epidemica, myopathie fibrosa, myopathie myoglobinurica, myopathie ossificans, myopathie ossificans neurotica, myopathie ossificans progressiva multiplex, myopathie purulenta, myopathie rheumatica, myopathie trichinosa, myopathie tropica and myopathie typhosa, and also the Günther syndrome and the Münchmeyer syndrome), of inflammatory changes of the arteries (multifarious forms of arteritis, such as, for example, endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, such as, for example, cataract, cachexia, osteoporosis, gout, incontinence, lepra, Sezary syndrome and paraneoplastic syndrome, for rejection reactions after organ transplants and for wound healing and angiogenesis in particular in the case of chronic wounds.

By virtue of their property profile, the compounds according to the invention are suitable in particular for the treatment and/or prevention of pulmonary arterial hypertension (PAH) and other forms of pulmonary hypertension (PH), chronic obstructive lung disease (COPD), acute lung injury (ALI), acute respiratory distress syndrome (ARDS), bronchiectasia, bronchiolitis obliterans, pulmonary emphysema, alpha-1-antitrypsin deficiency (AATD), cystic fibrosis (CF), sepsis and systemic-inflammatory response syndrome (SIRS), multiple organ failure (MOF, MODS), inflammatory intestinal disorders (IBD, Crohn's disease, colitis), chronic bronchitis, asthma, rhinitis, rheumatoid arthritis, inflammatory skin and eye diseases, arterioscleroses and cancerous disorders.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides the use of the compounds according to the invention in a method for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

The compounds according to the invention can be employed alone or, if required, in combination with other active compounds. Accordingly, the present invention furthermore provides medicaments comprising at least one of the compounds according to the invention and one or more further active compounds, in particular for the treatment and/or prevention of the disorders mentioned above. Suitable active compounds for combinations are, by way of example and preferably:

compounds which inhibit the signal transduction cascade, for example and preferably from the group of the kinase inhibitors, in particular from the group of the tyrosine kinase and/or serine/threonine kinase inhibitors;

compounds which inhibit the degradation and remodelling of the extracellular matrix, for example and preferably inhibitors of matrix metalloproteases (MMPs), in particular inhibitors of stromelysin, collagenases, gelatinases and aggrecanases (here in particular of MMP-1, MMP-3, MMP-8, MMP-9, MMP-10, MMP-11 and MMP-13) and of metalloelastase (MMP-12);

compounds which block the binding of serotonin to its receptor, for example and preferably antagonists of the 5-HT$_{2b}$ receptor;

organic nitrates and NO donors, such as, for example, sodium nitroprusside, nitroglycerin, isosorbide mononitrate, isosorbide dinitrate, molsidomine or SIN-1, and also inhaled NO;

NO-independent but hem-dependent stimulators of soluble guanylate cyclase, such as, in particular, the compounds described in WO 00/06568, WO 00/06569, WO 02/42301 and WO 03/095451;

NO- and hem-independent activators of soluble guanylate cyclase, such as, in particular, the compounds described in WO 01/19355, WO 01/19776, WO 01/19778, WO 01/19780, WO 02/070462 and WO 02/070510;

prostacyclin analogs, such as, by way of example and preferably, iloprost, beraprost, treprostinil or epoprostenol;

compounds which inhibit soluble epoxide hydrolase (sEH), such as, for example, N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

compounds which influence the energy metabolism of the heart, such as, by way of example and preferably, etomoxir, dichloroacetate, ranolazine or trimetazidine;

compounds which inhibit the degradation of cyclic guanosine monophosphate (cGMP) and/or cyclic adenosine monophosphate (cAMP), such as, for example, inhibitors of phosphodiesterases (PDE) 1, 2, 3, 4 and/or 5, in particular PDE 5 inhibitors, such as sildenafil, vardenafil and tadalafil;

agents having a bronchodilatory effect, by way of example and preferably from the group of the beta-adrenergic receptor agonists, such as, in particular, albuterol, isoproterenol, metaproterenol, terbutalin, formoterol or salmeterol, or from the group of the anticholinergics, such as, in particular, ipratropium bromide;

agents having antiinflammatory action, by way of example and preferably from the group of the glucocorticoids, such as, in particular, prednisone, prednisolone, methylprednisolone, triamcinolone, dexamethasone, beclomethasone, betamethasone, flunisolide, budesonide or fluticasone;

agents having antithrombotic action, by way of example and preferably from the group of the platelet aggregation inhibitors, of anticoagulants or of profibrinolytic substances;

active compounds which lower blood pressure, by way of example and preferably from the group of the calcium antagonists, angiotensin AII antagonists, ACE inhibitors, vasopeptidase inhibitors, endothelin antagonists, renin inhibitors, alpha-receptor blockers, beta-receptor blockers, mineralocorticoid receptor antagonists, Rho kinase inhibitors and diuretics; and/or active ingredients which alter lipid metabolism, for example and preferably from the group of the thyroid receptor agonists, cholesterol synthesis inhibitors, such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile adsorbents, bile acid reabsorption inhibitors and lipoprotein(a) antagonists.

In a preferred embodiment of the invention, the compounds according to the invention are employed in combination with a kinase inhibitor such as by way of example and preferably bortezomib, canertinib, erlotinib, gefitinib, imatinib, lapatinib, lestaurtinib, lonafarnib, pegaptinib, pelitinib, semaxanib, sorafenib, sunitinib, tandutinib, tipifarnib, vatalanib, fasudil, lonidamine, leflunomide, BMS-3354825 or Y-27632.

In a preferred embodiment of the invention, the compounds according to the invention are employed in combination with a serotonin receptor antagonist such as, by way of example and preferably, PRX-08066.

Agents having an antithrombotic effect preferably mean compounds from the group of platelet aggregation inhibitors, of anticoagulants or of profibrinolytic substances.

In a preferred embodiment of the invention, the compounds according to the invention are administered in combination with a platelet aggregation inhibitor such as by way of example and preferably aspirin, clopidogrel, ticlopidine or dipyridamole.

In a preferred embodiment of the invention, the compounds according to the invention are administered in combination with a thrombin inhibitor such as by way of example and preferably ximelagatran, melagatran, bivalirudin or clexane.

In a preferred embodiment of the invention, the compounds according to the invention are administered in combination with a GPIIb/IIIa antagonist such as by way of example and preferably tirofiban or abciximab.

In a preferred embodiment of the invention, the compounds according to the invention are administered in combination with a factor Xa inhibitor such as by way of example and preferably rivaroxaban, DU-176b, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist such as by way of example and preferably coumarin.

Agents which lower blood pressure preferably mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, Rho kinase inhibitors, and diuretics.

In a preferred embodiment of the invention, the compounds according to the invention are administered in combination with a calcium antagonist such as by way of example and preferably nifedipine, amlodipine, verapamil or diltiazem.

In a preferred embodiment of the invention, the compounds according to the invention are administered in combination with an alpha-1 receptor blocker such as by way of example and preferably prazosin.

In a preferred embodiment of the invention, the compounds according to the invention are administered in combination with a beta-receptor blocker such as by way of example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist such as by way of example and preferably losartan, candesartan, valsartan, telmisartan or embusartan.

In a preferred embodiment of the invention, the compounds according to the invention are administered in combination with an ACE inhibitor such as by way of example and preferably enalapril, captopril, lisinopril, ramipril, delapril, fosinopril, quinopril, perindopril or trandopril.

In a preferred embodiment of the invention, the compounds according to the invention are administered in combination with an endothelin antagonist such as by way of example and preferably bosentan, darusentan, ambrisentan or sitaxsentan.

In a preferred embodiment of the invention, the compounds according to the invention are administered in combination with a renin inhibitor such as by way of example and preferably aliskiren, SPP-600 or SPP-800.

In a preferred embodiment of the invention, the compounds according to the invention are administered in combination with a mineralocorticoid receptor antagonist such as by way of example and preferably spironolactone or eplerenone.

In a preferred embodiment of the invention, the compounds according to the invention are administered in combination with a Rho kinase inhibitor such as by way of example and preferably fasudil, Y-27632, SLx-2119, BF-66851, BF-66852, BF-66853, KI-23095, SB-772077, GSK-269962A or BA-1049.

In a preferred embodiment of the invention, the compounds according to the invention are administered in combination with a diuretic such as by way of example and preferably furosemide.

Agents which alter lipid metabolism preferably mean compounds from the group of CETP inhibitors, thyroid receptor agonists, cholesterol synthesis inhibitors such as HMG-CoA reductase inhibitors or squalene synthesis inhibitors, of ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and lipoprotein(a) antagonists.

In a preferred embodiment of the invention, the compounds according to the invention are administered in combination with a CETP inhibitor such as by way of example and preferably torcetrapib (CP-529 414), JJT-705 or CETP vaccine (Avant).

In a preferred embodiment of the invention, the compounds according to the invention are administered in combination with a thyroid receptor agonist such as by way of example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins such as by way of example and preferably lovastatin, simvastatin, pravastatin, fluvastatin, atorvastatin, rosuvastatin, cerivastatin or pitavastatin.

In a preferred embodiment of the invention, the compounds according to the invention are administered in combination with a squalene synthesis inhibitor such as by way of example and preferably BMS-188494 or TAK-475.

In a preferred embodiment of the invention, the compounds according to the invention are administered in combination with an ACAT inhibitor such as by way of example and preferably avasimibe, melinamide, pactimibe, eflucimibe or SMP-797.

In a preferred embodiment of the invention, the compounds according to the invention are administered in combination with an MTP inhibitor such as by way of example and preferably implitapide, BMS-201038, R-103757 or JTT-130.

In a preferred embodiment of the invention, the compounds according to the invention are administered in combination with a PPAR-gamma agonist such as by way of example and preferably pioglitazone or rosiglitazone.

In a preferred embodiment of the invention, the compounds according to the invention are administered in combination with a PPAR-delta agonist such as by way of example and preferably GW-501516 or BAY 68-5042.

In a preferred embodiment of the invention, the compounds according to the invention are administered in combination with a cholesterol absorption inhibitor such as by way of example and preferably ezetimibe, tiqueside or pamaqueside.

In a preferred embodiment of the invention, the compounds according to the invention are administered in combination with a lipase inhibitor such as by way of example and preferably orlistat.

In a preferred embodiment of the invention, the compounds according to the invention are administered in combination with a polymeric bile acid adsorbent such as by way of example and preferably cholestyramine, colestipol, colesolvam, CholestaGel or colestimide.

In a preferred embodiment of the invention, the compounds according to the invention are administered in combination with a bile acid reabsorption inhibitor such as by way of example and preferably ASBT (=IBAT) inhibitors such as, for example, AZD-7806, S-8921, AK-105, BARI-1741, SC-435 or SC-635.

In a preferred embodiment of the invention, the compounds according to the invention are administered in combination with a lipoprotein(a) antagonist such as by way of example and preferably gemcabene calcium (CI-1027) or nicotinic acid.

The present invention further provides medicaments comprising at least one compound according to the invention, usually in combination with one or more inert, non-toxic, pharmaceutically suitable excipients, and their use for the purposes mentioned above.

The compounds according to the invention may have systemic and/or local effects. For this purpose, they can be administered in a suitable way such as, for example, by the oral, parenteral, pulmonary, nasal, sublingual, lingual, buccal, rectal, dermal, transdermal, conjunctival or otic route or as implant or stent.

The compounds according to the invention can be administered in administration forms suitable for these administration routes.

Suitable for oral administration are administration forms which function according to the prior art and deliver the compounds according to the invention rapidly and/or in a modified manner, and which contain the compounds of the invention in crystalline and/or amorphized and/or dissolved form, such as, for example, tablets (uncoated and coated tablets, for example having coatings which are resistant to gastric juice or are insoluble or dissolve with a delay and control the release of the compound of the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g inhalative, intramuscular, subcutaneous, intracutaneous, percutaneous, or intraperitoneal). Administration forms suitable for parenteral administration are, inter alia, preparations for injection and infusion in the form of solutions, suspensions, emulsions, lyophilizates or sterile powders.

Suitable for the other routes of administration are, for example, pharmaceutical forms for inhalation (inter alia powder inhalers, nebulizers, aerosols), nasal drops, solutions, sprays; tablets for lingual, sublingual or buccal administration, films/wafers or capsules, suppositories, preparations for the ears and eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

Oral or parenteral administration are preferred, especially oral and intravenous administration and administration by inhalation.

The compounds according to the invention can be converted into the stated administration forms. This can take place in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (e.g. antioxidants such as, for example, ascorbic acid), colorings (e.g. inorganic pigments such as, for example, iron oxides) and masking flavors and/or odors.

It has generally proved to be advantageous on parenteral administration to administer amounts of about 0.001 to 1 mg/kg, preferably about 0.01 to 0.5 mg/kg of body weight per day to achieve effective results. On oral administration, the dosage is about 0.01 to 100 mg/kg, preferably about 0.01 to 20 mg/kg, and very particularly preferably about 0.1 to 10 mg/kg of body weight.

It may nevertheless be necessary where appropriate to deviate from the stated amounts, in particular as a function of body weight, administration route, individual response to the active ingredient, type of preparation and time or interval over which administration takes place. Thus, in some cases it may be sufficient to make do with less than the aforementioned minimum amount, whereas in other cases the upper limit mentioned must be exceeded. Where relatively large amounts are administered, it may be advisable to distribute these in a plurality of single doses over the day.

The following exemplary embodiments illustrate the invention. The invention is not restricted to the examples.

The percentage data in the following tests and examples are, unless indicated otherwise, percentages by weight; parts are parts by weight. Solvent ratios, dilution ratios and concentration data of liquid/liquid solutions are based in each case on the volume.

A. Examples

Abbreviations abs. absolute
Ac acetyl
aq. aqueous, aqueous solution
calc. calculated
Boc tert-butoxycarbonyl
c concentration
cat. catalytic
CDI N,N'-carbonyldiimidazole
conc. concentrated
d day(s)
dist. distilled
DIEA N,N-diisopropylethylamine
DMAP 4-N,N-dimethylaminopyridine
DMF N,N-dimethylformamide
DMSO dimethyl sulfoxide
ee enantiomeric excess
ent enantiomerically pure, enantiomer
eq. equivalent(s)
ESI electrospray ionization (in MS)
Et ethyl
GC-MS gas chromatography-coupled mass spectrometry
Gly glycine
h hour(s)
HATU O-(7-azabenzotriazol-1-yl)-N,N,N',N'-tetramethyluronium hexafluorophosphate
HOAc acetic acid
HPLC high-pressure, high-performance liquid chromatography
HR-MS high resolution mass spectrometry
LC-MS liquid chromatography-coupled mass spectrometry
MCPBA meta-chloroperbenzoic acid
Me methyl
min minute(s)
m.p. melting point
MPLC medium-pressure liquid chromatography
MS mass spectrometry
MTBE methyl tert-butyl ether
NMM N-methylmorpholine
NMR nuclear magnetic resonance spectrometry
p para
Ph phenyl
quant. quantitative (in yield)
rac racemic, racemate
RT room temperature
$R_t$ retention time (in HPLC)
tBu tert-butyl
TFA trifluoroacetic acid
TFAA trifluoroacetic anhydride
THF tetrahydrofuran
TLC thin-layer chromatography
TsOH p-toluenesulfonic acid
UV ultraviolet spectrometry
v/v volume to volume ratio (of a solution)

HPLC, LC-MS and GC-MS Methods:

Method 1 (LC-MS):
MS instrument type: Micromass ZQ; HPLC instrument type: Waters Alliance 2795; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min-3.0 min-4.5 min 2 ml/min; oven: 50° C.; UV detection: 210 nm.

Method 2 (LC-MS):
MS instrument type: Micromass ZQ; HPLC instrument type: HP 1100 Series; UV DAD; column: Phenomenex Gemini 3μ 30 mm×3.0 mm; mobile phase A: 1 l of water+0.5 ml of 50% strength formic acid, mobile phase B: 1 l of acetonitrile+0.5 ml 50% strength formic acid; gradient: 0.0 min 90% A→2.5 min 30% A→3.0 mM 5% A→4.5 mM 5% A; flow rate: 0.0 mM 1 ml/min→2.5 min-3.0 min-4.5 min 2 ml/min; oven: 50° C.; UV detection: 210 nm.

Method 3 (LC-MS):
Instrument: Micromass Quattro LCZ with HPLC Agilent Series 1100; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 4 (LC-MS):
MS instrument type: Waters ZQ; HPLC instrument type: Waters Alliance 2795; column: Phenomenex Onyx Monolithic C18, 100 mm×3 mm; mobile phase A: 1 l of water+0.5 ml of 50% strength formic acid, mobile phase B: 1 l of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 5 (LC-MS):
Instrument: Micromass QuattroPremier with Waters UPLC Acquity; column: Thermo Hypersil GOLD 1.9μ 50 mm×1 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 6 (LC-MS):
Instrument: Micromass Platform LCZ with HPLC Agilent Series 1100; column: Thermo Hypersil GOLD 3μ 20 mm×4 mm; mobile phase A: 1 l of water+0.5 ml of 50% strength formic acid, mobile phase B: 1 l of acetonitrile+0.5 ml of 50% strength formic acid; gradient: 0.0 min 100% A→0.2 min 100% A→2.9 min 30% A→3.1 min 10% A→5.5 min 10% A; flow rate: 0.8 ml/min; oven: 50° C.; UV detection: 210 nm.

Method 7 (LC-MS):
MS instrument type: Micromass ZQ; HPLC instrument type: Waters Alliance 2795; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 8 (LC-MS):

Instrument: Micromass Quattro LCZ with HPLC Agilent Series 1100; column: Phenomenex Synergi 2.5μ MAX-RP 100A Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→0.1 min 90% A→3.0 min 5% A→4.0 min 5% A→4.1 min 90% A; flow rate: 2 ml/min; oven: 50° C.; UV detection: 208-400 nm.

Method 9 (LC-MS):

Instrument: Waters Acquity SQD UPLC System; column: Waters Acquity UPLC HSS T3 1.8μ 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.

Method 10 (HR-MS):

Instrument: Agilent 1100 HPLC system with LTQ Orbitrap mass spectrometer (Bremen, Germany) and an APCI ion source. The instrument is operated in the positive ion mode. For calibration, the mixture provided by the manufacturer is used: caffeine, L-methionylarginylphenylalanylalanine acetate (MRFA) and Ultramark 1621 in an acetonitrile/methanol/water solution with 1% acetic acide. The mass spectrometer is operated at a resolution of 60.000 (m/z=400) (full scan mode, Xcalibur 2.0 software; ThermoScientific, Bremen, Germany).

Method 11 (LC-MS):

Instrument: Micromass Quattro LCZ with HPLC Agilent Series 1100; column: Phenomenex Synergi 2μ Hydro-RP Mercury 20 mm×4 mm; mobile phase A: 1 l of water+0.5 ml of 50% strength formic acid, mobile phase B: 1 l of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min-3.0 min-4.5 min 2 ml/min; oven: 50° C.; UV detection: 208-400 nm.

Method 12 (GC-MS):

Instrument: Micromass GCT, GC 6890; column: Restek RTX-35, 15 m×200 μm×0.33 μm; constant helium flow: 0.88 ml/min; oven: 70° C.; inlet: 250° C.; gradient: 70° C., 30° C./min→310° C. (maintained for 3 min).

Starting Materials and Intermediates

Example 1A 4-(2-Cyano-3-oxobut-1-en-1-yl)benzonitrile

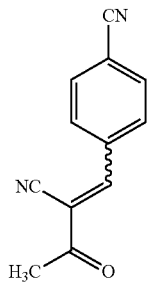

4-Cyanobenzaldehyde (360.0 g, 2.75 mol) and sodium 1-cyanoprop-1-en-2-olate (288.5 g, 2.75 mol, 1 eq.; for the preparation, cf. R. Troschütz, *Archiv der Pharmazie* 1984, 317, 709-713) were initially charged in dichloromethane (20 liters). Glacial acetic acid (196.5 ml, 3.43 mol, 1.25 eq.) and piperidine (27.2 ml, 0.274 mol, 0.1 eq.) were then added, and the mixture was heated under reflux on a water separator (18 h). The reaction solution was then washed with saturated sodium bicarbonate solution (5 liters), dried over sodium sulfate and concentrated on a rotary evaporator. The solid residue was triturated with six times the amount of ethanol and then filtered off with suction, and the crystals were washed with ethanol and dried under high vacuum. This gave 427 g (79% of theory) of the title compound.

LC-MS (Method 5): $R_t$=0.91 min; MS (ESIpos): m/z (%)=280.3 (100) [M+H]$^+$; MS (ESIneg): m/z (%)=197.3 (100), 278.3 (25) [M−H]$^-$.

$^1$H-NMR (400 MHz, DMSO-d$_6$): δ=8.05 (m, 2H), 8.15 (m, 2H), 8.45 (s, 1H) (signal of the methyl group obscured by the DMSO peak).

Example 2A (rac)-2-Amino-7-(4-cyanophenyl)-5-methyl-4,7-dihydro[1,2,4]triazolo[1,5-a]pyrimidine-6-carbonitrile

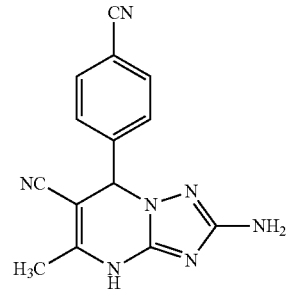 [SMILES: CC1=C(C#N)C(c2ccc(C#N)cc2)n2nc(N)nc2N1]

Under argon, 4-(2-cyano-3-oxobut-1-en-1-yl)benzonitrile (15.0 g, 76.45 mmol), 3,5-diaminotriazole (15.15 g, 152.90 mmol, 2.0 eq.), D,L-proline (7.04 g, 61.16 mmol, 0.8 eq.) and molecular sieve (4 Å, 5 g) were suspended in a mixture of dichloromethane (800 ml), pyridine (800 ml) and DMF (1600 ml), and the mixture was stirred for 3 d. More 3,5-diaminotriazole (4.0 g, 40.37 mmol, 0.5 eq.) and D,L-proline (4.0 g, 34.74 mmol, 0.45 eq.) were then added, and the mixture was stirred for another 5 d. The reaction mixture was then filtered and the filtrate concentrated under reduced pressure (intermediate 4-[2-cyano-1-(3,5-diamino-1H-1,2,4-triazol-1-yl)-3-oxobutyl]benzonitrile).

Toluene (500 ml), pyridine (300 ml) and 4-toluenesulfonic acid monohydrate (1.1 g, 5.78 mmol, 0.08 eq.) were then added to the intermediate and the mixture was heated under reflux (1 h). The reaction mixture was then filtered, the filtrate was concentrated under reduced pressure and the residue dried under high vacuum. Ethanol (300 ml) was added, the residue was suspended and stirred in an ultrasonic bath and the solid was then filtered off. The product was once more triturated with ethanol (300 ml), filtered off and finally dried under high vacuum. This gave 16.70 g (78% of theory) of the title compound.

LC-MS (Method 7): $R_t$=0.98 min; MS (ESIpos): m/z (%)=278.3 (100) [M+H]$^+$; MS (ESIneg): m/z (%)=276.4 (85) [M−H]$^-$.

$^1$H-NMR (400 MHz, DMSO-d$_6$): δ=2.15 (s, 3H), 5.35 (s, 2H), 6.05 (s, 1H), 7.45 (m, 2H), 7.85 (m, 2H), 10.95 (s, 1H).

Example 3A (rac)-7-(4-Cyanophenyl)-2-(1,3-dioxo-1,3-dihydro-2H-isoindol-2-yl)-5-methyl-4,7-dihydro[1,2,4]-triazolo[1,5-a]pyrimidine-6-carbonitrile

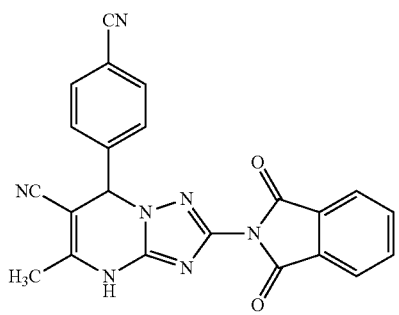 [SMILES: CC1=C(C#N)C(c2ccc(C#N)cc2)n2nc(N3C(=O)c4ccccc4C3=O)nc2N1]

Under argon, (rac)-2-amino-7-(4-cyanophenyl)-5-methyl-4,7-dihydro[1,2,4]triazolo[1,5-a]pyrimidine-6-carbonitrile (15 g, 54.1 mmol) together with phthalic anhydride (11.22 g, 75.7 mmol, 1.4 eq.) was suspended in a mixture of toluene (500 ml) and pyridine (600 ml), triethylamine (1.51 ml, 10.8 mmol, 0.2 eq.) was added and the mixture was heated under reflux overnight. More pyridine (200 ml), phthalic anhydride (8 g, 54.0 mmol, 1.0 eq.) and triethylamine (1.51 ml, 10.8 mmol, 0.2 eq.) were then added, and the mixture was heated under reflux for another 12 h. The reaction mixture was then concentrated under reduced pressure and the residue was dried under high vacuum (12 h). Three times, the crude product was suspended in ethanol (100 ml), stirred for 1 h, filtered off, washed with pentane and dried under high vacuum. The product obtained was a light-beige solid (20 g), which was recrystallised from DMF/methanol. To this end, the solid was initially dissolved in hot DMF (250 ml, 150° C.) and the cold DMF solution was then slowly, with stirring, poured into methanol (1.3 liters), whereupon the product precipitated out. The precipitate was filtered off and dried under high vacuum. Reprecipitation from DMF/methanol gave 15.91 g (99% pure, 71.5% of theory) of the title compound.

LC-MS (Method 5): $R_t$=0.98 min; MS (ESIpos): m/z (%)=408.2 (100) [M+H]$^+$; MS (ESIneg): m/z (%)=406.4 (100) [M−H]$^-$.

$^1$H-NMR (400 MHz, DMSO-d$_6$): δ=2.25 (s, 3H), 6.55 (s, 1H), 7.6 (m, 2H), 7.95 (br. m, 6H), 11.55 (s, 1H).

Example 4A

4-Methyl-3-(methylsulfanyl)benzonitrile

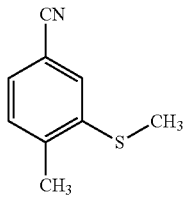

Method A:

The reaction was carried out under argon. 3-Fluoro-4-methylbenzonitrile (3000 mg, 22.2 mmol) and sodium methanethiolate (1572 mg, 20.2 mmol) were initially charged in DMF (30 ml), potassium carbonate (6973 mg, 50.5 mmol) was added and the mixture was stirred under reflux overnight. The reaction was then concentrated, the residue was suspended in methylene chloride/methanol (10:1) and the insoluble potassium carbonate present in the suspension was filtered off. The filtrate was reconcentrated and the residue chromatographed on silica gel (mobile phase: cyclohexane/ethyl acetate 10:1). This gave 2.51 g (64% of theory) of the desired compound.

Method B:

The reaction was carried out with the aid of a chlorine lye washer. 3-Fluoro-4-methylbenzonitrile (200 g, 1479.9 mmol) was initially charged in DMF (1.5 liters), the mixture was warmed to 40° C. and a little at a time (each portion about 25 g) sodium methanethiolate (126.8 g, 1627.9 mmol in total) was added. During the addition the temperature increased to 100° C. The reaction mixture was stirred initially at a bath temperature of 175° C. for 1.5 h and then at room temperature overnight. The reaction was then poured into water (7.5 liters) and extracted twice with ethyl acetate (1875 ml each). The combined organic phases were washed with saturated sodium chloride solution (1875 ml) and concentrated on a rotary evaporator, and the residue was chromatographed on silica gel (mobile phase: petroleum ether/ethyl acetate 95:5, about 30 liters). Removal of the solvent on a rotary evaporator and drying under high vacuum gave 172 g (71% of theory) of the desired compound.

GC-MS (Method 12): $R_t$=5.25 min; MS (ESIpos): m/z (%)=163.0 (100) [M]$^+$.

$^1$H-NMR (400 MHz, DMSO-d$_6$): δ=2.30 (s, 3H), 2.54 (s, 3H), 7.38 (d, 1H), 7.52 (dd, 1H), 7.58 (br. s, 1H).

Example 5A

4-Methyl-3-(methylsulfonyl)benzonitrile

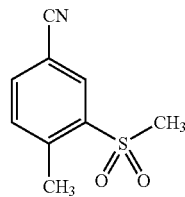

Method A:

4-Methyl-3-(methylsulfanyl)benzonitrile (14050 mg, 80.1 mmol) was dissolved in dichloromethane (700 ml), the mixture was cooled to 0° C. and 3-chloroperbenzoic acid (50923 mg, 206.6 mmol) was added slowly. The mixture was then stirred initially at 0° C. for 40 min and then at room temperature overnight. The precipitated 3-chlorobenzoic acid was filtered off, the filtrate was washed with 1 N aqueous sodium hydroxide solution and the organic phase was dried over sodium sulfate and concentrated. The residue was purified by silica gel chromatography (mobile phase: cyclohexane/ethyl acetate 1:1, 1:2). This gave 13.65 g (81% of theory) of the desired compound.

Method B:

3-Chloroperbenzoic acid (2501 g, 10144.4 mmol) was dissolved in 27.2 liters of dichloromethane, the mixture was cooled to 10° C. and 4-methyl-3-(methylsulfanyl)benzonitrile (552 g, 3381.5 mmol) was added a little at a time. After the addition had ended, the mixture was stirred at RT for 5 h.

The precipitated 3-chlorobenzoic acid was filtered off with suction and the solid was washed with dichloromethane (3 liters). The combined filtrates were stirred with 1 N aqueous sodium hydroxide solution (15 liters), the mixture was filtered and the organic phase was separated off. The latter was once more stirred with 1 N aqueous sodium hydroxide solution (15 liters), separated from the sodium hydroxide solution, dried and concentrated on a rotary evaporator. The residue was suspended in diethyl ether (4 liters), stirred for 10 min and then filtered. The solid was washed with a littel diethyl ether and dried under high vacuum. This gave 613 g (93% of theory) of the desired compound.

GC-MS (Method 12): $R_t$=6.59 min; MS (ESIpos): m/z (%)=195.0 (100) [M]$^+$.

$^1$H-NMR (400 MHz, DMSO-$d_6$): δ=2.30 (s, 3H), 2.54 (s, 3H), 7.38 (d, 1H), 7.52 (dd, 1H), 7.58 (br. s, 1H).

Example 6A

4-[2-(Dimethylamino)ethenyl]-3-(methylsulfonyl) benzonitrile

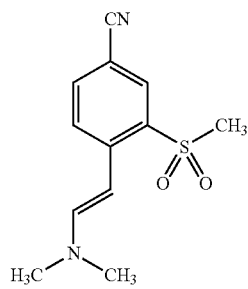

Method A:

The reaction was carried out under argon. 4-Methyl-3-(methylsulfonyl)benzonitrile (13.00 g, 66.6 mmol) and 1,1-dimethoxy-N,N-dimethylmethanamine (10.315 g, 86.6 mmol) were stirred in DMF (200 ml) at 140° C. for 14 h. To bring the reaction to completion, more 1,1-dimethoxy-N,N-dimethylmethanamine (3.967 g, 33.3 mmol) was then added and the mixture was stirred at 140° C. for another 24 h. The DMF was then removed on a rotary evaporator and without further purification the residue was reacted in the next step.

Method B:

The reaction was carried out under argon. 4-Methyl-3-(methylsulfonyl)benzonitrile (612 g, 3134.6 mmol) was initially charged in DMF (6.12 liters), 1,1-dimethoxy-N,N-dimethylmethanamine (859 g, 7209.5 mmol) was added and the mixture was stirred at 140° C. for 7 h. The reaction mixture was then poured into 35 liters of 10% strength sodium chloride solution and extracted twice with in each case 10 liters of ethyl acetate. The combined organic phases were washed with saturated sodium chloride solution (5 liters), dried and concentrated on a rotary evaporator, and the residue was dried under high vacuum overnight. This gave 1098 g (98% of theory) of the desired compound.

GC-MS (Method 12): $R_t$=8.95 min; MS (ESIpos): m/z (%)=250.0 (10) [M]$^+$.

Example 7A

4-Formyl-3-(methylsulfonyl)benzonitrile

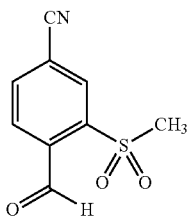

Method A:

4-[2-(Dimethylamino)ethenyl]-3-(methylsulfonyl)benzonitrile (16.666 g, 66.6 mmol) was initially charged in water/THF (1:1, 500 ml), sodium periodate (42.722 g, 199.7 mmol) was added and the mixture was stirred at room temperature overnight. The precipitated solid was filtered off and washed with ethyl acetate. The combined organic phases were washed with saturated sodium bicarbonate solution and saturated sodium chloride solution, dried over sodium sulfate, filtered and concentrated. The residue was purified by silica gel chromatography (mobile phase: cyclohexane/ethyl acetate 1:1). This gave 4.6 g (33% of theory) of the desired compound.

Method B:

4-[2-(Dimethylamino)ethenyl]-3-(methylsulfonyl)benzonitrile (1098 g, 3070.5 mmol) was initially charged in THF/water (1:1, 13.8 liters), sodium periodate (1970 g, 9211.4 mmol) was added and the mixture was stirred at room temperature for 1 h. The precipitated solid was filtered off with suction and washed with ethyl acetate (17 liters). Water (17 liters) was added to the combined filtrates, and after the extraction the aqueous phase was separated off. The organic phase was washed with saturated sodium bicarbonate solution (8.5 liters) and saturated sodium chloride solution (8.5 liters), then dried and concentrated on a rotary evaporator. Purification of the residue was carried out by silica gel chromatography (mobile phase: dichloromethane/ethyl acetate 9:1, 60 liters). The product fractions were concentrated, the residue was suspended in petroleum ether and then filtered off with suction and the solid was dried under high vacuum overnight. This gave 436 g (65% of theory) of the desired compound.

GC-MS (Method 12): $R_t$=6.89 min; MS (ESIpos): m/z (%)=191.1 (15) [M-18]$^+$, 161.0 (100).

$^1$H-NMR (400 MHz, DMSO-$d_6$): δ=3.57 (s, 3H), 8.10 (d, 1H), 8.39 (dd, 1H), 8.45 (d, 1H), 10.63 (s, 1H).

Example 8A 4-(2-Cyano-3-oxobut-1-en-1-yl)-3-(methylsulfonyl) benzonitrile

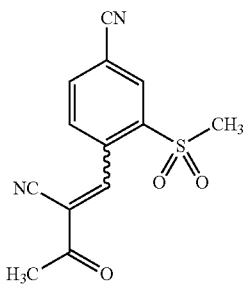 [SMILES: CC(=O)C(C#N)=Cc1ccc(C#N)cc1S(C)(=O)=O]

4-Formyl-3-(methylsulfonyl)benzonitrile (3.0 g, 14.34 mmol) and sodium 1-cyanoprop-1-en-2-oxide (1.66 g, 15.8 mmol, 1.1 eq.; cf. R. Troschtitz, *Archiv der Pharmazie* 1984, 317, 709-713) were initially charged in dichloromethane (180 ml). Glacial acetic acid (1.03 ml, 18 mmol, 1.25 eq.) and piperidine (142 µl, 1.43 mmol, 0.1 eq.) were then added, and the mixture was heated under reflux on a water separator (18 h). The reaction solution was then washed once with water (50 ml) and twice with saturated sodium bicarbonate solution (100 ml each), dried over sodium sulfate and concentrated. The solid residue was suspended in six times the amount of ethanol and once more filtered off with suction, and the crystals were washed with ethanol and dried under high vacuum. This gave 2.7 g (70% pure, 48% of theory) of the title compound.

LC-MS (Method 7): $R_t$=1.29 min; MS (ESIneg): m/z (%)=209.4 (100), 273.3 (45) [M−H]⁻.

$^1$H-NMR (400 MHz, DMSO-$d_6$): δ=2.55 (s, 3H), 3.4 (s, 3H), 8.05 (m, 1H), 8.4 (m, 1H), 8.5 (s, 1H), 8.9 (s, 1H).

Example 9A (rac)-2-Amino-7-[4-cyano-2-(methylsulfonyl)phenyl]-5-methyl-4,7-dihydro[1,2,4]triazolo[1,5-a]-pyrimidine-6-carbonitrile

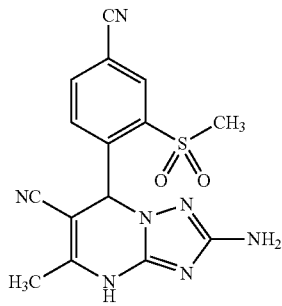 [SMILES: CC1=C(C#N)C(c2ccc(C#N)cc2S(C)(=O)=O)n2nc(N)nc2N1]

Under argon, 4-(2-cyano-3-oxobut-1-en-1-yl)-3-(methylsulfonyl)benzonitrile (1.0 g, 3.65 mmol), 3,5-diaminotriazole (1.08 g, 10.94 mmol, 3.0 eq.), D,L-proline (214 mg, 2.55 mmol, 0.7 eq.) and molecular sieve (4 Å, 0.5 g) were suspended in a mixture of pyridine (20 ml) and DMF (30 ml) and stirred for 3 d. More 3,5-diaminotriazole (361 mg, 3.64 mmol, 1 eq.) was added, and the mixture was stirred for a further 5 d. The reaction mixture was then filtered and the filtrate was concentrated under reduced pressure (intermediate 4-[2-cyano-1-(3,5-diamino-1H-1,2,4-triazol-1-yl)-3-oxobutyl]-3-(methylsulfonyl)benzonitrile).

Toluene (68 ml), pyridine (55 ml) and 4-toluenesulfonic acid monohydrate (100 mg, 0.53 mmol, 0.14 eq.) were added to the intermediate, and the mixture was heated under reflux (1 h). The reaction mixture was then concentrated under reduced pressure and the residue was dried under high vacuum. Ethanol (30 ml) was added, the residue was suspended and stirred in an ultrasonic bath and the solid was then filtered off and finally dried under high vacuum. This gave 673 mg (50% of theory) of the title compound.

LC-MS (Method 7): $R_t$=1.00 min; MS (ESIpos): m/z (%)=356.1 (100) [M+H]⁺; MS (ESIneg): m/z (%)=354.2 (100) [M−H]⁻.

$^1$H-NMR (400 MHz, DMSO-$d_6$): δ=2.15 (s, 3H), 3.55 (s, 3H), 5.40 (m, 2H), 7.05 (s, 1H), 7.75 (m, 1H), 8.25 (m, 1H), 8.35 (s, 1H), 11.05 (s, 1H).

Example 10A (rac)-7-[4-Cyano-2-(methylsulfonyl)phenyl]-2-(1,3-dioxo-1,3-dihydro-2H-isoindol-2-yl)-5-methyl-4,7-dihydro[1,2,4]triazolo[1,5-a]pyrimidine-6-carbonitrile

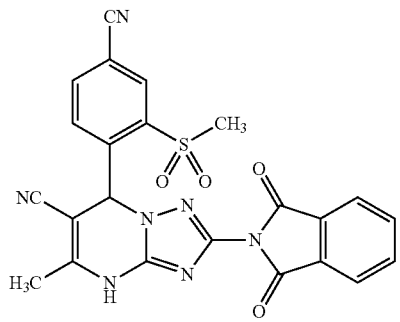 [SMILES: CC1=C(C#N)C(c2ccc(C#N)cc2S(C)(=O)=O)n2nc(N3C(=O)c4ccccc4C3=O)nc2N1]

Under argon, (rac)-2-amino-7-[4-cyano-2-(methylsulfonyl)phenyl]-5-methyl-4,7-dihydro[1,2,4]triazolo[1,5-a]pyrimidine-6-carbonitrile (60 mg, 0.17 mmol) together with phthalic anhydride (50.02 mg, 0.34 mmol, 2.0 eq.) was suspended in a mixture of toluene (4 ml) and pyridine (2 ml), triethylamine (4.7 µl, 0.034 mmol, 0.2 eq.) was added and the mixture was heated under reflux for 2 h. The reaction mixture was then concentrated under reduced pressure. From the residue, the product was precipitated by addition of ethanol (2 ml) in an ultrasonic bath. The precipitate was filtered off and dried under high vacuum. This gave 67 mg (75.6% of theory) of the title compound.

LC-MS (Method 5): $R_t$=0.97 min; MS (ESIpos): m/z (%)=486.0 (100) [M+H]⁺, 507.9 (30) [M+Na]⁺; MS (ESIneg): m/z (%)=484.4 (100) [M−H]⁻.

$^1$H-NMR (400 MHz, DMSO-$d_6$): δ=2.25 (s, 3H), 3.55 (s, 3H), 7.45 (s, 1H), 7.95 (m, 4H), 8.05 (m, 1H), 8.35 (m, 1H), 8.45 (s, 1H), 11.65 (s, 1H).

Example 11A

Ethyl 2-amino-7-(4-cyanophenyl)-5-methyl-4,7-dihydro[1,2,4]triazolo[1,5-a]pyrimidine-6-carboxylate

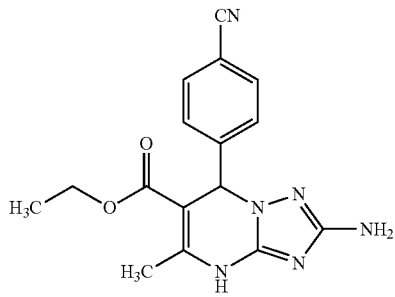 [SMILES: CCOC(=O)C1=C(C)Nc2nc(N)nn2C1c1ccc(C#N)cc1]

Under an atmosphere of argon, ethyl 2-(4-cyanobenzylidene)-3-oxobutanoate (12.2 g, 50.1 mmol; preparation see WO 2004/020410-A2, Example 32A) and 1H-1,2,4-triazole-3,5-diamine (6.0 g, 60.5 mmol, 1.2 eq.) were dissolved in DMF (150 ml). Solid sodium bicarbonate (30.7 g, 365.6 mmol, 6 eq.) was added, and the mixture was stirred at 63° C. for 12 h. The mixture was then filtered and the DMF was distilled off from the filtrate under reduced pressure. The residue was suspended in ethanol and stirred, and the product was then filtered off and dried under high vacuum. This gave 12.45 g (76% of theory) of the title compound.

LC-MS (Method 4): $R_t$=2.29 min; MS (ESIpos): m/z (%)=325.3 (100) [M+H]$^+$; MS (ESIneg): m/z (%)=323.3 (100) [M−H]$^−$.

$^1$H-NMR (400 MHz, DMSO-d$_6$): δ=1.00 (t, 3H), 2.40 (s, 3H), 3.95 (m, 2H), 5.25 (s, 2H), 6.05 (s, 1H), 7.35 (m, 2H), 7.75 (m, 2H), 10.6 (s, 1H).

Example 12A

Ethyl 7-(4-cyanophenyl)-2-(1,3-dioxo-1,3-dihydro-2H-isoindol-2-yl)-5-methyl-4,7-dihydro[1,2,4]-triazolo[1,5-a]pyrimidine-6-carboxylate

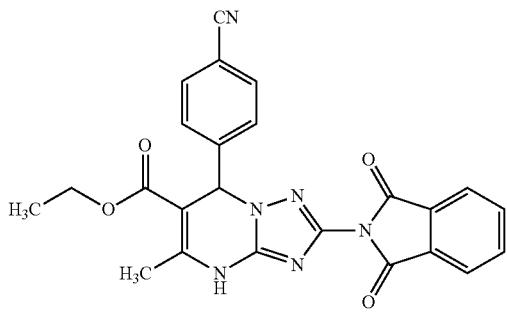 [SMILES: CCOC(=O)C1=C(C)Nc2nc(N3C(=O)c4ccccc4C3=O)nn2C1c1ccc(C#N)cc1]

Under argon, ethyl 2-amino-7-(4-cyanophenyl)-5-methyl-4,7-dihydro[1,2,4]triazolo[1,5-a]pyrimidine-6-carboxylate (5.0 g, 15.4 mmol) and phthalic anhydride (3.4 g, 23.1 mmol, 1.5 eq.) were dissolved in a mixture of toluene (400 ml) and pyridine (200 ml), triethylamine (42 μl, 0.3 mmol, 0.2 eq.) was added and the mixture was heated under reflux for 12 h. The reaction mixture was then concentrated under reduced pressure. The residue was taken up in ethyl acetate (600 ml) and extracted twice with saturated sodium bicarbonate solution (150 ml each). The organic phase was washed with saturated sodium chloride solution, dried over sodium sulfate and concentrated under reduced pressure. The crude product was suspended in ethanol (100 ml) and stirred for 12 h, and the solid was then filtered off and dried under high vacuum. This gave 6.67 g (95% of theory) of the title compound.

LC-MS (Method 4): $R_t$=3.11 min; MS (ESIpos): m/z (%)=455.2 (100) [M+H]$^+$; MS (ESIneg): m/z (%)=453.2 (100) [M−H]$^−$.

$^1$H-NMR (400 MHz, DMSO-d$_6$): δ=1.0 (t, 3H), 2.4 (s, 3H), 3.95 (m, 2H), 6.5 (s, 1H), 7.55 (m, 2H), 7.85 (m, 2H), 7.95 (m, 4H), 11.15 (s, 1H).

Example 13A

Ethyl (rac)-7-(4-cyanophenyl)-5-methyl-2-[(trifluoroacetyl)amino]-4,7-dihydro[1,2,4]triazolo[1,5-a]pyrimidine-6-carboxylate

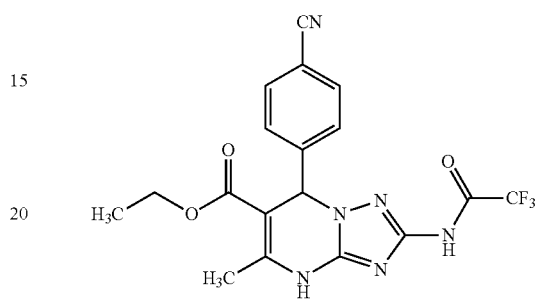

Under argon, ethyl 2-amino-7-(4-cyanophenyl)-5-methyl-4,7-dihydro[1,2,4]triazolo[1,5-a]pyrimidine-6-carboxylate (50 mg, 0.15 mmol) was dissolved in pyridine (1 ml), and trifluoroacetic anhydride (35 μl, 0.25 mmol, 1.6 eq.) was added. After 1 h of stirring, the solvent was distilled off under reduced pressure. The residue was purified by preparative HPLC (Gromsil C18 column, 30×250 mm; mobile phase: acetonitrile-water-0.1% TFA). After lyophilization, the product was obtained as a solid (60.6 mg, 93% of theory).

LC-MS (Method 4): $R_t$=3.02 min; MS (ESIpos): m/z (%)=421.3 (100) [M+H]$^+$; MS (ESIneg): m/z (%)=419.3 (100) [M−H]$^−$.

$^1$H-NMR (400 MHz, DMSO-d$_6$): δ=1.0 (t, 3H), 2.45 (s, 3H), 3.95 (m, 2H), 6.35 (s, 1H), 7.5 (m, 2H), 7.85 (m, 2H), 11.1 (s, 1H), 12.0 (s, 1H).

Example 14A

Benzyl 4-nitrophenyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}imidodicarbonate

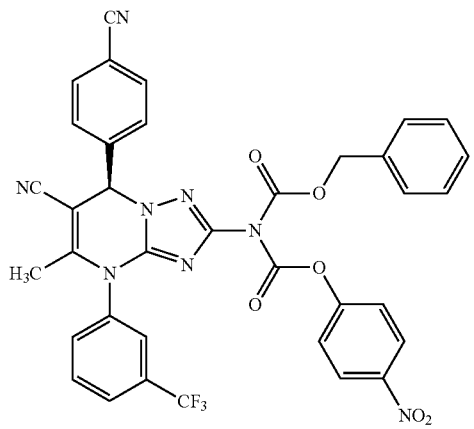 [SMILES: CC1=C(C#N)[C@@H](c2ccc(C#N)cc2)n2nc(N(C(=O)OCc3ccccc3)C(=O)Oc3ccc([N+](=O)[O-])cc3)nc2N1c1cccc(C(F)(F)F)c1]

Under an atmosphere of argon protective gas and at 0° C., 4-nitrophenyl chloroformate (27.2 mg, 135 μmol, 2.5 eq.), triethylamine (11.1 mg, 140 μmol, 2.6 eq.) and DMAP (0.7 mg, 5.4 μmol, 0.1 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (30 mg, 54 μmol; Example 38) in dry dichloromethane (2 ml), and the mixture was then stirred for 5 h. This reaction solution was used as such without further purification for subsequent reactions.

LC-MS (Method 7): $R_t$=2.50 min; MS (ESIpos): m/z (%)=721.4 (100) [M+H]$^+$; MS (ESIneg): m/z (%)=719.4 (100) [M−H]$^-$.

Example 15A (rac)-7-(4-Cyanophenyl)-2-(methoxymethyl)-5-methyl-4,7-dihydro[1,2,4]triazolo[1,5-a]pyrimidine-6-carbonitrile

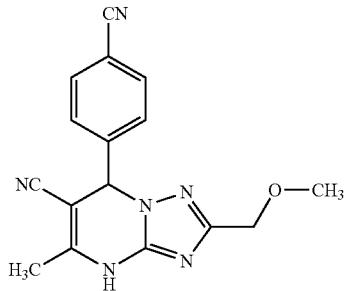

Under an atmosphere of argon, 3-(methoxymethyl)-1H-1,2,4-triazole-5-amine (244 mg, 1.9 mmol) and 4-(2-cyano-3-oxobut-1-en-1-yl)benzonitrile (300 mg, 1.5 mmol, 0.8 eq.) were dissolved in DMF (3 ml), and solid sodium bicarbonate (803 mg, 9.6 mmol, 5 eq.) was added. The mixture was stirred at 55° C. for 12 h. The mixture was then filtered, and the DMF from the filtrate was distilled off under reduced pressure. The residue was acidified with 1 N hydrochloric acid and then purified by preparative HPLC (Kromasil C18 column, 30×250 mm; mobile phase: acetonitrile-water-0.1% TFA). The product was obtained as a solid (38.2 mg, 80% pure, 7% of theory).

LC-MS (Method 2): $R_t$=2.18 min; MS (ESIpos): m/z (%)=307.0 (100) [M+H]$^+$; MS (ESIneg): m/z (%)=305.0 (100) [M−H]$^-$.

$^1$H-NMR (400 MHz, DMSO-d$_6$): δ=2.2 (s, 3H), 3.2 (s, 3H), 4.2 (s, 2H), 6.4 (s, 1H), 7.5 (m, 2H), 7.9 (m, 2H), 11.3 (s, 1H).

Example 16A (rac)-7-(4-Cyanophenyl)-5-methyl-2-thiophen-2-yl-4,7-dihydro[1,2,4]triazolo[1,5-a]pyrimidine-6-carbonitrile

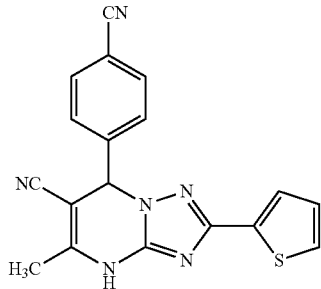 [SMILES: CC1=C(C#N)C(c2ccc(C#N)cc2)n2nc(-c3cccs3)nc2N1]

Under an atmosphere of argon, 3-(2-thienyl)-1H-1,2,4-triazole-5-amine (318 mg, 1.9 mmol) and 4-(2-cyano-3-oxobut-1-en-1-yl)benzonitrile (300 mg, 1.5 mmol, 0.8 eq.) were dissolved in DMF (3 ml), and solid sodium bicarbonate (803 mg, 9.6 mmol, 5 eq.) was added. The mixture was stirred at 55° C. for 12 h. The mixture was then filtered, and the DMF from the filtrate was distilled off under reduced pressure. The residue was purified by preparative HPLC (Kromasil C18 column, 30×250 mm; mobile phase: acetonitrile-water-0.1% TFA). The product was obtained as a solid (73.7 mg, 91% pure, 12% of theory).

LC-MS (Method 2): $R_t$=2.18 min; MS (ESIpos): m/z (%)=344.9 (100) [M+H]$^+$; MS (ESIneg): m/z (%)=343.0 (100) [M−H]$^-$.

$^1$H-NMR (400 MHz, DMSO-d$_6$): δ=2.2 (s, 3H), 6.45 (s, 1H), 7.1 (m, 1H), 7.5 (m, 1H), 7.55 (m, 2H), 7.6 (m, 1H), 7.9 (m, 2H), 11.4 (s, 1H).

Example 17A (rac)-Ethyl 7-(4-cyanophenyl)-5-methyl-4,7-dihydro[1,2,4]triazolo[1,5-a]pyrimidine-6-carboxylate

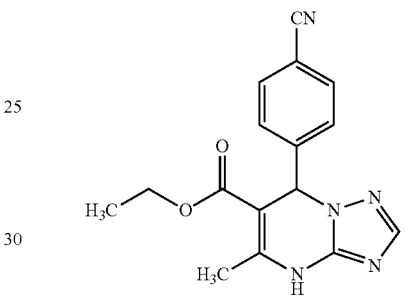

Under an atmosphere of argon, ethyl 2-(4-cyanobenzylidene)-3-oxobutanoate (300 mg, 1.2 mmol) and 1H-1,2,4-triazole-3-amine (130 mg, 1.5 mmol, 1.2 eq.) were dissolved in DMF (3 ml) and solid sodium bicarbonate (518 mg, 6.2 mmol, 5 eq.) was added. The mixture was stirred at 65° C. for 12 h. The mixture was then filtered, and the DMF from the filtrate was distilled off under reduced pressure. The residue was purified by preparative HPLC (Gromsil C18 column, 30×250 mm; mobile phase: acetonitrile-water-0.1% TFA). After lyophilization, the product was obtained as a solid (233 mg, 50% of theory).

LC-MS (Method 1): $R_t$=1.67 min; MS (ESIpos): m/z (%)=310.3 (100) [M+H]$^+$; MS (ESIneg): m/z (%)=308.3 (100) [M−H]$^-$.

$^1$H-NMR (400 MHz, DMSO-d$_6$): δ=1.0 (t, 3H), 2.45 (s, 3H), 3.95 (m, 2H), 6.35 (s, 1H), 7.45 (m, 2H), 7.7 (s, 1H), 7.8 (m, 2H) 10.95 (s, 1H).

Example 18A (rac)-Ethyl 7-(4-cyanophenyl)-2-methoxy-5-methyl-4,7-dihydro[1,2,4]triazolo[1,5-a]pyrimidine-6-carboxylate

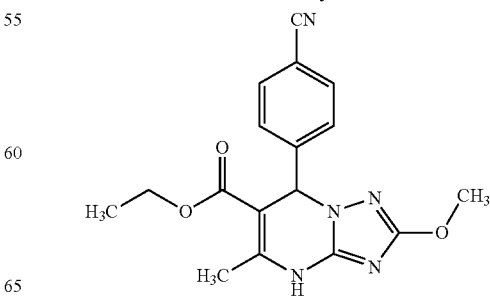

Under an atmosphere of argon, ethyl 2-(4-cyanobenzylidene)-3-oxobutanoate (297 mg, 1.2 mmol) and 5-methoxy-1H-1,2,4-triazole-3-amine (153 mg, 1.3 mmol, 1.1 eq.) were dissolved in DMF (2.5 ml), and solid sodium bicarbonate (513 mg, 6.1 mmol, 5 eq.) was added. The mixture was stirred at 65° C. for 12 h. The mixture was then filtered, and the DMF from the filtrate was distilled off under reduced pressure. The residue was purified by preparative HPLC (Gromsil C18 column, 30×250 mm; mobile phase: acetonitrile-water-0.1% TFA). After lyophilization, the product was obtained as a solid (191 mg, 42% of theory).

LC-MS (Method 1): $R_t$=1.77 min; MS (ESIpos): m/z (%)=340.3 (100) [M+H]$^+$; MS (ESIneg): m/z (%)=338.3 (100) [M–H]$^-$.

$^1$H-NMR (400 MHz, DMSO-d$_6$): δ=1.0 (t, 3H), 2.35 (s, 3H), 3.7 (s, 3H), 3.95 (m, 2H), 6.15 (s, 1H), 7.4 (m, 2H), 7.8 (m, 2H), 10.85 (s, 1H).

Example 19A (rac)-Diethyl 7-(4-cyanophenyl)-5-methyl-4,7-dihydro[1,2,4]triazolo[1,5-a]pyrimidine-2,6-dicarboxylate

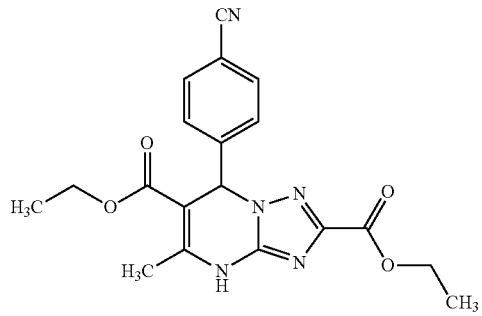 [SMILES: CCOC(=O)C1=C(C)Nc2nc(C(=O)OCC)nn2C1c1ccc(C#N)cc1]

Under an atmosphere of argon, ethyl 3-amino-1H-1,2,4-triazole-5-carboxylate (700 mg, 4.4 mmol) and ethyl 2-(4-cyanobenzylidene)-3-oxobutanoate (1.18 g, 4.9 mmol, 1.1 eq.) were dissolved in DMF (5 ml), and solid sodium bicarbonate (1.86 g, 22.1 mmol, 5 eq.) was added. The mixture was stirred at 55° C. for 6 h. The mixture was then filtered, and the DMF from the filtrate was distilled off under reduced pressure. The residue was purified by preparative HPLC (Gromsil C18 column, 30×250 mm; mobile phase: acetonitrile-water-0.1% TFA). After lyophilization, the product was obtained as a solid (1.3 g, 80% of theory).

LC-MS (Method 3): $R_t$=3.07 min; MS (ESIpos): m/z (%)=382.3 (100) [M+H]$^+$; MS (ESIneg): m/z (%)=380.2 (100) [M–H]$^-$.

$^1$H-NMR (400 MHz, DMSO-d$_6$): δ=1.0 (t, 3H), 1.25 (t, 3H), 2.45 (s, 3H), 3.95 (m, 2H), 4.25 (m, 2H), 6.45 (s, 1H), 7.5 (m, 2H), 7.8 (m, 2H), 11.1 (s, 1H).

Example 20A (rac)-Ethyl 7-(4-cyanophenyl)-2,5-dimethyl-4,7-dihydro[1,2,4]triazolo[1,5-a]pyrimidine-6-carboxylate

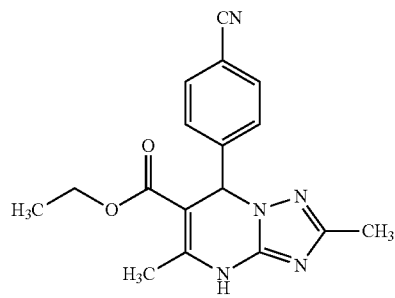 [SMILES: CCOC(=O)C1=C(C)Nc2nc(C)nn2C1c1ccc(C#N)cc1]

Under an atmosphere of argon, ethyl 2-(4-cyanobenzylidene)-3-oxobutanoate (381 mg, 1.6 mmol) and 5-methyl-4H-1,2,4-triazole-3-amine (200 mg, 2.0 mmol, 1.3 eq.) were dissolved in DMF (4 ml), and solid sodium bicarbonate (659 mg, 7.8 mmol, 5 eq.) was added. The mixture was stirred at 65° C. for 12 h. The mixture was then filtered, and the DMF from the filtrate was distilled off under reduced pressure. The residue was purified by preparative HPLC (Gromsil C18 column, 30×250 mm; mobile phase: acetonitrile-water-0.1% TFA). After lyophilization, the product was obtained as a solid (300 mg, 46% of theory).

LC-MS (Method 2): $R_t$=1.92 min; MS (ESIpos): m/z (%)=324.1 (100) [M+H]$^+$; MS (ESIneg): m/z (%)=322.1 (100) [M–H]$^-$.

$^1$H-NMR (400 MHz, DMSO-d$_6$): δ=1.0 (t, 3H), 2.1 (t, 3H), 2.4 (s, 3H), 3.4 (m, 2H), 6.25 (s, 1H), 7.4 (m, 2H), 7.8 (m, 2H), 10.75 (s, 1H).

Example 21A (rac)-7-(4-Cyanophenyl)-2-methoxy-5-methyl-4,7-dihydro[1,2,4]triazolo[1,5-a]pyrimidine-6-carbonitrile

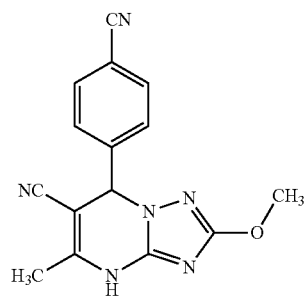

Under argon, 4-(2-cyano-3-oxobut-1-en-1-yl)benzonitrile (500 mg, 2.55 mmol), 3-methoxy-1H-1,2,4-triazole-5-amine (291 mg, 2.55 mmol, 1.0 eq.), D,L-proline (151 mg, 1.27 mmol, 0.5 eq.) and molecular sieve (4 Å, 0.5 g) were stirred in a mixture of pyridine (2 ml) and DMF (6 ml) (4 d). The solvents were then distilled off under reduced pressure and the residue was dried under high vacuum for 12 h (intermediate 4-[1-(5-amino-3-methoxy-1H-1,2,4-triazol-1-yl)-2-cyano-3-oxobutyl]benzonitrile).

Toluene (30 ml), pyridine (20 ml) and 4-toluenesulfonic acid monohydrate (31 mg, 161 μmol, 0.1 eq.) were added to the intermediate, and the mixture was heated under reflux (1 h). The reaction mixture was then filtered, the filtrate was concentrated under reduced pressure and the residue was dried under high vacuum Ethanol (10 ml) was added, the residue was suspended in an ultrasonic bath and stirred and the product was then filtered off. The product was once more triturated with ethanol (10 ml), filtered off and finally dried under high vacuum. This gave 179 mg (37% of theory) of the title compound.

LC-MS (Method 2): $R_t$=1.69 min; MS (ESIpos): m/z (%)=293.1 (100) [M+H]$^+$; MS (ESIneg): m/z (%)=291.2 (100) [M−H]$^−$.

$^1$H-NMR (400 MHz, DMSO-d$_6$): δ=2.15 (s, 3H), 3.7 (s, 3H), 6.2 (s, 1H), 7.5 (m, 2H), 7.9 (m, 2H), 11.25 (s, 1H).

Example 22A (rac)-Ethyl 6-(4-cyanophenyl)-8-methyl-6,9-dihydropyrimido[2,1-f]purine-7-carboxylate

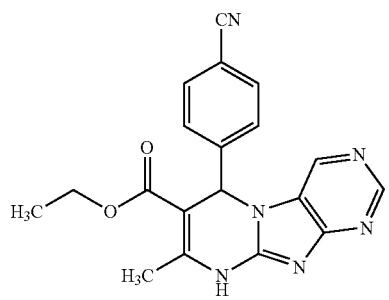 [SMILES: CCOC(=O)C1=C(C)Nc2nc3ncncc3n2C1c1ccc(C#N)cc1]

Under an atmosphere of argon, 7H-purine-8-amine (300 mg, 2.2 mmol) and ethyl 2-(4-cyanobenzylidene)-3-oxobutanoate (702 mg, 2.9 mmol, 1.3 eq.) were dissolved in DMF (5 ml), and solid sodium bicarbonate (932 mg, 11.1 mmol, 5 eq.) was added. The mixture was stirred at 55° C. for 12 h. The mixture was then filtered, and the DMF from the filtrate was distilled off under reduced pressure. The residue was purified by preparative HPLC (Gromsil C18 column, 30×250 mm; mobile phase: acetonitrile-water-0.1% TFA 10:90→90:10). After lyophilization of the appropriate fractions, the title compound was obtained as a solid (430 mg, 54% of theory). The isomeric compound (rac)-ethyl 9-(4-cyanophenyl)-7-methyl-6,9-dihydropyrimido[1,2-e]purine-8-carboxylate (see Example 23A) was obtained as a byproduct.

LC-MS (Method 2): $R_t$=1.72 min; MS (ESIpos): m/z (%)=361.1 (100) [M+H]$^+$; MS (ESIneg): m/z (%)=359.2 (100) [M−H]$^−$.

$^1$H-NMR (400 MHz, DMSO-d$_6$): δ=1.1 (t, 3H), 2.5 (s, 3H), 4.0 (m, 2H), 6.7 (s, 1H), 7.7 (m, 2H), 7.8 (m, 2H), 8.65 (s, 1H), 8.75 (s, 1H), 11.6 (s, 1H).

Example 23A (rac)-Ethyl 9-(4-cyanophenyl)-7-methyl-6,9-dihydropyrimido[1,2-e]purine-8-carboxylate

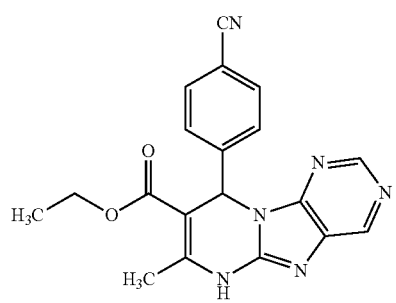 [SMILES: CCOC(=O)C1=C(C)Nc2nc3cncnc3n2C1c1ccc(C#N)cc1]

The title compound was obtained as a byproduct in the preparation of the compound from Example 22A and separated off during the HPLC purification described therein. After lyophilization of the appropriate fractions, 170 mg (21% of theory) were obtained as a solid.

LC-MS (Method 2): $R_t$=1.87 min; MS (ESIpos): m/z (%)=361.1 (100) [M+H]$^+$; MS (ESIneg): m/z (%)=359.2 (100) [M−H]$^−$.

$^1$H-NMR (400 MHz, DMSO-d$_6$): δ=1.0 (t, 3H), 2.5 (s, 3H), 4.0 (m, 2H), 6.55 (s, 1H), 7.55 (m, 2H), 7.75 (m, 2H), 8.65 (s, 1H), 8.75 (s, 1H), 11.3 (s, 1H).

Example 24A 7-(4-Cyanophenyl)-5-methyl-2-(propan-2-yl)-4,7-dihydro[1,2,4]triazolo[1,5-a]pyrimidine-6-carbonitrile

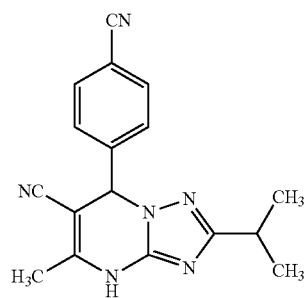 [SMILES: CC1=C(C#N)C(c2ccc(C#N)cc2)n2nc(C(C)C)nc2N1]

Under an atmosphere of argon, 3-isopropyl-1H-1,2,4-triazole-5-amine (241 mg, 1.9 mmol) and 4-(2-cyano-3-oxobut-1-en-1-yl)benzonitrile (300 mg, 1.5 mmol, 0.8 eq.) were dissolved in DMF (3 ml), and solid sodium bicarbonate (803 mg, 9.6 mmol, 5 eq.) was added. The mixture was stirred at 55° C. overnight. The mixture was then filtered and the DMF was distilled off from the filtrate under reduced pressure. The residue was suspended in methanol (2 ml), and the solid was then filtered off and dried under high vacuum (34 mg, 7% of theory). The filtrate was acidified with 1 N hydrochloric acid and purified by preparative HPLC (Kromasil C18 column, 30×250 mm; mobile phase: acetonitrile-water-0.1% TFA), which gave a second product fraction (67 mg, 13% of theory) as a solid.

LC-MS (Method 2): $R_t$=2.00 min; MS (ESIpos): m/z (%)=305.1 (100) [M+H]$^+$; MS (ESIneg): m/z (%)=303.2 (100) [M−H]$^-$.

$^1$H-NMR (400 MHz, DMSO-d$_6$): δ=1.15 (dd, 6H), 2.15 (s, 3H), 2.8 (m, 1H), 6.35 (s, 1H), 7.45 (m, 2H), 7.9 (m, 2H), 11.2 (s, 1H).

Example 25A

Ethyl (rac)-7-(4-cyanophenyl)-5-methyl-4,7-dihydrotetrazolo[1,5-a]pyrimidine-6-carboxylate

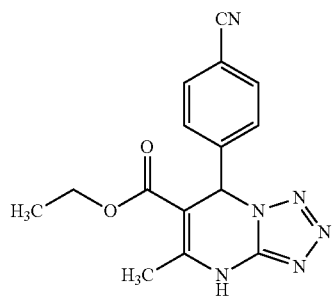 [SMILES: CCOC(=O)C1=C(C)Nc2nnnn2C1c1ccc(C#N)cc1]

Under an atmosphere of argon, 5-amino-1,2,3,4-tetrazole hydrate (1.0 g, 9.7 mmol) and ethyl 2-(4-cyanobenzylidene)-3-oxobutanoate (2.6 g, 10.7 mmol, 1.1 eq.) were dissolved in DMF (50 ml), and solid sodium bicarbonate (4.1 g, 48.5 mmol, 5 eq.) was added. The mixture was stirred at 55° C. for 12 h. The mixture was then filtered and the DMF from the filtrate was distilled off under reduced pressure. The residue was suspended in ethanol and stirred overnight. The product was filtered off and dried under high vacuum. This gave 950 mg (32% of theory) of the title compound.

LC-MS (Method 4): $R_t$=2.58 min; MS (ESIpos): m/z (%)=311.3 (100) [M+H]$^+$; MS (ESIneg): m/z (%)=309.3 (100) [M−H]$^-$.

$^1$H-NMR (400 MHz, DMSO-d$_6$): δ=1.00 (t, 3H), 3.30 (s, 3H), 3.95 (m, 2H), 6.80 (s, 1H), 7.50 (m, 2H), 7.85 (m, 2H), 11.40 (s, 1H).

Example 26A (rac)-4-(6-Acetyl-5-methyl-4,7-dihydrotetrazolo[1,5-a]pyrimidin-7-yl)benzonitrile

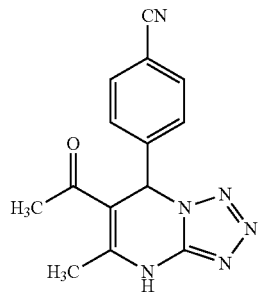 [SMILES: CC(=O)C1=C(C)Nc2nnnn2C1c1ccc(C#N)cc1]

Under an atmosphere of argon, 5-amino-1,2,3,4-tetrazole hydrate (300 mg, 2.9 mmol) and 4-(2-acetyl-3-oxobut-1-en-1-yl)benzonitrile (2.6 g, 10.7 mmol, 1.1 eq.; preparation see WO 2005/080372-A1, Example 4A) were dissolved in DMF (15 ml), and solid sodium bicarbonate (1.2 g, 14.5 mmol, 5 eq.) was added. The mixture was stirred at 62° C. overnight. The mixture was then filtered, and the DMF from the filtrate was distilled off under reduced pressure. The residue was acidified with 1 N hydrochloric acid and then purified by preparative HPLC (Gromsil C18 column, 30×250 mm; mobile phase: acetonitrile-water-0.1% TFA). The lyophilized product fraction was suspended in ethanol (2 ml), and the solid was then filtered off and dried under high vacuum. This gave 150 mg (18.4% of theory) of the title compound.

LC-MS (Method 4): $R_t$=1.79 min; MS (ESIpos): m/z (%)=281.3 (100) [M+H]$^+$; MS (ESIneg): m/z (%)=279.3 (100) [M−H]$^-$.

$^1$H-NMR (400 MHz, DMSO-d$_6$): δ=2.20 (s, 3H), 6.90 (s, 1H), 7.55 (m, 2H), 7.85 (m, 2H), 11.40 (s, 1H) (signal of a methyl group obscured by the DMSO peak).

Example 27A

Ethyl 5-(bromomethyl)-7-(4-cyanophenyl)-4-[3-(trifluoromethyl)phenyl]-4,7-dihydrotetrazolo-[1,5-a]pyrimidine-6-carboxylate

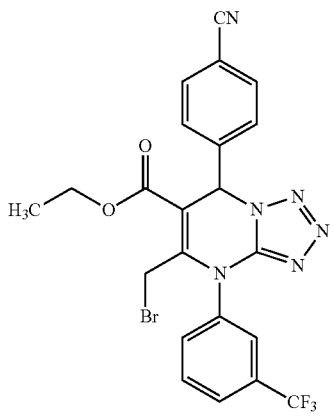 [SMILES: CCOC(=O)C1=C(CBr)N(c2cccc(C(F)(F)F)c2)c2nnnn2C1c1ccc(C#N)cc1]

Ethyl 7-(4-cyanophenyl)-5-methyl-4-[3-(trifluoromethyl)phenyl]-4,7-dihydrotetrazolo[1,5-a]pyrimidine-6-carboxylate (30 mg, 66.1 μmol; Example 70) was dissolved in chloroform (1 ml), and a solution of bromine (3×11.6 mg, 3×72.6 μmol, 3.3 eq.) in chloroform was added a little at a time at 0° C. The mixture was then stirred for 12 h, during which time it slowly warmed to RT. The mixture was then diluted with chloroform and washed with 10% strength sodium thiosulfate solution. The organic phase was separated off, dried over sodium sulfate and, after filtration, concentrated on a rotary evaporator. The crude product was reacted further without further purification (35.3 mg, 87% pure according to LC-MS, 87% of theory).

LC-MS (Method 4): $R_t$=3.78 min; MS (ESIpos): m/z (%)=535.1 (100) [M+H]$^+$.

Example 28A

Ethyl 5-(4-cyanophenyl)-7-methyl-5,8-dihydroimidazo[1,2-a]pyrimidine-6-carboxylate

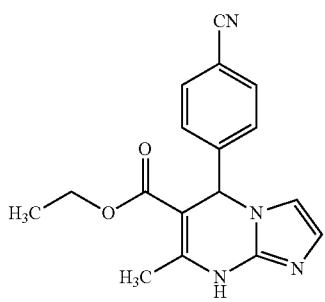 [SMILES: CCOC(=O)C1=C(C)Nc2nccn2C1c1ccc(C#N)cc1]

Under an atmosphere of argon, ethyl 2-(4-cyanobenzylidene)-3-oxobutanoate (1.42 g, 5.82 mmol) and 1H-imidazole-2-amine sulfate (2:1) (1000 mg, 3.78 mmol, 0.65 eq.) were dissolved in DMF (10 ml), and solid sodium bicarbonate (1.96 g, 23.3 mmol, 4 eq.) was added. The mixture was stirred at 65° C. for 12 h. The mixture was then filtered through kieselguhr, and the DMF from the filtrate was distilled off under reduced pressure. Acetonitrile (10 ml) was added to the residue. The precipitated product was filtered off, washed with ethanol and dried under high vacuum, which gave a first product fraction (503 mg). The concentrated filtrate was purified by preparative HPLC (Gromsil C18 column, 30×250 mm; mobile phase: acetonitrile-water-0.1% TFA) and lyophilized. This gave 778 mg as a further product fraction (total yield: 71% of theory).

LC-MS (Method 6): $R_t$=2.66 min; MS (ESIpos): m/z (%)=309.1 (100) [M+H]$^+$; MS (ESIneg): m/z (%)=307.1 (100) [M−H]$^−$.

$^1$H-NMR (400 MHz, DMSO-d$_6$): δ=1.05 (t, 3H), 2.44 (s, 3H), 4.0 (m, 2H), 6.40 (s, 1H), 7.05 (m, 2H), 7.55 (m, 2H), 7.85 (m, 2H), 11.45 (br. s, 1H).

Example 29A (7R)-6-Cyano-7-(4-cyanophenyl)-5-methyl-4-[3-(trifluoromethyl)phenyl]-4,7-dihydro[1,2,4]-triazolo[1,5-a]pyrimidine-2-sulfonyl chloride

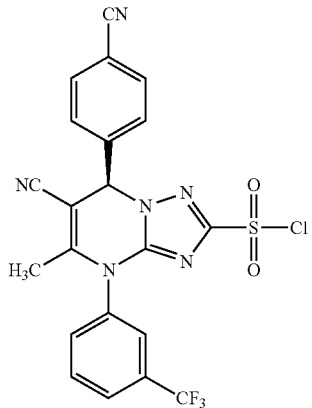 [SMILES: CC1=C(C#N)[C@@H](c2ccc(C#N)cc2)n2nc(S(=O)(=O)Cl)nc2N1c1cccc(C(F)(F)F)c1]

(7R)-2-Amino-7-(4-cyanophenyl)-5-methyl-4-[3-(trifluoromethyl)phenyl]-4,7-dihydro[1,2,4]triazolo[1,5-a]pyrimidine-6-carbonitrile (400 mg, 1.0 mmol; Example 7, free base) was dissolved in a mixture of acetic acid, conc. hydrochloric acid and water (2:1:1, 10 ml) at RT. At −10° C., a solution of sodium nitrite (72 mg, 1.0 mmol, 1.1 eq.) in water (1.1 ml) was slowly added dropwise to the reaction mixture. The mixture was allowed to warm to 0-2° C. and then cooled once more to −10° C. This solution was added to a solution of glacial acetic acid (11 ml) whose temperature had been adjusted to −10° C. beforehand and which had been saturated with sulfur dioxide gas and to which copper(I) chloride (18.8 mg, 0.019 mmol, 0.2 eq.) had been added. For a short while, there was a vigorous reaction. The mixture was stirred at −10° C. for 1 h, then warmed to 15° C. and stirred for another 1 h. The reaction solution was then once more cooled to 0° C. The product was precipitated by dropwise addition of this reaction solution to stirred ice-water (60 ml). The beige precipitate was filtered off, taken up in ethyl acetate, washed with saturated sodium chloride solution and then dried over sodium sulfate. After filtration, the mixture was concentrated under reduced pressure and the residue was dried under high vacuum. The product was obtained as a solid (415 mg, 63% pure, 55% of theory).

LC-MS (Method 5): $R_t$=1.39 min; MS (ESIpos): m/z (%)=505.1 (100) [M+H]$^+$; MS (ESIneg): m/z (%)=503.1 (90) [M−H]$^−$.

$^1$H-NMR (400 MHz, DMSO-d$_6$): δ=2.0 (s, 3H), 6.5 (s, 1H), 7.7-8.05 (m, 7H), 8.15 (br. s, 1H).

Example 30A (rac)-4-(4-Cyanophenyl)-6-methyl-2-thioxo-1-[3-(trifluoromethyl)phenyl]-1,2,3,4-tetrahydropyrimidine-5-carbonitrile

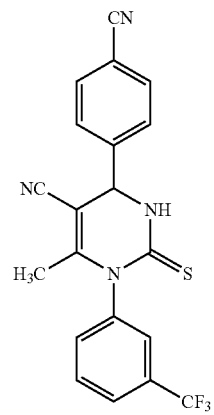 [SMILES: CC1=C(C#N)C(c2ccc(C#N)cc2)NC(=S)N1c1cccc(C(F)(F)F)c1]

Under an atmosphere of argon, triethyl phosphate (12.4 ml, 73.24 mmol, 8 eq.) was stirred together with diphosphorus pentoxide (6.94 g, 48.86 mmol, 5.4 eq.) at 50° C. for 4 h. Abs. THF (60 ml), 3-(trifluoromethyl)phenylthiourea (2.0 g, 9.08 mmol), 4-cyanobenzaldehyde (2.0 g, 15.26 mmol, 1.7 eq.) and acetamide (1.54 g, 15.26 mmol, 1.7 eq.) were then added, and the mixture was heated under reflux for 12 h. The reaction mixture was then concentrated under reduced pressure and the residue was directly purified by preparative HPLC (Gromsil C18 column, 30×250 mm; mobile phase: acetonitrile-water). After lyophilization, the title compound was obtained as a solid (680 mg, 18% of theory).

LC-MS (Method 5): $R_t$=1.27 min; MS (ESIpos): m/z (%)=399.2 (100) [M+H]$^+$; MS (ESIneg): m/z (%)=397.1 (20) [M−H]$^−$.

$^1$H-NMR (400 MHz, DMSO-d$_6$): δ=1.8 (s, 3H), 5.45 (s, 1H), 7.55-7.9 (m, 6H), 8.0 (m, 2H), 11.25 (br. m, 1H).

Example 31A (rac)-4-(4-Cyanophenyl)-2-hydrazinyl-6-methyl-1-[3-(trifluoromethyl)phenyl]-1,4-dihydropyrimidine-5-carbonitrile trifluoroacetate

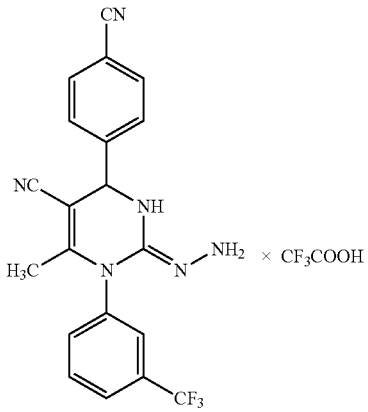 [SMILES: CC1=C(C#N)C(c2ccc(C#N)cc2)N/C(=N\N)N1c1cccc(C(F)(F)F)c1]

4-(4-Cyanophenyl)-6-methyl-2-thioxo-1-[3-(trifluoromethyl)phenyl]-1,2,3,4-tetrahydropyrimidine-5-carbonitrile (100 mg, 0.25 mmol) was dissolved in a mixture of ethanol (10 ml) and toluene (5 ml). At 0° C., tert-butyl hydroperoxide (3 M solution in toluene, 602 µl, 1.81 mmol, 7.2 eq.) was added dropwise. The mixture was stirred at RT for 3 h, and hydrazine hydrate (183 µl, 3.76 mmol, 15 eq.) was then added. After 12 h of stirring, more tert-butyl hydroperoxide solution (3 M in toluene, 167 µl, 0.50 mmol, 2 eq.) and hydrazine hydrate (49 µl, 1.00 mmol, 4 eq.) were added, and the mixture was stirred for a further 3 h. The mixture was then substantially concentrated under reduced pressure, water (2 ml) was added and the remaining organic solvents were distilled off. The aqueous residue was purified by preparative HPLC (Gromsil C18 column, 30×250 mm; mobile phase: acetonitrile-water-0.1% TFA). After lyophilization, the title compound was obtained as a solid (13.7 mg, 14% of theory).

LC-MS (Method 2): $R_t$=1.45 min; MS (ESIpos): m/z (%)=397.1 (100) [M+H]$^+$; MS (ESIneg): m/z (%)=395.2 (100) [M−H]$^−$.

$^1$H-NMR (400 MHz, DMSO-d$_6$): δ=1.8 (br. s, 3H), 5.6 (br. s, 1H), 7.55-7.95 (br. m, 7H), 8.0 (m, 2H), 8.15 (br. s, 1H), 9.3 (br. s, 1H).

Exemplary Embodiments

Example 1

Ethyl (rac)-7-(4-cyanophenyl)-2-(1,3-dioxo-1,3-dihydro-2H-isoindol-2-yl)-5-methyl-4-[3-(trifluoromethyl)phenyl]-4,7-dihydro[1,2,4]triazolo[1,5-a]pyrimidine-6-carboxylate

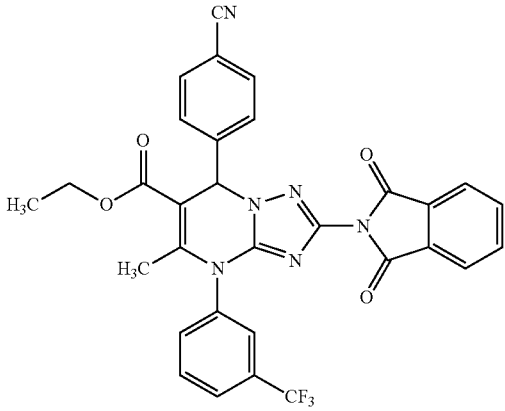 [SMILES: CCOC(=O)C1=C(C)N(c2cccc(C(F)(F)F)c2)c2nc(N3C(=O)c4ccccc4C3=O)nn2C1c1ccc(C#N)cc1]

Ethyl 7-(4-cyanophenyl)-2-(1,3-dioxo-1,3-dihydro-2H-isoindol-2-yl)-5-methyl-4,7-dihydro[1,2,4]-triazolo[1,5-a]pyrimidine-6-carboxylate (50 mg, 0.11 mmol), 3-(trifluoromethyl)phenylboronic acid (63 mg, 0.33 mmol, 3 eq.), anhydrous copper(II) acetate (60 mg, 0.33 mmol, 3 eq.) and molecular sieve (50 mg, 4 Å) were initially charged. Under an atmosphere of argon protective gas, abs. dichloromethane (2.5 ml), pyridine (71 µl, 0.88 mmol) and triethylamine (46 µl, 0.33 mmol, 3 eq.) were added. After 12 h of stirring, more 3-(trifluoromethyl)phenylboronic acid (21 mg, 0.11 mmol, 1 eq.), anhydrous copper(II) acetate (20 mg, 0.11 mmol, 1 eq.) and pyridine (36 µl, 0.44 mmol) were added. After a further 24 h of stirring, the mixture was filtered through kieselguhr, the residue was washed with dichloromethane and methanol and the filtrate was concentrated under reduced pressure. The residue was purified by preparative HPLC (Gromsil C18 column, 30×250 mm; mobile phase: acetonitrile-water-0.1% TFA). After lyophilization, the product was obtained as a solid (23.3 mg, 35% of theory).

LC-MS (Method 4): $R_t$=3.95 min; MS (ESIpos): m/z (%)=599.2 (100) [M+H]$^+$; MS (ESIneg): m/z (%)=597.3 (20) [M−H]$^−$.

$^1$H-NMR (400 MHz, DMSO-d$_6$): δ=1.0 (t, 3H), 2.2 (s, 3H), 4.0 (m, 2H), 6.6 (s, 1H), 7.80-8.05 (m, 11H), 8.25 (br. s, 1H).

Example 2

Ethyl (rac)-7-(4-cyanophenyl)-5-methyl-2-[(trifluoroacetyl)amino]-4-[3-(trifluoromethyl)phenyl]-4,7-dihydro[1,2,4]triazolo[1,5-a]pyrimidine-6-carboxylate

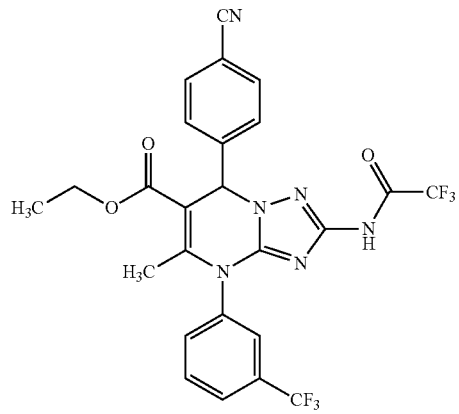 [SMILES: CCOC(=O)C1=C(C)N(c2cccc(C(F)(F)F)c2)c2nc(NC(=O)C(F)(F)F)nn2C1c1ccc(C#N)cc1]

Ethyl 7-(4-cyanophenyl)-5-methyl-2-[(trifluoroacetyl)amino]-4,7-dihydro[1,2,4]triazolo[1,5-a]pyrimidine-6-carboxylate (45 mg, 107 µmol) and 3-(trifluoromethyl)phenylboronic acid (61 mg, 321 µmol, 3 eq.) were initially charged together with anhydrous copper(II) acetate (58 mg, 321 µmol, 3 eq.) and molecular sieve (0.1 g, 4 Å) and, under an atmosphere of argon protective gas, suspended in abs. dichloromethane (3 ml). Abs. pyridine (69 µl, 856 µmol, 8 eq.) and triethylamine (45 µl, 321 µmol, 3 eq.) were then added. After 12 h of stirring, more 3-(trifluoromethyl)phenylboronic acid (20 mg, 107 µmol, 1 eq.), anhydrous copper(II) acetate (19 mg, 321 µmol, 1 eq.) and pyridine (35 µl, 428 µmol, 4 eq.) were added, and the mixture was stirred for a further 24 h. The mixture was then filtered through kieselguhr, the filter residue was washed with dichloromethan and methanol and the filtrate concentrated under reduced pressure. The residue was purified by preparative HPLC (Gromsil C18 column, 10 µm, 30×250 mm; mobile phase: acetonitrile-water-0.1% TFA). After lyophilization, the product was obtained as a solid (10.3 mg, 17% of theory).

LC-MS (Method 4): $R_t$=3.80 min; MS (ESIpos): m/z (%)=565.2 (100) [M+H]$^+$; MS (ESIneg): m/z (%)=563.2 (100) [M−H]$^-$.

$^1$H-NMR (400 MHz, DMSO-d$_6$): δ=1.05 (t, 3H), 2.2 (s, 3H), 4.0 (q, 2H), 6.5 (s, 1H), 7.7 (m, 2H), 7.75-8.00 (m, 5H), 8.2 (br. s, 1H), 12.05 (s, 1H).

Example 3

(rac)-7-[4-Cyanophenyl]-2-(1,3-dioxo-1,3-dihydro-2H-isoindol-2-yl)-5-methyl-4-[3-(trifluoromethyl)phenyl]-4,7-dihydro[1,2,4]triazolo[1,5-a]pyrimidine-6-carbonitrile

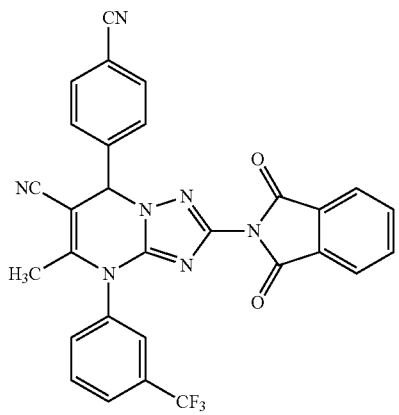 [SMILES: CC1=C(C#N)C(c2ccc(C#N)cc2)n2nc(N3C(=O)c4ccccc4C3=O)nc2N1c1cccc(C(F)(F)F)c1]

Under an atmosphere of argon protective gas, (rac)-7-[4-cyanophenyl]-2-(1,3-dioxo-1,3-dihydro-2H-isoindol-2-yl)-5-methyl-4,7-dihydro[1,2,4]triazolo[1,5-a]pyrimidine-6-carbonitrile (12 g, 29.5 mmol) was stirred in abs. dichloromethane (600 ml) with molecular sieve (20 g, 4 Å) for 1 h. 3-(Trifluoromethyl)phenylboronic acid (16.78 g, 88.4 mmol, 3 eq.) was added together with anhydrous copper(II) acetate (16.05 g, 88.4 mmol, 3 eq.). Abs. pyridine (400 ml) and triethylamine (12.32 ml, 88.4 mmol, 3 eq.) were then added. This mixture was stirred briefly (5 min), more abs. pyridine (440 ml) was then added and the mixture was stirred for 36 h. Since it was subsequently still possible to detect starting material (HPLC), 2,6-lutidine (3.43 ml, 29.6 mmol, 1 eq.) and a catalytic amount (spatula tip) of activated copper were added and the mixture was stirred under an atmosphere of dry air for a further 36 h. More 3-(trifluoromethyl)phenylboronic acid (5.59 g, 29.5 mmol, 1 eq.), anhydrous copper(II) acetate (5.35 g, 29.5 mmol, 1 eq.) and triethylamine (4.11 ml, 29.5 mmol, 1 eq.) were then metered in, and the mixture was then stirred for a further 5 d. The reaction mixture was then concentrated to dryness, and the residue was applied to silica gel using dichloromethane (~500 ml) and purified by flash chromatography (silica gel; mobile phase: cyclohexane/ethyl acetate 1:2). The product was obtained as a solid (3.07 g, 18.1% of theory).

LC-MS (Method 5): $R_t$=1.34 min; MS (ESIpos): m/z (%)=552.2 (100) [M+H]$^+$; MS (ESIneg): m/z (%)=550.1 (100) [M−H]$^-$.

$^1$H-NMR (400 MHz, DMSO-d$_6$): δ=2.05 (s, 3H), 6.65 (s, 1H), 7.80-8.05 (m, 11H), 8.25 (br. s, 1H).

Example 4

(7R)-7-(4-Cyanophenyl)-2-(1,3-dioxo-1,3-dihydro-2H-isoindol-2-yl)-5-methyl-4-[3-(trifluoromethyl)phenyl]-4,7-dihydro[1,2,4]triazolo[1,5-a]pyrimidine-6-carbonitrile

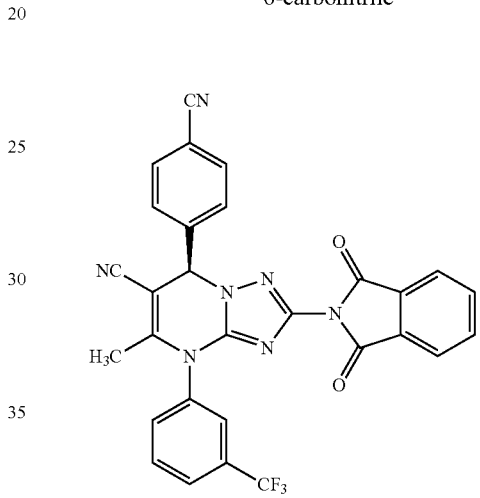

By preparative HPLC chromatography on a chiral phase, (rac)-7-(4-cyanophenyl)-2-(1,3-dioxo-1,3-dihydro-2H-isoindol-2-yl)-5-methyl-4-[3-(trifluoromethyl)phenyl]-4,7-dihydro[1,2,4]-triazolo[1,5-a]pyrimidine-6-carbonitrile (6.4 g) was separated into the enantiomers [stationary phase: chiral silica gel phase based on the selector poly(N-methacryloyl-L-isoleucine-3-pentylamide), 430×40 mm; sample preparation: solution in 192 ml of ethyl acetate/isohexane 1:1; flow: 50 ml/min; detection: 260 nm; injektion volume: 5 ml; temperature: 24° C.; mobile phase: ethyl acetate/isohexane 1:1]. The title compound was obtained as a solid (3.2 g, 100% of theory). The enantiomeric excess (ee) was determined chromatographically [column: chiral silica gel phase based on the selector poly(N-methacryloyl-L-isoleucine-3-pentylamide), 250 mm×4.6 mm; mobile phase: ethyl acetate/isohexane 1:1; flow: 2 ml/min; temperature: 24° C.; detection: 265 nm; $R_t$=2.11 min; ee>99.5%].

LC-MS (Method 2): $R_t$=2.63 min; MS (ESIpos): m/z (%)=552.2 (100) [M+H]$^+$; MS (ESIneg): m/z (%)=550.2 (100) [M−H]$^-$.

$^1$H-NMR (400 MHz, DMSO-d$_6$): δ=2.00 (s, 3H), 6.65 (s, 1H), 7.80-8.00 (m, 11H), 8.25 (br. s, 1H).

Example 5

(rac)-7-[4-Cyano-2-(methylsulfonyl)phenyl]-2-(1,3-dioxo-1,3-dihydro-2H-isoindol-2-yl)-5-methyl-4-[3-(trifluoromethyl)phenyl]-4,7-dihydro[1,2,4]triazolo[1,5-a]pyrimidine-6-carbonitrile

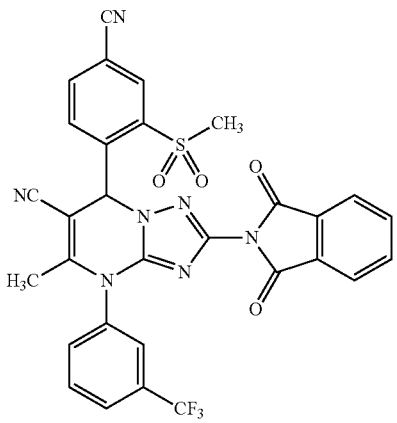 [SMILES: CC1=C(C#N)C(c2ccc(C#N)cc2S(C)(=O)=O)n2nc(N3C(=O)c4ccccc4C3=O)nc2N1c1cccc(C(F)(F)F)c1]

Under an atmosphere of argon protective gas, (rac)-7-[4-cyano-2-(methylsulfonyl)phenyl]-2-(1,3-dioxo-1,3-dihydro-2H-isoindol-2-yl)-5-methyl-4,7-dihydro[1,2,4]triazolo[1,5-a]pyrimidine-6-carbonitrile (600 mg, 1.2 mmol) was stirred in abs. dichloromethane (50 ml) with molecular sieve (0.5 g, 4 Å) for 15 min 3-(Trifluoromethyl)phenylboronic acid (704 mg, 3.7 mmol, 3 eq.) was added together with anhydrous copper(II) acetate (673 mg, 3.7 mmol, 3 eq.). Abs. pyridine (60 ml) and triethylamine (571 µl, 3.7 mmol, 3 eq.) were then added, and the mixture was stirred for 12 h. 2,6-Lutidine (864 µl, 7.4 mmol, 6 eq.) was then added, and the reaction mixture initially stirred under an atmosphere of dry air for 12 h and then left under an atmosphere of argon for 3 d. More 3-(trifluoromethyl)phenylboronic acid (235 mg, 1.2 mmol, 1 eq.), anhydrous copper(II) acetate (225 mg, 1.2 mmol, 1 eq.), 2,6-lutidine (432 µl, 3.7 mmol, 3 eq.) and a catalytic amount (spatula tip) of activated copper were then added, and the mixture was stirred under an atmosphere of dry air for 5 d. The reaction mixture was then concentrated to dryness, and the residue was applied to silica gel using dichloromethane (~50 ml) to silica gel and purified by flash chromatography (silica gel; mobile phase: cyclohexane/ethyl acetate 1:2). The product was obtained as a solid (102 mg, 13.1% of theory).

LC-MS (Method 2): $R_t$=2.56 min; MS (ESIpos): m/z (%)=630.0 (100) [M+H]$^+$; MS (ESIneg): m/z (%)=628.0 (100) [M−H]$^−$.

Example 6

(7S)-7-[4-Cyano-2-(methylsulfonyl)phenyl]-2-(1,3-dioxo-1,3-dihydro-2H-isoindol-2-yl)-5-methyl-4-[3-(trifluoromethyl)phenyl]-4,7-dihydro[1,2,4]triazolo[1,5-a]pyrimidine-6-carbonitrile

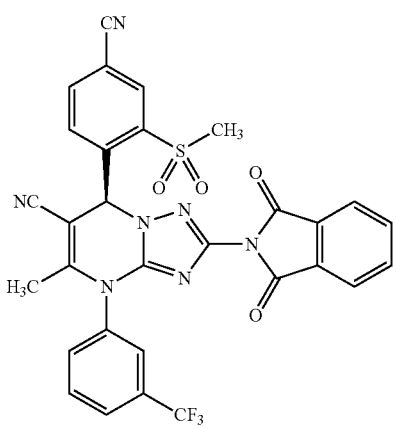

By preparative HPLC chromatography on a chiral phase, (rac)-7-[4-cyano-2-(methylsulfonyl)phenyl]-2-(1,3-dioxo-1,3-dihydro-2H-isoindol-2-yl)-5-methyl-4-[3-(trifluoromethyl)phenyl]-4,7-dihydro[1,2,4]triazolo[1,5-a]pyrimidine-6-carbonitrile (100 mg) was separated into the enantiomers [stationary phase: chiral silica gel phase based on the selector poly(N-methacryloyl-L-isoleucine-3-pentylamide), 250×20 mm; sample preparation: solution in 10 ml ethyl acetate; flow: 25 ml/min; detection: 260 nm; injection volume: 0.5 ml; temperature: 24° C.; mobile phase: ethyl acetate/isohexane 1:3]. The title compound was obtained as a solid (43 mg, 86% of theory). The enantiomeric excess (ee) was determined chromatographically [column: chiral silica gel phase based on the selector poly(N-methacryloyl-L-isoleucine-3-pentylamide), 250 mm×4.6 mm; mobile phase: ethyl acetate/isohexane 1:3; flow: 2 ml/min; temperature: 24° C.; detection: 265 nm; $R_t$=11.19 min; ee>99.5%].

For further analytical data see the racemic compound (Example 5).

Example 7

(7R)-2-Amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride

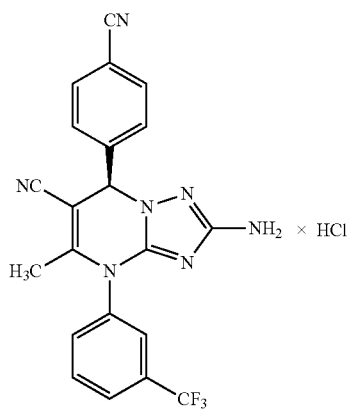 [SMILES: CC1=C(C#N)[C@@H](c2ccc(C#N)cc2)n2nc(N)nc2N1c1cccc(C(F)(F)F)c1]

Under an atmosphere of argon protective gas, (7R)-7-(4-cyanophenyl)-2-(1,3-dioxo-1,3-dihydro-2H-isoindol-2-yl)-5-methyl-4-[3-(trifluoromethyl)phenyl]-4,7-dihydro[1,2,4]triazolo[1,5-a]pyrimidine-6-carbonitrile (1.39 g, 2.5 mmol) was initially charged in abs. ethanol (35 ml). Hydrazine hydrate (208 µl, 4.3 mmol, 1.7 eq.) was added, and the mixture was heated at 85° C. for 1 h. The reaction mixture was concentrated, and the residue was dissolved in DMF (30 ml) and 1 N hydrochloric acid (5 ml) and then purified by preparative HPLC (Gromsil C18 column, 30×200 mm; mobile phase: acetonitrile-water-0.1% TFA). After lyophilization, the free base of the title compound was obtained as a solid (1.03 g, 97% of theory). The lyophilizate was taken up in a solution of hydrogen chloride in dioxane (4 N, 20 ml) and once more concentrated to dryness. This step was repeated once more. The residue was suspended in water (25 ml) and acetonitrile (5 ml) and lyophilized again.

LC-MS (Method 2): $R_t$=2.20 min; MS (ESIpos): m/z (%)=422.1 (100) [M+H]$^+$; MS (ESIneg): m/z (%)=420.1 (100) [M−H]$^−$.

$^1$H-NMR (400 MHz, DMSO-d$_6$): δ=1.95 (s, 3H), 5.45 (s, 2H), 6.20 (s, 1H), 7.70-7.95 (m, 7H), 8.15 (br. s, 1H).

Example 8

(rac)-2-Amino-7-[4-cyano-2-(methylsulfonyl)phenyl]-5-methyl-4-[3-(trifluoromethyl)phenyl]-4,7-dihydro[1,2,4]triazolo[1,5-a]pyrimidine-6-carbonitrile

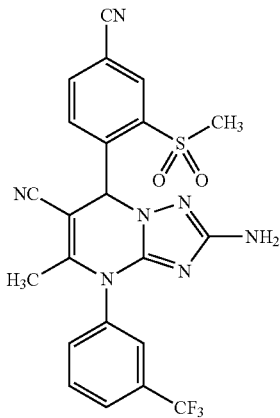 [SMILES: CC1=C(C#N)C(c2ccc(C#N)cc2S(C)(=O)=O)n2nc(N)nc2N1c1cccc(C(F)(F)F)c1]

In a pressure-proof glass tube, (rac)-7-[4-cyano-2-(methylsulfonyl)phenyl]-2-(1,3-dioxo-1,3-dihydro-2H-isoindol-2-yl)-5-methyl-4-[3-(trifluoromethyl)phenyl]-4,7-dihydro[1,2,4]triazolo[1,5-a]pyrimidine-6-carbonitrile (10 mg, 16 µmol) was initially charged in abs. ethanol (3 ml). Hydrazine hydrate (1.3 µl, 27 µmol, 1.7 eq.) was added, and the mixture was heated at 85° C. for 1 h. The reaction mixture was concentrated under reduced pressure, the residue was taken up in DMF (1 ml), 1 N hydrochloric acid (32 µl, 2 eq.) was added and the product was purified by preparative HPLC (Reprosil C18 column, 10 µm, 30×250 mm; mobile phase: acetonitrile-water-0.1% TFA). After lyophilization, the product was obtained as a solid (7.9 mg, quant.).

LC-MS (Method 5): $R_t$=1.11 min; MS (ESIpos): m/z (%)=500.1 (100) [M+H]$^+$; MS (ESIneg): m/z (%)=498.4 (100) [M-H]$^-$.

Example 9

(7S)-2-Amino-7-[4-cyano-2-(methylsulfonyl)phenyl]-5-methyl-4-[3-(trifluoromethyl)phenyl]-4,7-dihydro[1,2,4]triazolo[1,5-a]pyrimidine-6-carbonitrile hydrochloride

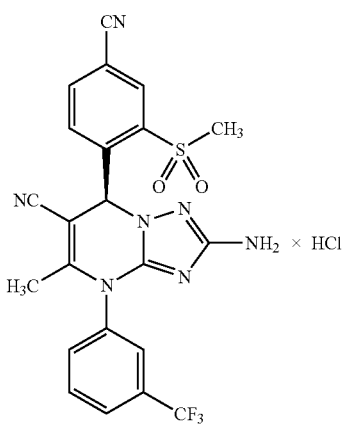 [SMILES: CC1=C(C#N)[C@@H](c2ccc(C#N)cc2S(C)(=O)=O)n2nc(N)nc2N1c1cccc(C(F)(F)F)c1]

Under an atmosphere of argon protective gas, (7S)-7-[4-cyano-2-(methylsulfonyl)phenyl]-2-(1,3-dioxo-1,3-dihydro-2H-isoindol-2-yl)-5-methyl-4-[3-(trifluoromethyl)phenyl]-4,7-dihydro[1,2,4]-triazolo[1,5-a]pyrimidine-6-carbonitrile (45 mg, 71.5 µmol) was initially charged in abs. ethanol (2.5 ml). Hydrazine hydrate (6 µl, 121.5 mmol, 1.7 eq.) was added, and the mixture was heated at 85° C. for 1 h. The reaction mixture was concentrated, and the residue was dissolved in DMF (1 ml) and 1 N hydrochloric acid (0.143 ml) and then purified by preparative HPLC (Reprosil C18 column, 30×250 mm; mobile phase: acetonitrile-water-0.1% TFA). After lyophilization, the free base of the title compound was obtained as a solid (30 mg, 84% of theory). The lyophilizate was taken up in a solution of hydrogen chloride in dioxane (4 N, 2 ml) and once more concentrated to dryness. This step was repeated once more. The residue was suspended in water (2 ml) and acetonitrile (0.5 ml) and lyophilized again.

LC-MS (Method 5): $R_t$=1.12 min; MS (ESIpos): m/z (%)=500.0 (100) [M+H]$^+$; MS (ESIneg): m/z (%)=498.7 (100) [M-H]$^-$.

$^1$H-NMR (400 MHz, DMSO-d$_6$): δ=2.0 (s, 3H), 3.6 (s, 3H), 5.55 (br. s, 2H), 7.20 (s, 1H), 7.70-8.45 (m, 7H).

Example 10

Benzyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}(methylsulfonyl)carbamate

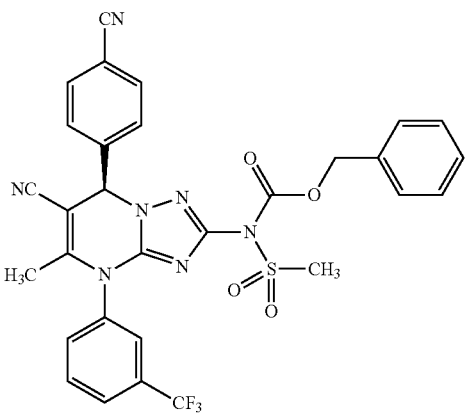 [SMILES: CC1=C(C#N)[C@@H](c2ccc(C#N)cc2)n2nc(N(C(=O)OCc3ccccc3)S(C)(=O)=O)nc2N1c1cccc(C(F)(F)F)c1]

Under an atmosphere of argon protective gas and at room temperature, triethylamine (11.1 mg, 140 µmol, 2.6 eq.) and methanesulfonyl chloride (41 mg, 360 µmol, 10 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (20 mg, 36 µmol; Example 38) in dry pyridine (2 ml) and THF (2 ml), and the mixture was stirred for 12 h. The reaction mixture was then concentrated under reduced pressure and directly purified by preparative HPLC (Reprosil C18 column, 30×200 mm; mobile phase: acetonitrile-water-0.1% TFA). After lyophilization, the product was obtained as a solid (17.4 mg, 72% of theory).

LC-MS (Method 2): $R_t$=2.71 min; MS (ESIpos): m/z (%)=634.2 (100) [M+H]$^+$; MS (ESIneg): m/z (%)=632.2 (100) [M-H]$^-$.

$^1$H-NMR (400 MHz, DMSO-d$_6$): δ=1.95 (s, 3H), 3.40 (s, 3H), 5.15 (d, 1H), 5.25 (d, 1H), 6.55 (s, 1H), 7.15 (m, 2H), 7.35 (m, 4H), 7.65 (m, 1H), 7.80-7.95 (m, 5H), 8.15 (br. s, 1H).

Example 11

2-({7-(4-Cyanophenyl)-6-(ethoxycarbonyl)-5-methyl-4-[3-(trifluoromethyl)phenyl]-4,7-dihydro-[1,2,4]triazolo[1,5-a]pyrimidin-2-yl}carbamoyl)benzoic acid

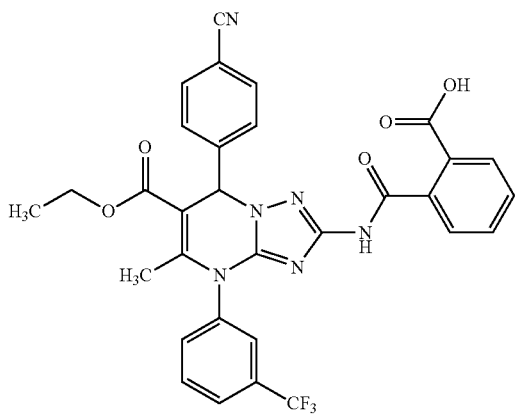 [SMILES: CCOC(=O)C1=C(C)N(c2cccc(C(F)(F)F)c2)c2nc(NC(=O)c3ccccc3C(=O)O)nn2C1c1ccc(C#N)cc1]

Water (1 ml) and potassium carbonate (23.1 mg, 167 µmol, 2 eq.) were added to a solution of ethyl 7-(4-cyanophenyl)-2-(1,3-dioxo-1,3-dihydro-2H-isoindol-2-yl)-5-methyl-4-[3-(trifluoromethyl)-phenyl]-4,7-dihydro[1,2,4]triazolo[1,5-a]pyrimidine-6-carboxylate (50.0 mg, 83.5 µmol; Example 1) in ethanol (6.25 ml). In a closed, pressure-proof glass tube, the reaction mixture was heated at 50° C. 1 N hydrochloric acid (670 µl, 670 µmol, 8 eq.) was then added, the reaction mixture was concentrated under reduced pressure and the residue was purified by preparative HPLC (Gromsil C18 column, 10 µm, 250×30 mm; mobile phase: acetonitrile-water-0.1% TFA 10:90→100:0). This gave the product as a solid (45 mg, 87% of theory).

LC-MS (Method 3): $R_t$=3.66 min; MS (ESIpos): m/z (%)=617.3 (100) [M+H]$^+$; MS (ESIneg): m/z (%)=615.2 (100) [M−H]$^-$.

$^1$H-NMR (400 MHz, DMSO-d$_6$): δ=1.05 (t, 3H), 2.15 (s, 3H), 4.00 (q, 2H), 6.45 (br. s, 1H), 7.30-8.20 (m, 12H), 10.80 (br. s, 1H), 12.85 (br. s, 1H).

Example 12

2-({6-Cyano-7-(4-cyanophenyl)-5-methyl-4-[3-(trifluoromethyl)phenyl]-4,7-dihydro[1,2,4]triazolo[1,5-a]pyrimidin-2-yl}carbamoyl)benzoic acid

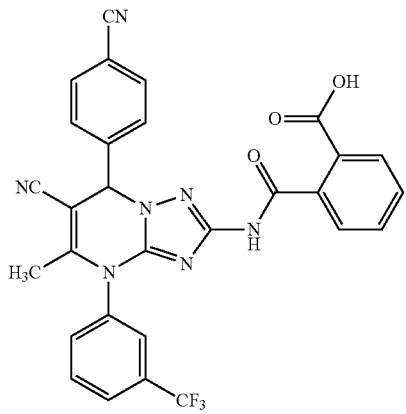 [SMILES: CC1=C(C#N)C(c2ccc(C#N)cc2)n2nc(NC(=O)c3ccccc3C(=O)O)nc2N1c1cccc(C(F)(F)F)c1]

Water (0.5 ml) and potassium carbonate (8.1 mg, 59 µmol) were added to a solution of 7-(4-cyanophenyl)-2-(1,3-dioxo-1,3-dihydro-2H-isoindol-2-yl)-5-methyl-4-[3-(trifluoromethyl)phenyl]-4,7-dihydro[1,2,4]triazolo[1,5-a]pyrimidine-6-carbonitrile (25.0 mg, 45.3 µmol; Example 3) in ethanol (3.4 ml). In a closed pressure-proof glass tube, the reaction mixture was heated at 55° C. For complete conversion, more potassium carbonate was added in two separate portions (5 mg, 36 µmol in total), and the mixture was once more heated at 55° C. 1 N hydrochloric acid (180 µl, 180 µmol) was then added, the reaction mixture was concentrated under reduced pressure and the residue was purified by preparative HPLC (Kromasil C18 column, 250×30 mm; mobile phase: acetonitrile-water-0.1% TFA 10:90→100:0). This gave the product as a solid (24.8 mg, 96% of theory).

LC-MS (Method 4): $R_t$=3.27 min; MS (ESIpos): m/z (%)=570.1 (100) [M+H]$^+$; MS (ESIneg): m/z (%)=568.1 (100) [M−H]$^-$.

$^1$H-NMR (400 MHz, DMSO-d$_6$): δ=2.00 (s, 3H), 6.45 (br. s, 1H), 7.30-8.20 (m, 12H), 10.85 (br. s, 1H), 12.85 (br. s, 1H).

Example 13

N-{(7R)-6-Cyano-7-(4-cyanophenyl)-5-methyl-4-[3-(trifluoromethyl)phenyl]-4,7-dihydro[1,2,4]-triazolo[1,5-a]pyrimidin-2-yl}-1-fluorocyclopropanecarboxamide

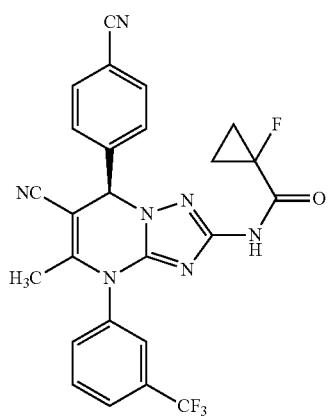 [SMILES: CC1=C(C#N)[C@@H](c2ccc(C#N)cc2)n2nc(NC(=O)C3(F)CC3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, 1-fluorocyclopropanecarbonyl chloride (20 mg, 165 µmol, 2.5 eq.) in abs. THF (1 ml) was added in two portions, and the mixture was stirred for 12 h. The reaction mixture was then concentrated under reduced pressure and directly purified by preparative HPLC (Kromasil C18 column, 5 µm, 50×20 mm; mobile phase: acetonitrile-water-0.1% TFA). After lyophilization, the product was obtained as a solid (29.5 mg, 89% of theory).

LC-MS (Method 7): $R_t$=2.03 min; MS (ESIpos): m/z (%)=508.1 (100) [M+H]$^+$; MS (ESIneg): m/z (%)=506.2 (100) [M−H]$^-$.

$^1$H-NMR (400 MHz, DMSO-d$_6$): δ=1.10-1.35 (m, 4H), 1.95 (s, 3H), 6.45 (s, 1H), 7.75-7.95 (m, 7H), 8.15 (br. s, 1H), 10.60 (br. s, 1H).

Example 14

N-{(7R)-6-Cyano-7-(4-cyanophenyl)-5-methyl-4-[3-(trifluoromethyl)phenyl]-4,7-dihydro[1,2,4]-triazolo[1,5-a]pyrimidin-2-yl}-2,2-difluoro-1-methylcyclopropanecarboxamide

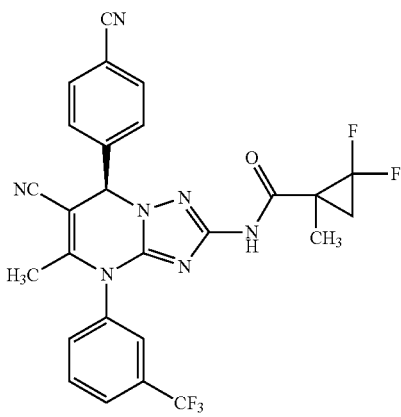 [SMILES: CC1=C(C#N)[C@@H](c2ccc(C#N)cc2)n2nc(NC(=O)C3(C)CC3(F)F)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, a solution of 2,2-difluoro-1-methylcyclopropanecarbonyl chloride (25 mg, 165 µmol, 2.5 eq.) in abs. THF (1 ml) was added in two portions. Once analysis of the reaction by HPLC showed substantial conversion (3 h), the reaction mixture was concentrated under reduced pressure and directly purified by preparative HPLC (Kromasil C18 column, 5 µm, 50×20 mm; mobile phase: acetonitrile-water-0.1% TFA). After lyophilization, the product was obtained as a solid (26.8 mg, 76% of theory).

LC-MS (Method 7): $R_t$=2.10 min; MS (ESIpos): m/z (%)=540.2 (100) [M+H]$^+$; MS (ESIneg): m/z (%)=538.2 (100) [M−H]$^−$.

$^1$H-NMR (400 MHz, DMSO-d$_6$): δ=1.30 (s, 3H), 1.40 (m, 1H), 1.90 (m, 1H), 2.00 (s, 3H), 6.45 (s, 1H), 7.75-7.95 (m, 7H), 8.20 (br. s, 1H), 10.70 (br. s, 1H).

Example 15

N-{(7R)-6-Cyano-7-(4-cyanophenyl)-5-methyl-4-[3-(trifluoromethyl)phenyl]-4,7-dihydro[1,2,4]-triazolo[1,5-a]pyrimidin-2-yl}-2,2-dimethylpropanamide

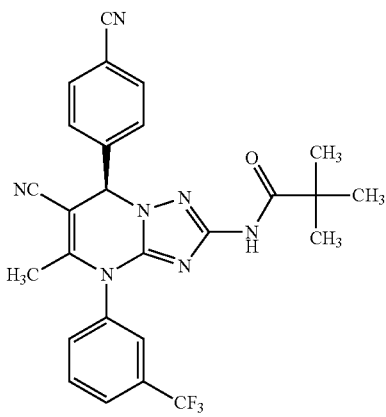 [SMILES: CC1=C(C#N)[C@@H](c2ccc(C#N)cc2)n2nc(NC(=O)C(C)(C)C)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, a solution of 2,2-dimethylpropanoyl chloride (20 mg, 164 µmol, 2.5 eq.) in abs. THF (1 ml) was added in two portions. Once analysis of the reaction by HPLC showed substantial conversion (12 h), the reaction mixture was concentrated under reduced pressure and directly purified by preparative HPLC (Kromasil C18 column, 5 µm, 50×20 mm; mobile phase: acetonitrile-water-0.1% TFA). After lyophilization, the product was obtained as a solid (26.9 mg, 81% of theory).

LC-MS (Method 7): $R_t$=2.10 min; MS (ESIpos): m/z (%)=506.2 (100) [M+H]$^+$; MS (ESIneg): m/z (%)=504.3 (100) [M−H]$^−$.

$^1$H-NMR (400 MHz, DMSO-d$_6$): δ=1.05 (s, 9H), 1.95 (s, 3H), 6.40 (s, 1H), 7.75-7.95 (m, 7H), 8.20 (br. s, 1H), 9.80 (br. s, 1H).

Example 16

N-{(7R)-6-Cyano-7-(4-cyanophenyl)-5-methyl-4-[3-(trifluoromethyl)phenyl]-4,7-dihydro[1,2,4]-triazolo[1,5-a]pyrimidin-2-yl}-2-hydroxyacetamide

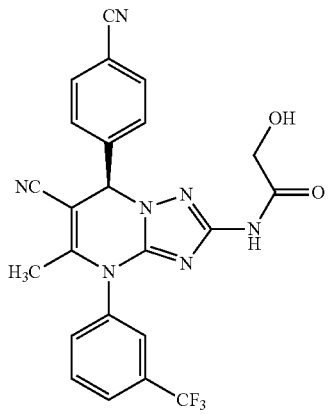 [SMILES: CC1=C(C#N)[C@@H](c2ccc(C#N)cc2)n2nc(NC(=O)CO)nc2N1c1cccc(C(F)(F)F)c1]

At RT, a solution of lithium hydroxide (2.3 mg, 95.9 µmol, 5 eq.) in water (125 µl) was added to a solution of 2-((7R)-6-cyano-7-(4-cyanophenyl)-5-methyl-4-[3-(trifluoromethyl)phenyl]-4,7-dihydro[1,2,4]triazolo[1,5-a]pyrimidin-2-ylamino)-2-oxoethyl acetate (10.0 mg, 19.2 µmol; Example 31) in THF (625 µl). After 1 h of stirring, conversion was found to be complete. 1 N hydrochloric acid (153 µl, 8 eq.) was added, and the reaction mixture was directly purified by preparative HPLC (Kromasil C18 column, 5 µm, 50×20 mm; mobile phase: acetonitrile-water-0.1% TFA). After lyophilization, the product was obtained as a solid (6.5 mg, 71% of theory).

LC-MS (Method 2): $R_t$=2.06 min; MS (ESIpos): m/z (%)=479.9 (100) [M+H]$^+$; MS (ESIneg): m/z (%)=477.9 (100) [M−H]$^−$.

$^1$H-NMR (400 MHz, DMSO-d$_6$): δ=1.95 (s, 3H), 3.85 (s, 2H), 6.45 (s, 1H), 7.75-7.95 (m, 7H), 8.20 (br. s, 1H), 10.05 (s, 1H).

Example 17

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}acetamide

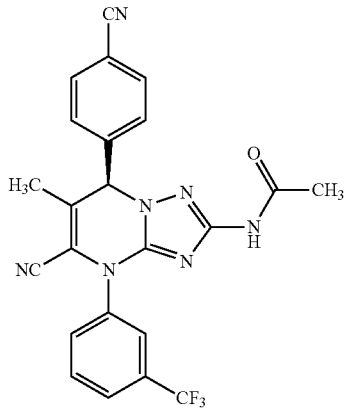 [SMILES: CC(=O)Nc1nc2n(n1)[C@H](c1ccc(C#N)cc1)C(C)=C(C#N)N2c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (22 mg, 48 µmol) was dissolved in abs. pyridine (5 ml). At room temperature, acetic anhydride (98 mg, 960 µmol, 20 eq.) was added. Once analysis of the reaction by TLC showed substantial conversion (a few hours), the reaction mixture was concentrated under reduced pressure and directly purified by preparative HPLC (Reprosil C18 column, 30×200 mm; mobile phase: acetonitrile-water-0.1% TFA). After lyophilization, the product was obtained as a solid (20.6 mg, 93% of theory).

LC-MS (Method 2): $R_t$=2.19 min; MS (ESIpos): m/z (%)=464.0 (100) $[M+H]^+$; MS (ESIneg): m/z (%)=462.1 (100) $[M-H]^-$.

$^1$H-NMR (400 MHz, DMSO-$d_6$): δ=1.85 (s, 3H), 2.00 (s, 3H), 6.45 (s, 1H), 7.70-7.95 (m, 7H), 8.20 (br. s, 1H), 10.40 (br. s, 1H).

Example 18

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}-2-methylpropanamide

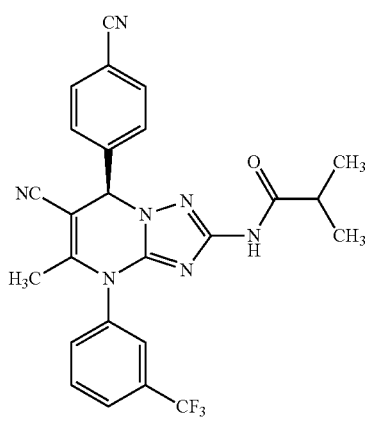

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, isobutyryl chloride (21 mg, 107 µmol, 3 eq.) was added. After 12 h of stirring, analysis of the reaction by HPLC showed substantial conversion. The reaction mixture was concentrated under reduced pressure and directly purified by preparative HPLC (Gromsil C18 column, 30×250 mm; mobile phase: acetonitrile-water-0.1% TFA). After lyophilization, the product was obtained as a solid (24.5 mg, 76% of theory).

LC-MS (Method 2): $R_t$=2.37 min; MS (ESIpos): m/z (%)=492.1 (100) $[M+H]^+$; MS (ESIneg): m/z (%)=490.2 (100) $[M-H]^-$.

$^1$H-NMR (400 MHz, DMSO-$d_6$): δ=0.90 (d, 3H), 0.95 (d, 3H), 2.00 (s, 3H), 2.45 (m, 1H), 6.45 (s, 1H), 7.70-7.95 (m, 7H), 8.20 (br. s, 1H), 10.35 (br. s, 1H).

Example 19

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}propanamide

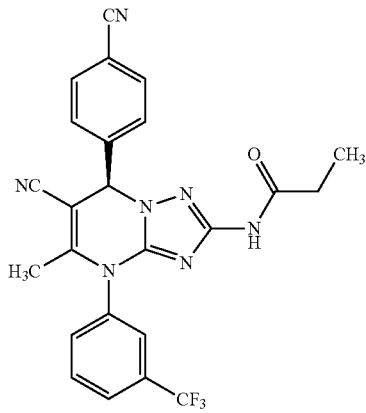

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (40 mg, 87 µmol) was dissolved in abs. pyridine (2 ml). At room temperature, propionic anhydride (227 mg, 1747 µmol, 20 eq.) was added. After 12 h, analysis of the reaction by HPLC showed substantial conversion. The reaction mixture was directly purified by preparative HPLC (Reprosil C18 column, 30×250 mm; mobile phase: acetonitrile-water-0.1% TFA). After lyophilization, the product was obtained as a solid (32.6 mg, 78% of theory).

LC-MS (Method 2): $R_t$=2.28 min; MS (ESIpos): m/z (%)=478.1 (100) $[M+H]^+$; MS (ESIneg): m/z (%)=476.2 (100) $[M-H]^-$.

$^1$H-NMR (400 MHz, DMSO-$d_6$): δ=0.90 (t, 3H), 1.95 (s, 3H), 2.15 (q, 2H), 6.45 (s, 1H), 7.70-7.95 (m, 7H), 8.20 (br. s, 1H), 10.35 (br. s, 1H).

Example 20

N-{(7R)-6-Cyano-7-(4-cyanophenyl)-5-methyl-4-[3-(trifluoromethyl)phenyl]-4,7-dihydro[1,2,4]-triazolo[1,5-a]pyrimidin-2-yl}cyclopentanecarboxamide

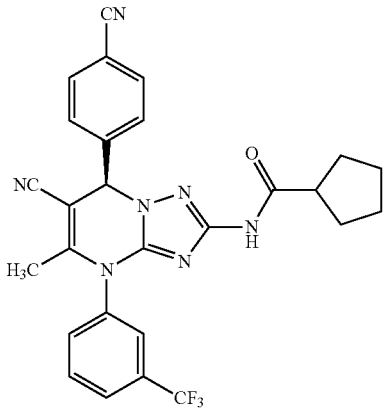

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, cyclopentanecarbonyl chloride (26 mg, 197 µmol, 3 eq.) was added. After 12 h, analysis of the reaction by HPLC showed substantial conversion. The reaction mixture was concentrated under reduced pressure and purified by preparative HPLC (Reprosil C18 column, 30×250 mm; mobile phase: acetonitrile-water-0.1% TFA). After lyophilization, the product was obtained as a solid (14.6 mg, 41% of theory).

LC-MS (Method 7): $R_t$=2.12 min; MS (ESIpos): m/z (%)=518.2 (100) [M+H]$^+$; MS (ESIneg): m/z (%)=516.3 (100) [M−H]$^−$.

$^1$H-NMR (400 MHz, DMSO-d$_6$): δ=0.85-1.70 (m, 8H), 2.00 (s, 3H), 2.65 (m, 1H), 6.40 (s, 1H), 7.70-8.00 (m, 7H), 8.20 (br. s, 1H), 10.40 (br. s, 1H).

Example 21

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}cyclobutanecarboxamide

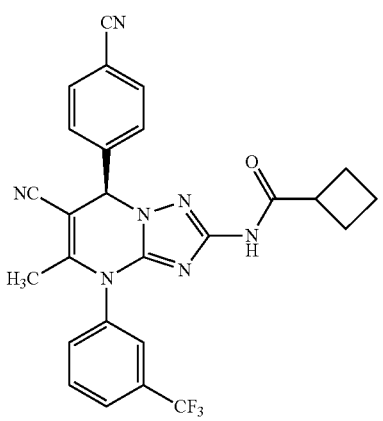 [SMILES: CC1=C(C#N)[C@@H](c2ccc(C#N)cc2)n2nc(NC(=O)C3CCC3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, cyclobutanecarbonyl chloride (23 mg, 193 µmol, 3 eq.) was added. After 12 h, analysis of the reaction by HPLC showed substantial conversion. The reaction mixture was concentrated under reduced pressure and purified by preparative HPLC (Reprosil C18 column, 30×250 mm; mobile phase: acetonitrile-water-0.1% TFA). After lyophilization, the product was obtained as a solid (21.9 mg, 68% of theory).

LC-MS (Method 2): $R_t$=2.45 min; MS (ESIpos): m/z (%)=504.1 (100) [M+H]$^+$; MS (ESIneg): m/z (%)=502.2 (100) [M−H]$^−$.

$^1$H-NMR (400 MHz, DMSO-d$_6$): δ=1.40-2.10 (m, 6H), 2.00 (s, 3H), 3.10 (m, 1H), 6.40 (s, 1H), 7.70-7.95 (m, 7H), 8.20 (br. s, 1H), 10.25 (br. s, 1H).

Example 22

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}cyclopropanecarboxamide

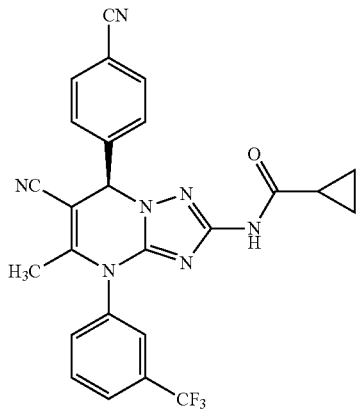 [SMILES: CC1=C(C#N)[C@@H](c2ccc(C#N)cc2)n2nc(NC(=O)C3CC3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, cyclopropanecarbonyl chloride (20 mg, 192 µmol, 3 eq.) was added. After 12 h, analysis of the reaction by HPLC showed substantial conversion. The reaction mixture was concentrated under reduced pressure and purified by preparative HPLC (Reprosil C18 column, 30×250 mm; mobile phase: acetonitrile-water-0.1% TFA). After lyophilization, the product was obtained as a solid (11.8 mg, 38% of theory).

LC-MS (Method 2): $R_t$=2.34 min; MS (ESIpos): m/z (%)=490.0 (100) [M+H]$^+$; MS (ESIneg): m/z (%)=488.0 (100) [M−H]$^−$.

$^1$H-NMR (400 MHz, DMSO-d$_6$): δ=0.65 (m, 4H), 1.70 (m, 1H), 2.00 (s, 3H), 6.40 (s, 1H), 7.70-7.95 (m, 7H), 8.20 (br. s, 1H), 10.70 (br. s, 1H).

Example 23

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}cyclohexanecarboxamide

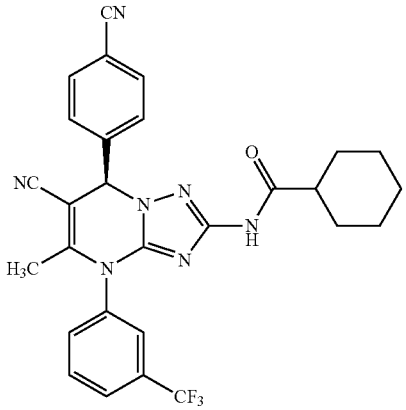 [SMILES: CC1=C(C#N)[C@@H](c2ccc(C#N)cc2)n2nc(NC(=O)C3CCCCC3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (13 mg, 28 μmol) was dissolved in abs. pyridine (0.65 ml). At room temperature, cyclohexanecarbonyl chloride (8.3 mg, 57 μmol, 2 eq.) was added. After 12 h, analysis of the reaction by HPLC showed substantial conversion. The reaction mixture was concentrated under reduced pressure and purified by preparative HPLC (Kromasil C18 column, 20×50 mm; mobile phase: acetonitrile-water-0.1% TFA). After lyophilization, the product was obtained as a solid (12.5 mg, 83% of theory).

LC-MS (Method 2): $R_t$=2.59 min; MS (ESIpos): m/z (%)=532.1 (100) [M+H]$^+$; MS (ESIneg): m/z (%)=530.2 (100) [M−H]$^−$.

$^1$H-NMR (400 MHz, DMSO-d$_6$): δ=1.00-1.30 (m, 5H), 1.50-1.70 (m, 5H), 2.00 (s, 3H), 2.20 (br. m, 1H), 6.40 (s, 1H), 7.70-7.95 (m, 7H), 8.20 (br. s, 1H), 10.30 (br. s, 1H).

Example 24

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}thiophene-2-carboxamide

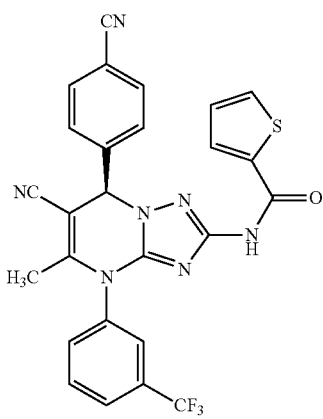 [SMILES: CC1=C(C#N)[C@@H](c2ccc(C#N)cc2)n2nc(NC(=O)c3cccs3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 μmol) was dissolved in abs. pyridine (1.5 ml). At room temperature, thiophene-2-carbonyl chloride (29 mg, 197 μmol, 3 eq.) was added. After 12 h, analysis of the reaction by HPLC showed substantial conversion. The reaction mixture was concentrated under reduced pressure and purified by preparative HPLC (Reprosil C18 column, 30×250 mm; mobile phase: acetonitrile-water-0.1% TFA). After lyophilization, the product was obtained as a solid (9.6 mg, 28% of theory).

LC-MS (Method 2): $R_t$=2.49 min; MS (ESIpos): m/z (%)=532.0 (100) [M+H]$^+$; MS (ESIneg): m/z (%)=530.1 (100) [M−H]$^−$.

$^1$H-NMR (400 MHz, DMSO-d$_6$): δ=2.00 (s, 3H), 6.50 (s, 1H), 7.10 (m, 1H), 7.75-8.00 (m, 9H), 8.20 (br. s, 1H), 10.85 (br. s, 1H).

Example 25

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}-3-methylbutanamide

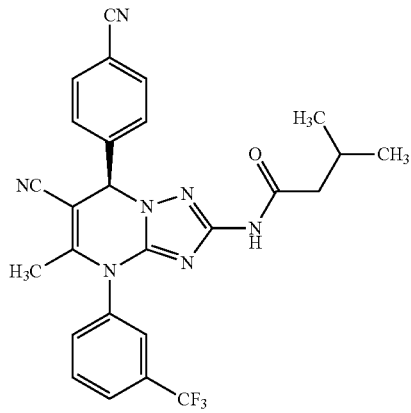

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 μmol) was dissolved in abs. pyridine (1.5 ml). At room temperature, isovaleryl chloride (24 mg, 197 μmol, 3 eq.) was added. After 12 h, analysis of the reaction by HPLC showed substantial conversion. The reaction mixture was concentrated under reduced pressure and purified by preparative HPLC (Kromasil C18 column, 20×50 mm; mobile phase: acetonitrile-water-0.1% TFA). After lyophilization, the product was obtained as a solid (22.4 mg, 68% of theory).

LC-MS (Method 7): $R_t$=2.08 min; MS (ESIpos): m/z (%)=506.2 (100) [M+H]$^+$; MS (ESIneg): m/z (%)=504.3 (100) [M−H]$^−$.

$^1$H-NMR (400 MHz, DMSO-d$_6$): δ=0.80 (d, 6H), 1.90 (m, 1H), 2.00 (s, 3H), 2.05 (m, 2H), 6.40 (s, 1H), 7.70-7.95 (m, 7H), 8.20 (br. s, 1H), 10.35 (br. s, 1H).

Example 26

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}tetrahydrofuran-3-carboxamide

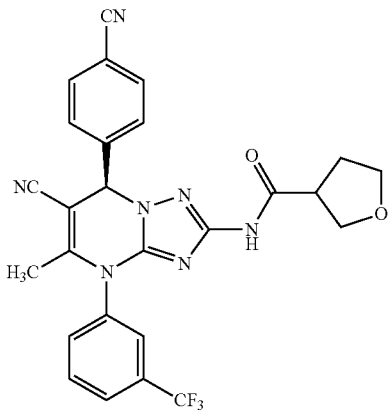 [SMILES: CC1=C(C#N)[C@@H](c2ccc(C#N)cc2)n2nc(NC(=O)C3CCOC3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, tetrahydrofuran-3-carbonyl chloride (26 mg, 197 µmol, 3 eq.) was added. After 12 h, analysis of the reaction by HPLC showed substantial conversion. The reaction mixture was concentrated under reduced pressure and purified by preparative HPLC (Reprosil C18 column, 250×30 mm; mobile phase: acetonitrile-water-0.1% TFA). After lyophilization, the product was obtained as a solid (21.1 mg, 62% of theory).

LC-MS (Method 2): $R_t$=2.24 min; MS (ESIpos): m/z (%)=520.1 (100) [M+H]$^+$; MS (ESIneg): m/z (%)=518.2 (100) [M−H]$^-$.

$^1$H-NMR (400 MHz, DMSO-d$_6$): δ=1.90 (m, 2H), 2.00 (s, 3H), 3.00 (m, 1H), 3.50-3.80 (m, 4H), 6.45 (s, 1H), 7.70-7.95 (m, 7H), 8.20 (br. s, 1H), 10.55 (br. s, 1H).

Example 27

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}-2-phenoxyacetamide

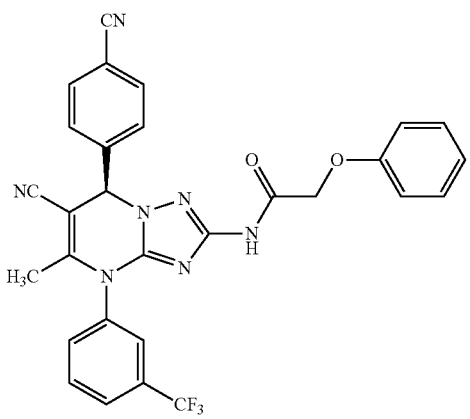 [SMILES: CC1=C(C#N)[C@@H](c2ccc(C#N)cc2)n2nc(NC(=O)COc3ccccc3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, phenoxyacetyl chloride (21 mg, 197 µmol, 3 eq.) was added. After 12 h, analysis of the reaction by HPLC showed substantial conversion. The reaction mixture was concentrated under reduced pressure and purified by preparative HPLC (Kromasil C18 column, 5 µm, 50×20 mm; mobile phase: acetonitrile-water-0.1% TFA). After lyophilization, the product was obtained as a solid (20.9 mg, 56% of theory).

LC-MS (Method 7): $R_t$=2.17 min; MS (ESIpos): m/z (%)=556.2 (100) [M+H]$^+$; MS (ESIneg): m/z (%)=554.3 (100) [M−H]$^-$.

$^1$H-NMR (400 MHz, DMSO-d$_6$): δ=2.00 (s, 3H), 4.55 (s, 2H), 6.45 (s, 1H), 6.70 (d, 2H), 6.80 (t, 1H), 7.15 (t, 2H), 7.70-7.95 (m, 7H), 8.20 (br. s, 1H), 10.70 (br. s, 1H).

Example 28

N$^2$-Acetyl-N-[(7R)-6-cyano-7-(4-cyanophenyl)-5-methyl-4-[3-(trifluoromethyl)phenyl]-4,7-dihydro[1,2,4]triazolo[1,5-a]pyrimidin-2-yl]glycinamide

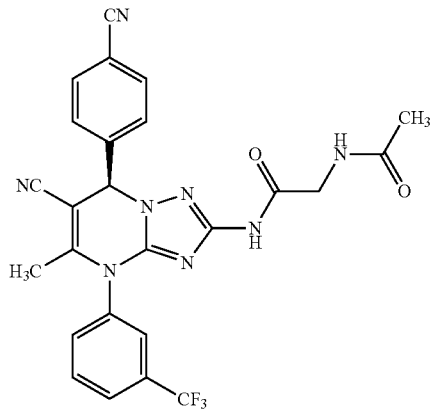 [SMILES: CC(=O)NCC(=O)Nc1nc2n(n1)[C@H](c1ccc(C#N)cc1)C(C#N)=C(C)N2c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (13 mg, 28 µmol) was dissolved in abs. pyridine (2.0 ml). At room temperature, acetamidoacetyl chloride (8 mg, 57 µmol, 2 eq.) was added. After 12 h, analysis of the reaction by HPLC showed substantial conversion. The reaction mixture was concentrated under reduced pressure and purified by preparative HPLC (Kromasil C18 column, 50×20 mm; mobile phase: acetonitrile-water-0.1% TFA). After lyophilization, the product was obtained as a solid (9.6 mg, 65% of theory).

LC-MS (Method 2): $R_t$=2.06 min; MS (ESIpos): m/z (%)=521.1 (100) [M+H]$^+$; MS (ESIneg): m/z (%)=519.2 (100) [M−H]$^-$.

$^1$H-NMR (400 MHz, DMSO-d$_6$): δ=1.80 (s, 3H), 2.00 (s, 3H), 3.65 (d, 2H), 6.45 (s, 1H), 7.70-7.95 (m, 8H), 8.20 (br. s, 1H), 10.45 (br. s, 1H).

Example 29

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}benzamide

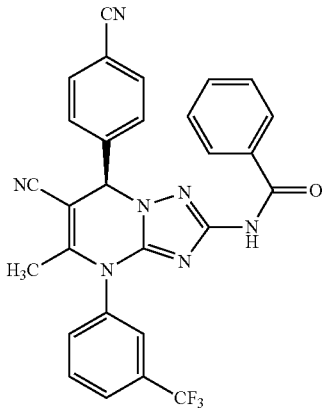 [SMILES: CC1=C(C#N)[C@@H](c2ccc(C#N)cc2)n2nc(NC(=O)c3ccccc3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (13.5 mg, 29 µmol) was dissolved in abs. pyridine (1.0 ml). At room temperature, benzoic anhydride (11 mg, 47 µmol, 1.6 eq.) was added, and the mixture was stirred for 12 h. The reaction mixture was then concentrated under reduced pressure and purified by preparative HPLC (Gromsil C18 column, 10 µm, 30×250 mm; mobile phase: acetonitrile-water-0.1% TFA). After lyophilization, the product was obtained as a solid (3.5 mg, 23% of theory).

LC-MS (Method 5): $R_t$=1.27 min; MS (ESIpos): m/z (%)=526.2 (100) [M+H]$^+$; MS (ESIneg): m/z (%)=524.4 (100) [M−H]$^-$.

$^1$H-NMR (400 MHz, DMSO-d$_6$): δ=2.00 (s, 3H), 6.45 (s, 1H), 7.40 (m, 2H), 7.55 (t, 1H), 7.70-7.95 (m, 9H), 8.20 (br. s, 1H), 10.80 (br. s, 1H).

Example 30

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}-2-[2-(2-methoxyethoxy)ethoxy]acetamide

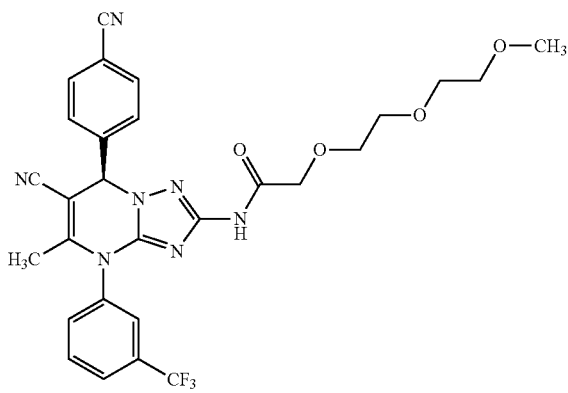

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (14 mg, 31 µmol) was dissolved in abs. pyridine (0.7 ml). At room temperature, 2-[2-(2-methoxyethoxy)ethoxy]acetyl chloride (12 mg, 61 µmol, 2 eq.) was added. After 12 h, analysis of the reaction by HPLC showed substantial conversion. The reaction mixture was concentrated under reduced pressure and purified by preparative HPLC (Gromsil C18 column, 30×250 mm; mobile phase: acetonitrile-water-0.1% TFA). After lyophilization, the product was obtained as a solid (12.4 mg, 70% of theory).

LC-MS (Method 2): $R_t$=2.29 min; MS (ESIpos): m/z (%)=582.2 (100) [M+H]$^+$; MS (ESIneg): m/z (%)=580.2 (100) [M−H]$^-$.

$^1$H-NMR (400 MHz, DMSO-d$_6$): δ=2.00 (s, 3H), 3.15 (s, 3H), 3.30-3.50 (m, 8H), 3.90 (s, 2H), 6.45 (s, 1H), 7.70-8.00 (m, 7H), 8.20 (br. s, 1H), 10.15 (br. s, 1H).

Example 31

2-({(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}amino)-2-oxoethyl acetate

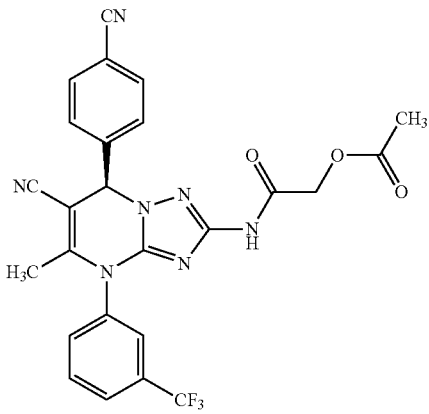 [SMILES: CC(=O)OCC(=O)Nc1nc2n(n1)[C@H](c1ccc(C#N)cc1)C(C#N)=C(C)N2c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 µmol) was dissolved in abs. pyridine (1.5 ml). At room temperature, acetoxyacetyl chloride (37 mg, 262 µmol, 4 eq.) was added. After 12 h, analysis of the reaction by HPLC showed substantial conversion. The reaction mixture was concentrated under reduced pressure and purified by preparative HPLC (Gromsil C18 column, 30×250 mm; mobile phase: acetonitrile-water-0.1% TFA). After lyophilization, the product was obtained as a solid (19.6 mg, 57% of theory).

LC-MS (Method 2): $R_t$=2.30 min; MS (ESIpos): m/z (%)=522.1 (100) [M+H]$^+$; MS (ESIneg): m/z (%)=520.2 (100) [M−H]$^-$.

$^1$H-NMR (400 MHz, DMSO-d$_6$): δ=1.95 (s, 3H), 2.00 (s, 3H), 4.45 (br. s, 2H), 6.45 (s, 1H), 7.70-7.95 (m, 7H), 8.20 (br. s, 1H), 10.70 (br. s, 1H).

Example 32

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}isoxazole-5-carboxamide

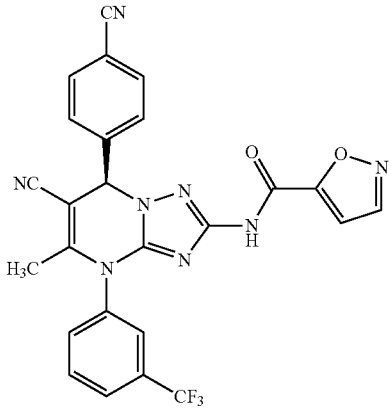 [SMILES: CC1=C(C#N)[C@@H](c2ccc(C#N)cc2)n2nc(NC(=O)c3ccno3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (30 mg, 66 μmol) was dissolved in abs. pyridine (2 ml). At room temperature, isoxazol-5-carbonyl chloride (26 mg, 197 μmol, 3 eq.) was added, and the mixture was stirred overnight. Once HPLC showed substantial conversion, the reaction mixture was concentrated under reduced pressure and purified by preparative HPLC (Gromsil C18 column, 30×250 mm; mobile phase: acetonitrile-water-0.1% TFA). After lyophilization, the product was obtained as a solid (5 mg, 15% of theory).

LC-MS (Method 7): $R_t$=1.92 min; MS (ESIpos): m/z (%)=517.0 (100) [M+H]$^+$; MS (ESIneg): m/z (%)=515.1 (100) [M–H]$^-$.

$^1$H-NMR (400 MHz, DMSO-d$_6$): δ=2.00 (s, 3H), 6.50 (s, 1H), 7.25 (s, 1H), 7.70-7.95 (m, 7H), 8.20 (br. s, 1H), 8.70 (s, 1H), 11.35 (s, 1H).

Example 33 tert-Butyl [2-({(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}amino)-2-oxoethyl]carbamate

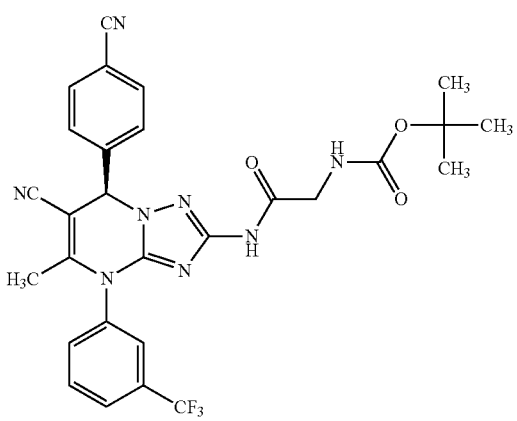 [SMILES: CC1=C(C#N)[C@@H](c2ccc(C#N)cc2)n2nc(NC(=O)CNC(=O)OC(C)(C)C)nc2N1c1cccc(C(F)(F)F)c1]

Under an atmosphere of argon protective gas, N-Boc-Gly-OH (5 mg, 28 μmol) and NMM (5.3 mg, 52 μmol, 2.4 eq.) were dissolved in abs. THF (1 ml), and isobutyl chloroformate (4.2 mg, 31 μmol, 1.4 eq.) was added at –15° C. (solution A). At –78° C., (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile hydrochloride (10 mg, 22 μmol) and NMM (2.2 mg, 22 μmol, 1 eq.) were added, and the mixture was stirred overnight, during which time it slowly warmed to RT. Since the conversion was still incomplete, more solution A consisting of in each case 285 μmol of N-Boc-Gly-OH, isobutyl chloroformate and NMM in abs. THF was added at –15° C., and the mixture was stirred for 3 d, warming to RT. The reaction mixture was then directly purified by preparative HPLC (Gromsil C18 column, 30×250 mm; mobile phase: acetonitrile-water-0.1% TFA). After lyophilization, the product was obtained as a solid (6.3 mg, 50% of theory).

LC-MS (Method 7): $R_t$=2.01 min; MS (ESIpos): m/z (%)=523.1 (100), 579.2 (80) [M+H]$^+$; MS (ESIneg): m/z (%)=577.3 (100) [M–H]$^-$.

Example 34

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}glycinamide trifluoroacetate

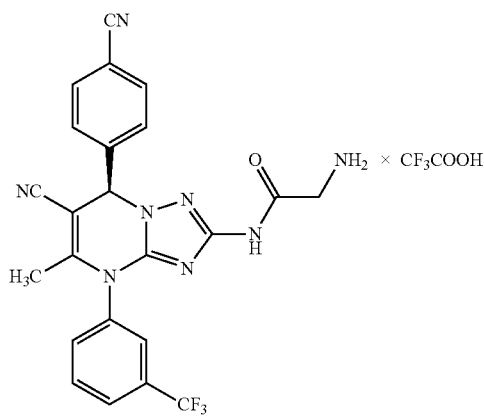 [SMILES: CC1=C(C#N)[C@@H](c2ccc(C#N)cc2)n2nc(NC(=O)CN)nc2N1c1cccc(C(F)(F)F)c1]

Under an atmosphere of argon protective gas, tert-butyl [2-((7R)-6-cyano-7-(4-cyanophenyl)-5-methyl-4-[3-(trifluoromethyl)phenyl]-4,7-dihydro[1,2,4]triazolo[1,5-a]pyrimidin-2-ylamino)-2-oxoethyl]carbamate (6.4 mg, 11 μmol) was dissolved in dry dichloromethane (5 ml). At room temperature, trifluoroacetic acid (1 ml) was added, and the mixture was stirred for 40 min. The reaction mixture was then concentrated under reduced pressure and the residue was purified by preparative HPLC (Gromsil C18 column, 30×250 mm; mobile phase: acetonitrile-water-0.1% TFA). After lyophilization, the product was obtained as a solid (~6 mg, quant.).

LC-MS (Method 2): $R_t$=1.51 min; MS (ESIpos): m/z (%)=479.1 (100) [M+H]$^+$; MS (ESIneg): m/z (%)=477.1 (100) [M–H]$^-$.

$^1$H-NMR (400 MHz, DMSO-d$_6$): δ=2.00 (s, 3H), 3.60 (br. s, 2H), 6.50 (s, 1H), 7.70-7.95 (m, 9H), 8.20 (br. s, 1H), 10.95 (s, 1H).

Example 35

N-{(7S)-6-Cyano-7-[4-cyano-2-(methylsulfonyl)phenyl]-5-methyl-4-[3-(trifluoromethyl)phenyl]-4,7-dihydro[1,2,4]triazolo[1,5-a]pyrimidin-2-yl}cyclopropanecarboxamide

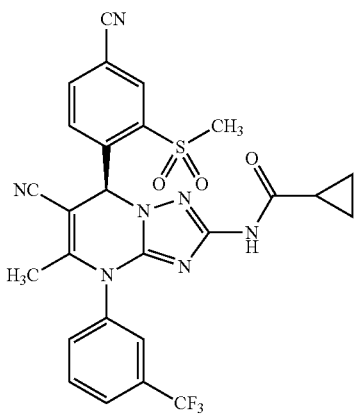 [SMILES: CC1=C(C#N)[C@@H](c2ccc(C#N)cc2S(C)(=O)=O)n2nc(NC(=O)C3CC3)nc2N1c1cccc(C(F)(F)F)c1]

Under an atmosphere of argon protective gas, (7S)-2-amino-7-[4-cyano-2-(methylsulfonyl)phenyl]-5-methyl-4-[3-(trifluoromethyl)phenyl]-4,7-dihydro[1,2,4]triazolo[1,5-a]pyrimidine-6-carbonitrile hydrochloride (16 mg, 30 µmol) was dissolved in abs. pyridine (1 ml). At room temperature, cyclopropanecarbonyl chloride was added in two portions (in each case 3.7 mg, 36 µmol, 1.2 eq.). Once HPLC showed substantial conversion (12 h), the reaction mixture was concentrated under reduced pressure and purified by preparative HPLC (Macherey & Nagel Gravity C18 column, 21×300 mm; mobile phase: acetonitrile-water-0.1% TFA). After lyophilization, the product was obtained as a solid (11.2 mg, 66% of theory).

LC-MS (Method 5): $R_t$=1.19 min; MS (ESIpos): m/z (%)=568.0 (100) [M+H]$^+$; MS (ESIneg): m/z (%)=566.2 (100) [M−H]$^−$.

$^1$H-NMR (400 MHz, DMSO-d$_6$): δ=0.65 (m, 4H), 1.65 (m, 1H), 2.00 (s, 3H), 3.65 (s, 3H), 7.45 (s, 1H), 7.80-8.40 (m, 6H), 8.45 (s, 1H), 10.85 (br. s, 1H).

Example 36

Methyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}carbamate

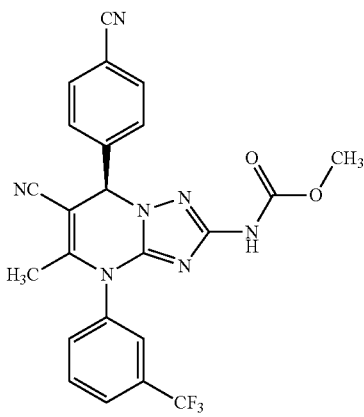

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile (30 mg, 71 µmol) was dissolved in a mixture of abs. THF (3 ml) and abs. pyridine (57.5 µl). At room temperature, pyridine (5×57 µl) and methyl chloroformate (5×33.6 mg, 5×356 µmol; 25 eq.) were added in a plurality of portions. The mixture was then heated at 80° C. for 12 h. Once HPLC analysis showed substantial conversion, the reaction mixture was concentrated under reduced pressure and purified by preparative HPLC (Kromasil C18 column, 30×250 mm; mobile phase: acetonitrile-water-0.1% TFA). After lyophilization, the product was obtained as a solid (31.1 mg, 91% of theory).

LC-MS (Method 5): $R_t$=1.16 min; MS (ESIpos): m/z (%)=480.3 (100) [M+H]$^+$; MS (ESIneg): m/z (%)=478.4 (100) [M−H]$^−$.

$^1$H-NMR (500 MHz, DMSO-d$_6$): δ=2.00 (s, 3H), 3.50 (s, 3H), 6.40 (s, 1H), 7.70-7.95 (m, 7H), 8.15 (br. s, 1H), 10.00 (s, 1H).

Example 37

Methyl {6-cyano-7-[4-cyano-2-(methylsulfonyl)phenyl]-5-methyl-4-[3-(trifluoromethyl)phenyl]-4,7-dihydro[1,2,4]triazolo[1,5-a]pyrimidin-2-yl}carbamate

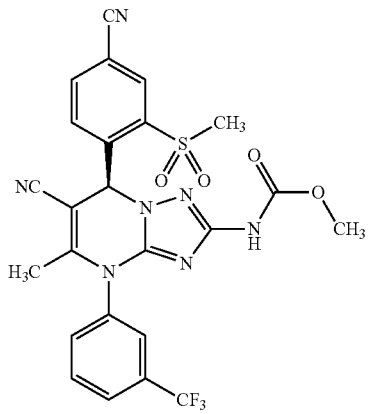

Under an atmosphere of argon protective gas, 2-amino-7-[4-cyano-2-(methylsulfonyl)phenyl]-5-methyl-4-[3-(trifluoromethyl)phenyl]-4,7-dihydro[1,2,4]triazolo[1,5-a]pyrimidine-6-carbonitrile (7 mg, 13.6 µmol) was dissolved in a mixture of abs. THF (0.6 ml) and abs. pyridine (11 µl). At room temperature, abs. pyridine (5×11 µl) and methyl chloroformate (5×6.4 mg, 5×68.1 µmol; 25 eq.) were added in a plurality of portions. The mixture was then heated as 80° C. for 12 h. Once HPLC analysis showed substantial conversion, the reaction mixture was concentrated under reduced pressure and purified by preparative HPLC (Gromsil C18 column, 30×250 mm; mobile phase: acetonitrile-water-0.1% TFA). After lyophilization, the product was obtained as a solid (5.4 mg, 69% of theory).

LC-MS (Method 7): $R_t$=1.91 min; MS (ESIpos): m/z (%)=558.1 (100) [M+H]$^+$; MS (ESIneg): m/z (%)=556.1 (100) [M−H]$^−$.

$^1$H-NMR (400 MHz, DMSO-d$_6$): δ=2.00 (s, 3H), 3.50 (s, 3H), 3.65 (s, 3H), 7.45 (s, 1H), 7.80-8.45 (m, 7H), 10.20 (s, 1H).

Example 38

Benzyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}carbamate

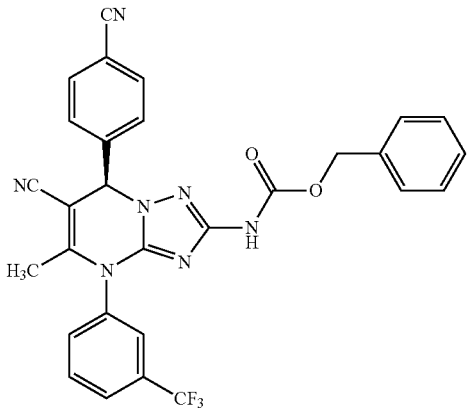 [SMILES: CC1=C(C#N)[C@@H](c2ccc(C#N)cc2)n2nc(NC(=O)OCc3ccccc3)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile (400 mg, 874 µmol) was initially charged in abs. pyridine (15 ml). At 0° C., benzyl chloroformate was added in a plurality of portions (3×460 mg, 3×2621 µmol; 9 eq.), and the mixture was then stirred for 12 h with warming to RT. Once HPLC analysis showed substantial conversion, the reaction mixture was concentrated under reduced pressure and purified by preparative HPLC (Gromsil C18 column, 30×250 mm; mobile phase: acetonitrile-water-0.1% TFA). After lyophilization, the product was obtained as a solid (500 mg, quant.).

LC-MS (Method 7): $R_t$=2.23 min; MS (ESIpos): m/z (%)=556.1 (100) [M+H]$^+$; MS (ESIneg): m/z (%)=554.1 (100) [M−H]$^−$.

$^1$H-NMR (400 MHz, DMSO-$d_6$): δ=1.95 (s, 3H), 5.00 (s, 2H), 6.40 (s, 1H), 7.20-7.35 (m, 5H), 7.70-7.95 (m, 7H), 8.15 (br. s, 1H), 10.15 (s, 1H).

Example 39

Benzyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}methylcarbamate

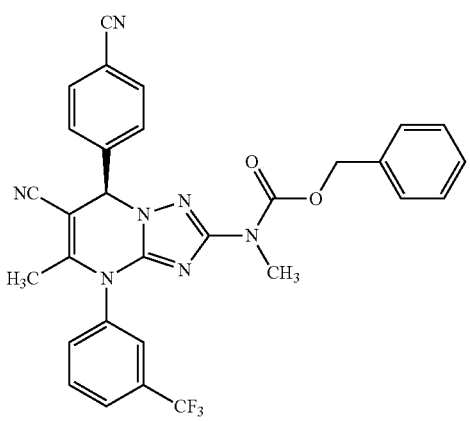 [SMILES: CC1=C(C#N)[C@@H](c2ccc(C#N)cc2)n2nc(N(C)C(=O)OCc3ccccc3)nc2N1c1cccc(C(F)(F)F)c1]

Potassium carbonate (6.0 mg, 43 µmol, 1.6 eq.), 18-crown-6 (11.4 mg, 43 µmol, 1.5 eq.) and methyl iodide (6.1 mg, 53 µmol, 2.0 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (15 mg, 27 µmol) in DMF (2 ml). The reaction mixture was stirred at RT for 12 h and then concentrated under reduced pressure and purified by preparative HPLC (Gromsil C18 column, 30×250 mm; mobile phase: acetonitrile-water-0.1% TFA). After lyophilization, the product was obtained as a solid (13.3 mg, 86% of theory).

LC-MS (Method 5): $R_t$=1.41 min; MS (ESIpos): m/z (%)=570.1 (100) [M+H]$^+$; MS (ESIneg): m/z (%)=569.1 (70) [M−H]$^−$.

Example 40

Benzyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}ethylcarbamate

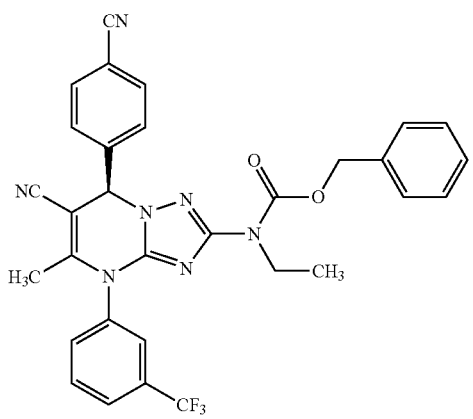

Potassium carbonate (8 mg, 58 µmol, 1.6 eq.), 18-crown-6 (15.2 mg, 58 µmol, 1.6 eq.) and iodoethane (9 mg, 58 µmol, 1.6 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (20 mg, 36 µmol) in DMF (2 ml). The reaction mixture was stirred at RT for 12 h and then concentrated under reduced pressure. The residue was acidified with acetic acid (4 mg, 72 µmol, 2 eq.) and then purified by preparative HPLC (Kromasil C18 column, 5 µm, 50×20 mm; mobile phase: acetonitrile-water-0.1% TFA). After lyophilization, the product was obtained as a solid (19.6 mg, 93% of theory).

LC-MS (Method 2): $R_t$=2.79 min; MS (ESIpos): m/z (%)=584.1 (100) [M+H]$^+$; MS (ESIneg): m/z (%)=582.1 (100) [M−H]$^−$.

$^1$H-NMR (400 MHz, DMSO-$d_6$): δ=0.95 (t, 3H), 2.00 (s, 3H), 3.45 (m, 2H), 5.00 (d, 1H), 5.05 (d, 1H), 6.50 (s, 1H), 7.15-7.40 (m, 5H), 7.70-7.95 (m, 7H), 8.15 (br. s, 1H).

Example 41

Benzyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}(cyanomethyl)carbamate

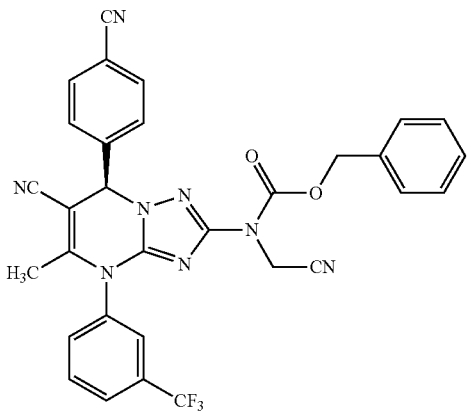 [SMILES: CC1=C(C#N)[C@@H](c2ccc(C#N)cc2)n2nc(N(CC#N)C(=O)OCc3ccccc3)nc2N1c1cccc(C(F)(F)F)c1]

Potassium carbonate (15.7 mg, 113 μmol, 2.1 eq.), 18-crown-6 (30 mg, 113 μmol, 2.1 eq.) and iodoacetonitrile (19 mg, 113 μmol, 2.1 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (30 mg, 54 μmol) in DMF (2 ml). The reaction mixture was stirred at RT for 12 h and then concentrated under reduced pressure. The residue was acidified with acetic acid and then purified by preparative HPLC (Kromasil C18 column, 5 μm, 50×20 mm; mobile phase: acetonitrile-water-0.1% TFA). After lyophilization, the product was obtained as a solid (25 mg, 78% of theory).

LC-MS (Method 5): $R_t$=1.40 min; MS (ESIpos): m/z (%)=434.0 (100), 550.9 (20), 595.0 (30) [M+H]$^+$; MS (ESIneg): m/z (%)=593.8 (100) [M−H]$^−$.

$^1$H-NMR (400 MHz, DMSO-d$_6$): δ=2.00 (s, 3H), 4.55 (d, 2H), 5.10 (d, 2H), 6.55 (s, 1H), 7.15-7.35 (m, 5H), 7.70-7.95 (m, 7H), 8.15 (br. s, 1H).

Example 42

Benzyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}propylcarbamate

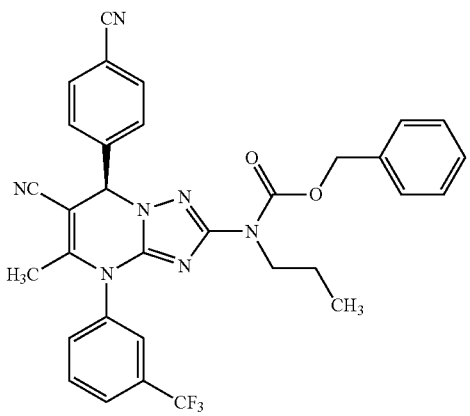 [SMILES: CCCN(C(=O)OCc1ccccc1)c1nc2n(n1)[C@H](c1ccc(C#N)cc1)C(C#N)=C(C)N2c1cccc(C(F)(F)F)c1]

Potassium carbonate (15.7 mg, 113 μmol, 2.1 eq.), 18-crown-6 (30 mg, 113 μmol, 2.1 eq.) and n-propyl iodide (19.2 mg, 113 μmol, 2.1 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (30 mg, 54 μmol) in DMF (2 ml). The reaction mixture was stirred at RT for 12 h and then concentrated under reduced pressure. The residue was acidified with acetic acid and then purified by preparative HPLC (Kromasil C18 column, 5 μm, 50×20 mm; mobile phase: acetonitrile-water-0.1% TFA). After lyophilization, the product was obtained as a solid (25 mg, 77% of theory).

LC-MS (Method 5): $R_t$=1.50 min; MS (ESIpos): m/z (%)=598.1 (100) [M+H]$^+$; MS (ESIneg): m/z (%)=596.2 (100) [M−H]$^−$.

$^1$H-NMR (400 MHz, DMSO-d$_6$): δ=0.70 (t, 3H), 1.35 (m, 2H), 2.00 (s, 3H), 3.45 (m, 2H), 5.00 (d, 1H), 5.05 (d, 1H), 6.50 (s, 1H), 7.15-7.40 (m, 5H), 7.70-7.95 (m, 7H), 8.15 (br. s, 1H).

Example 43

Benzyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}(2-methylpropyl)carbamate

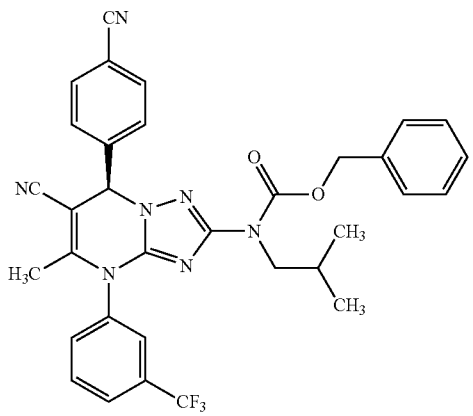 [SMILES: CC1=C(C#N)[C@@H](c2ccc(C#N)cc2)n2nc(N(CC(C)C)C(=O)OCc3ccccc3)nc2N1c1cccc(C(F)(F)F)c1]

Potassium carbonate (15.7 mg, 113 μmol, 2.1 eq.), 18-crown-6 (30 mg, 113 μmol, 2.1 eq.) and 1-iodo-2-methylpropane (21 mg, 113 μmol, 2.1 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (30 mg, 54 μmol) in DMF (2 ml). The reaction mixture was stirred at RT for 12 h and then concentrated under reduced pressure. The residue was acidified with acetic acid (3 eq.) and then purified by preparative HPLC (Kromasil C18 column, 5 μm, 50×20 mm; mobile phase: acetonitrile-water-0.1% TFA). After lyophilization, the product was obtained as a solid (25 mg, 76% of theory).

LC-MS (Method 5): $R_t$=1.54 min; MS (ESIpos): m/z (%)=612.1 (100) [M+H]$^+$; MS (ESIneg): m/z (%)=610.0 (100) [M−H]$^−$.

$^1$H-NMR (400 MHz, DMSO-d$_6$): δ=0.70 (m, 6H), 1.65 (m, 1H), 2.00 (s, 3H), 3.25 (d, 2H), 4.95 (d, 1H), 5.05 (d, 1H), 6.55 (s, 1H), 7.15-7.40 (m, 5H), 7.70-7.95 (m, 7H), 8.15 (br. s, 1H).

Example 44

Benzyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}(cyclopropylmethyl)carbamate

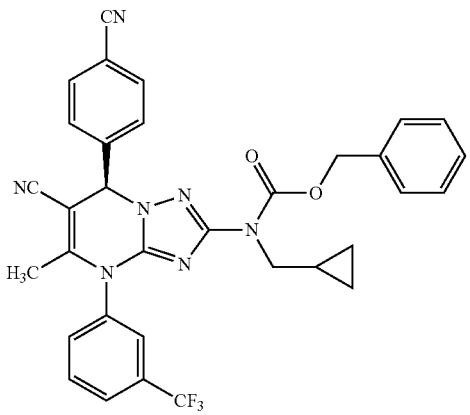 [SMILES: CC1=C(C#N)[C@@H](c2ccc(C#N)cc2)n2nc(N(CC3CC3)C(=O)OCc3ccccc3)nc2N1c1cccc(C(F)(F)F)c1]

Potassium carbonate (15.7 mg, 113 μmol, 2.1 eq.), 18-crown-6 (30 mg, 113 μmol, 2.1 eq.) and 1-(bromomethyl)cyclopropane (15.3 mg, 113 μmol, 2.1 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (30 mg, 54 μmol) in DMF (2 ml). The reaction mixture was stirred at RT for 12 h and then concentrated under reduced pressure. The residue was acidified with acetic acid and then purified by preparative HPLC (Kromasil C18 column, 5 μm, 50×20 mm; mobile phase: acetonitrile-water-0.1% TFA). After lyophilization, the product was obtained as a solid (22 mg, 66% of theory).

LC-MS (Method 5): $R_t$=1.50 min; MS (ESIpos): m/z (%)=610.1 (100) [M+H]$^+$; MS (ESIneg): m/z (%)=608.9 (100) [M−H]$^−$.

$^1$H-NMR (400 MHz, DMSO-$d_6$): δ=0.25 (m, 2H), 0.85 (m, 1H), 2.00 (s, 3H), 3.30 (m, 4H), 5.00 (d, 1H), 5.05 (d, 1H), 6.50 (s, 1H), 7.15-7.40 (m, 5H), 7.70-7.95 (m, 7H), 8.15 (br. s, 1H).

Example 45 tert-Butyl N-[(benzyloxy)carbonyl]-N-{(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}glycinate

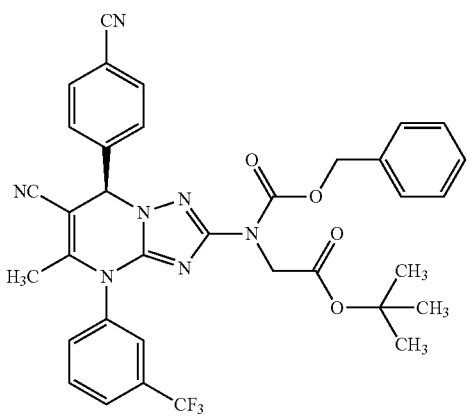 [SMILES: CC1=C(C#N)[C@@H](c2ccc(C#N)cc2)n2nc(N(CC(=O)OC(C)(C)C)C(=O)OCc3ccccc3)nc2N1c1cccc(C(F)(F)F)c1]

Potassium carbonate (8.0 mg, 58 μmol, 1.6 eq.) and tert-butyl bromoacetate (11.2 mg, 58 μmol, 1.6 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (20 mg, 36 μmol) in dry DMF (5 ml). The reaction mixture was stirred at RT for 12 h and then concentrated under reduced pressure, and the residue purified by preparative HPLC (Kromasil C18 column, 5 μm, 50×20 mm; mobile phase: acetonitrile-water-0.1% TFA). After lyophilization, the product was obtained as a solid (25 mg, 76% of theory).

LC-MS (Method 7): $R_t$=6.61 min; MS (ESIpos): m/z (%)=670.2 (100) [M+H]$^+$; MS (ESIneg): m/z (%)=668.2 (90) [M−H]$^−$.

$^1$H-NMR (400 MHz, DMSO-$d_6$): δ=1.15 (s, 9H), 2.00 (s, 3H), 4.10 (d, 1H), 4.15 (d, 1H), 5.10 (s, 2H), 6.45 (s, 1H), 7.20-7.30 (m, 5H), 7.70-7.95 (m, 7H), 8.15 (br. s, 1H).

Example 46

Ethyl {(7R)-6-cyano-7-(4-cyanophenyl)-5-methyl-4-[3-(trifluoromethyl)phenyl]-4,7-dihydro-[1,2,4]triazolo[1,5-a]pyrimidin-2-yl}carbamate

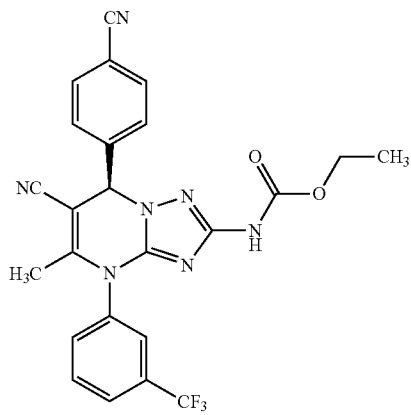 [SMILES: CCOC(=O)Nc1nc2n(n1)[C@H](c1ccc(C#N)cc1)C(C#N)=C(C)N2c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile (25 mg, 59 μmol) was dissolved in a mixture of abs. THF (2.5 ml) and abs. pyridine (48 ml). At room temperature, ethyl chloroformate (32 mg, 297 μmol, 5 eq.) was added and the mixture was heated at 80° C. for 12 h. Once HPLC analysis showed substantial conversion, the reaction mixture was concentrated under reduced pressure and purified by preparative HPLC (Reprosil C18 column, 30×250 mm; mobile phase: acetonitrile-water-0.1% TFA). After lyophilization, the product was obtained as a solid (25 mg, 86% of theory).

LC-MS (Method 7): $R_t$=1.97 min; MS (ESIpos): m/z (%)=494.2 (100) [M+H]$^+$; MS (ESIneg): m/z (%)=492.3 (100) [M−H]$^−$.

$^1$H-NMR (400 MHz, DMSO-$d_6$): δ=1.10 (t, 3H), 2.00 (s, 3H), 3.95 (q, 2H), 6.40 (s, 1H), 7.75-7.95 (m, 7H), 8.20 (br. s, 1H), 9.95 (s, 1H).

Example 47

1-Methylethyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate

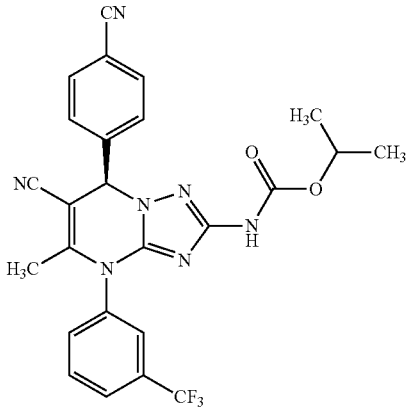 [SMILES: CC1=C(C#N)[C@@H](c2ccc(C#N)cc2)n2nc(NC(=O)OC(C)C)nc2N1c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile (25 mg, 59 µmol) was dissolved in a mixture of abs. THF (2.5 ml) and abs. pyridine (48 µl, 593 µmol, 10 eq.). At room temperature, isopropyl chloroformate (36 mg, 297 µmol, 5 eq.) was added and the mixture was heated at 80° C. for 12 h. Once HPLC analysis showed substantial conversion, the reaction mixture was concentrated under reduced pressure and purified by preparative HPLC (Reprosil C18 column, 30×250 mm; mobile phase: acetonitrile-water-0.1% TFA). After lyophilization, the product was obtained as a solid (23.2 mg, 77% of theory).

LC-MS (Method 7): $R_t$=2.08 min; MS (ESIpos): m/z (%)=508.3 (100) [M+H]$^+$; MS (ESIneg): m/z (%)=506.3 (100) [M−H]$^−$.

$^1$H-NMR (400 MHz, DMSO-$d_6$): δ=1.10 (dd, 6H), 1.95 (s, 3H), 4.70 (hept, 1H), 6.40 (s, 1H), 7.75-7.95 (m, 7H), 8.20 (br. s, 1H), 9.85 (s, 1H).

Example 48

Ethyl 7-(4-cyanophenyl)-2-[(methoxycarbonyl)amino]-5-methyl-4-[3-(trifluoromethyl)phenyl]-4,7-dihydro[1,2,4]triazolo[1,5-a]pyrimidine-6-carboxylate

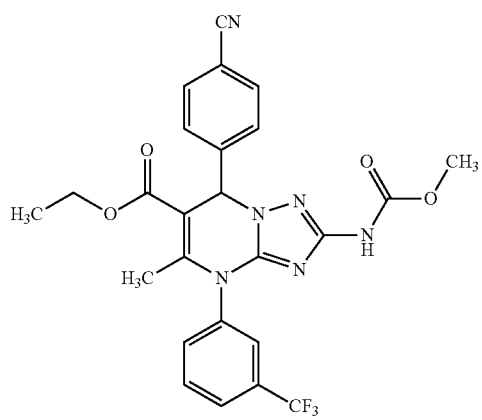 [SMILES: CCOC(=O)C1=C(C)N(c2cccc(C(F)(F)F)c2)c2nc(NC(=O)OC)nn2C1c1ccc(C#N)cc1]

Under an atmosphere of argon protective gas, ethyl 2-amino-7-(4-cyanophenyl)-5-methyl-4-[3-(trifluoromethyl)phenyl]-4,7-dihydro[1,2,4]triazolo[1,5-a]pyrimidine-6-carboxylate (10 mg, 21 µmol) was dissolved in a mixture of abs. THF (3 ml) and abs. pyridine (3 ml). At 0° C., methyl chloroformate (17 mg, 180 µmol, 8.5 eq.) was added in two portions and the mixture was stirred for 12 h with warming to RT. Once HPLC analysis showed substantial conversion, the reaction mixture was concentrated under reduced pressure and purified by preparative HPLC (Gromsil C18 column, 30×250 mm; mobile phase: acetonitrile-water-0.1% TFA). After lyophilization, the product was obtained as a solid (10.8 mg, 96% of theory).

LC-MS (Method 2): $R_t$=2.59 min; MS (ESIpos): m/z (%)=527.2 (100) [M+H]$^+$; MS (ESIneg): m/z (%)=525.1 (100) [M−H]$^−$.

Example 49

Ethyl 2-[(benzyloxy)carbonyl]amino-7-(4-cyanophenyl)-5-methyl-4-[3-(trifluoromethyl)phenyl]-4,7-dihydro[1,2,4]triazolo[1,5-a]pyrimidine-6-carboxylate

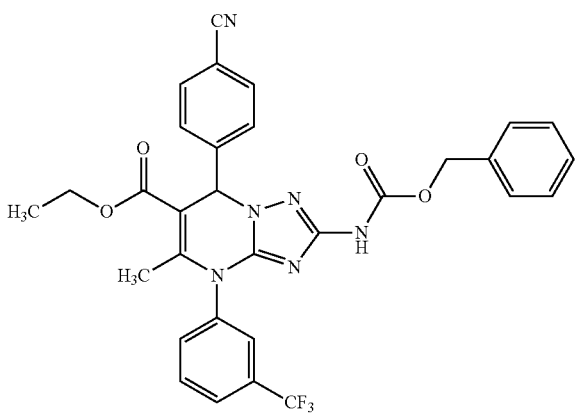 [SMILES: CCOC(=O)C1=C(C)N(c2cccc(C(F)(F)F)c2)c2nc(NC(=O)OCc3ccccc3)nn2C1c1ccc(C#N)cc1]

Under an atmosphere of argon protective gas, ethyl 2-amino-7-(4-cyanophenyl)-5-methyl-4-[3-(trifluoromethyl)phenyl]-4,7-dihydro[1,2,4]triazolo[1,5-a]pyrimidine-6-carboxylate (130 mg, 278 µmol) was dissolved in abs. pyridine (3.6 ml). At 0° C., benzyl chloroformate (379 mg, 2.2 mmol, 8 eq.) was added in four portions and the mixture was stirred for 12 h with warming to RT. Once HPLC analysis showed substantial conversion, the reaction mixture was concentrated under reduced pressure, and the residue was taken up in acetonitrile, acidified with 1 N hydrochloric acid and then purified by preparative HPLC (Gromsil C18 column, 30×250 mm; mobile phase: acetonitrile-water-0.1% TFA). After lyophilization, the product was obtained as a solid (146.3 mg, 87% of theory).

LC-MS (Method 4): $R_t$=3.94 min; MS (ESIpos): m/z (%)=603.2 (100) [M+H]$^+$; MS (ESIneg): m/z (%)=602.3 (100) [M−H]$^−$.

$^1$H-NMR (400 MHz, DMSO-$d_6$): δ=1.00 (t, 3H), 2.15 (s, 3H), 3.95 (q, 2H), 5.00 (s, 2H), 6.40 (s, 1H), 7.20-7.35 (m, 5H), 7.70-7.95 (m, 7H), 8.15 (br. s, 1H), 10.05 (s, 1H).

Example 50

Ethyl 7-(4-cyanophenyl)-2-[(ethoxycarbonyl)amino]-5-methyl-4-[3-(trifluoromethyl)phenyl]-4,7-dihydro[1,2,4]triazolo[1,5-a]pyrimidine-6-carboxylate

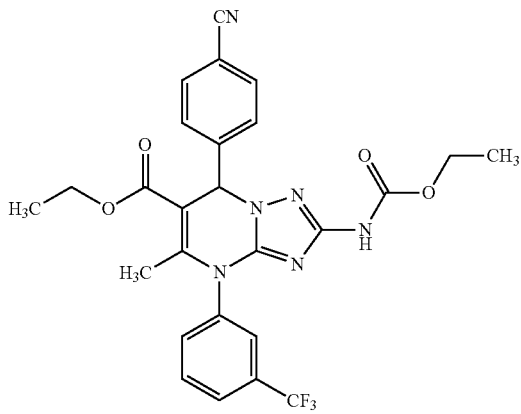 [SMILES: CCOC(=O)Nc1nc2n(n1)C(c1ccc(C#N)cc1)C(C(=O)OCC)=C(C)N2c1cccc(C(F)(F)F)c1]

Under an atmosphere of argon protective gas, ethyl 2-[(benzyloxy)carbonyl]amino-7-(4-cyanophenyl)-5-methyl-4-[3-(trifluoromethyl)phenyl]-4,7-dihydro[1,2,4]triazolo[1,5-a]pyrimidine-6-carboxylate (125 mg, 207 µmol) was dissolved in a mixture of THF (0.9 ml), water (0.6 ml) and ethanol (3.8 ml). After addition of solid lithium hydroxide (14.9 mg, 620 µmol, 3 eq.), the reaction mixture was heated at 55 C for 1.5 h. In an ice-bath, the mixture was acidified with 1 N hydrochloric acid (4.1 ml) and then purified by preparative HPLC (Kromasil C18 column, 30×250 mm; mobile phase: acetonitrile-water-0.1% TFA). After lyophilization, the product was obtained as a solid (4.8 mg, 5% of theory).

LC-MS (Method 2): $R_t$=2.70 min; MS (ESIpos): m/z (%)=541.1 (100) [M+H]$^+$; MS (ESIneg): m/z (%)=539.2 (100) [M−H]$^-$.

$^1$H-NMR (400 MHz, DMSO-d$_6$): δ=1.00 (t, 3H), 1.10 (t, 3H), 2.15 (s, 3H), 3.95 (2q, 4H), 6.40 (s, 1H), 7.70-7.95 (m, 7H), 8.15 (br. s, 1H), 9.85 (s, 1H).

Example 51

1-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}-3-methylurea

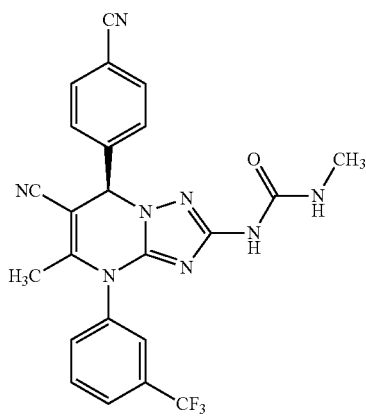

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile (13 mg, 28 µmol) was initially charged in abs. dichloromethane (2 ml). At −78° C., 4-nitrophenyl chloroformate (28.6 mg, 142 µmol, 5 eq.), triethylamine (14.7 mg, 145 µmol, 5.1 eq.) and DMAP (3.5 mg, 28 µmol) were added. After 2 h of stirring at −78° C., the reaction mixture was allowed to thaw initially to −20° C. (2 h) and then to 0° C. (2 h). The mixture was then once more cooled to −78° C., and a 2 M solution of methylamine in THF (102 µl, 7.2 eq.) was added. The mixture was then warmed to −10° C. and stirred overnight. A 2 M solution of methylamine in THF (1 ml) was then added, the reaction mixture was concentrated under reduced pressure and the residue was purified by preparative HPLC (Reprosil C18 column, 30×250 mm; mobile phase: acetonitrile-water-0.1% TFA). After lyophilization, the product was obtained as a solid (5.9 mg, 43% of theory).

LC-MS (Method 2): $R_t$=2.25 min; MS (ESIpos): m/z (%)=479.0 (100) [M+H]$^+$; MS (ESIneg): m/z (%)=477.1 (100) [M−H]$^-$.

Example 52

1-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}-3-ethylurea

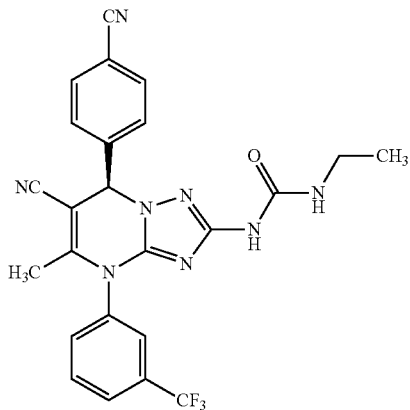 [SMILES: CCNC(=O)Nc1nc2n(n1)[C@H](c1ccc(C#N)cc1)C(C#N)=C(C)N2c1cccc(C(F)(F)F)c1]

Under an atmosphere of argon protective gas, (7R)-2-amino-7-(4-cyanophenyl)-5-methyl-4-[3-(trifluoromethyl)phenyl]-4,7-dihydro[1,2,4]triazolo[1,5-a]pyrimidine-6-carbonitrile (15 mg, 33 µmol) was dissolved in abs. pyridine (2 ml), and solid sodium sulfate (spatula tip) and ethyl isocyanate (46.6 mg, 655 µmol, 20 eq.) were added. The reaction mixture was then heated in a microwave reactor (2.5 h at 100° C., then 2 h at 110° C. and finally 2 h at 125° C.). After cooling, the reaction mixture was filtered, the filtrate was concentrated under reduced pressure and the residue was purified by preparative HPLC (Gromsil C18 column, 30×250 mm; mobile phase: acetonitrile-water-0.1% TFA). After lyophilization, the product was obtained as a solid (7.8 mg, 48% of theory).

LC-MS (Method 2): $R_t$=2.34 min; MS (ESIpos): m/z (%)=493.2 (100) [M+H]$^+$; MS (ESIneg): m/z (%)=491.2 (100) [M−H]$^-$.

$^1$H-NMR (400 MHz, DMSO-d$_6$): δ=0.80 (t, 3H), 2.00 (s, 3H), 2.95 (m, 2H), 6.40 (s, 1H), 7.15 (t, 1H), 7.75-7.95 (m, 7H), 8.20 (br. s, 1H), 9.35 (s, 1H).

Example 53

1-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}-3-(2-hydroxyethyl)urea

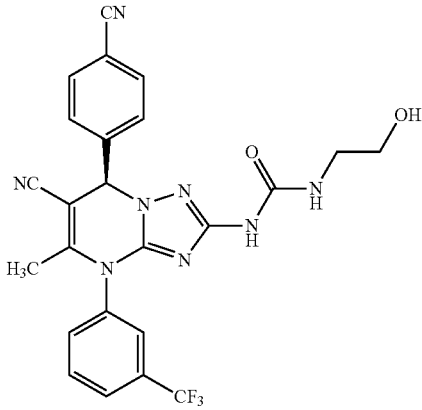 [SMILES: CC1=C(C#N)[C@@H](c2ccc(C#N)cc2)n2nc(NC(=O)NCCO)nc2N1c1cccc(C(F)(F)F)c1]

Under an atmosphere of argon protective gas and at 0° C., 4-nitrophenyl chloroformate (7.3 mg, 36 µmol, 2 eq.), triethylamine (3.1 mg, 40 µmol, 2.2 eq.) and DMAP (0.2 mg, 1.8 µmol, 0.1 eq.) were added to a solution of benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}carbamate (10 mg, 18 µmol) in dry dichloromethane (1 ml), and the mixture was stirred at 4° C. for 12 h. At 0° C., 2-aminoethanol (8.5 mg, 139 µmol, 10 eq.) was then added, and the mixture was once more stirred at 4° C. for 12 h. The reaction mixture was then concentrated under reduced pressure and purified by preparative HPLC (Gromsil C18 column, 30×250 mm; mobile phase: acetonitrile-water-0.1% TFA). After lyophilization, the product was obtained as a solid (1.9 mg, 27% of theory).

LC-MS (Method 5): $R_t$=1.08 min; MS (ESIpos): m/z (%)=509.2 (100) [M+H]$^+$; MS (ESIneg): m/z (%)=507.5 (100) [M–H]$^-$.

Example 54

N-{(7R)-6-Cyano-7-(4-cyanophenyl)-5-methyl-4-[3-(trifluoromethyl)phenyl]-4,7-dihydro[1,2,4]triazolo[1,5-a]pyrimidin-2-yl}methanesulfonamide

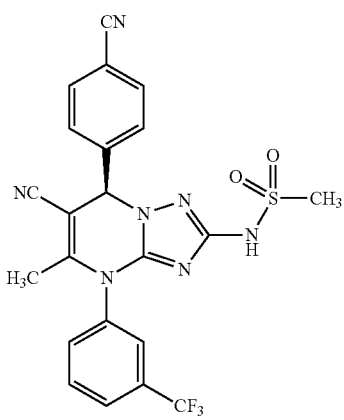

Under an atmosphere of argon protective gas, benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}(methylsulfonyl)carbamate (16.0 mg, 11 µmol) was dissolved in degassed methanol (2 ml). After addition of a catalytic amount of palladium on activated carbon (10%), the mixture was hydrogenated under a hydrogen atmosphere (~1 atm) at RT for 0.5 h. The reaction mixture was then filtered, the filtrate was concentrated under reduced pressure and the residue was purified by preparative HPLC (Gromsil C18 column, 30×250 mm; mobile phase: acetonitrile-water-0.1% TFA). After lyophilization, the product was obtained as a solid (8.5 mg, 71% of theory).

LC-MS (Method 5): $R_t$=1.17 min; MS (ESIpos): m/z (%)=500.1 (100) [M+H]$^+$; MS (ESIneg): m/z (%)=499.6 (100) [M–H]$^-$.

$^1$H-NMR (400 MHz, DMSO-d$_6$): δ=2.00 (s, 3H), 3.00 (s, 3H), 6.45 (s, 1H), 7.75-7.95 (m, 7H), 8.20 (br. s, 1H), 10.75 (s, 1H).

Example 55

(7R)-7-(4-Cyanophenyl)-5-methyl-2-(methylamino)-4-[3-(trifluoromethyl)phenyl]-4,7-dihydro-[1,2,4]triazolo[1,5-a]pyrimidine-6-carbonitrile

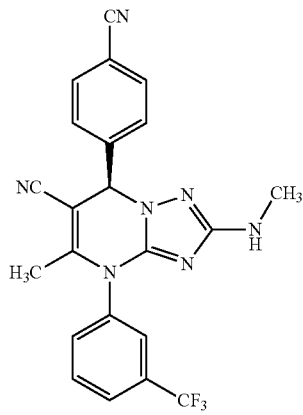

Under an atmosphere of argon protective gas, benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}methylcarbamate (13.0 mg, 23 µmol) was dissolved in degassed methanol (2 ml). After addition of a catalytic amount of palladium on activated carbon (10%), the mixture was hydrogenated under a hydrogen atmosphere (~1 atm) at RT for 2 h. The reaction mixture was then filtered, the filtrate was concentrated under reduced pressure and the residue was purified by preparative HPLC (Kromasil C18 column, 50×20 mm; mobile phase: acetonitrile-water-0.1% TFA). After lyophilization, the product was obtained as a solid (8.2 mg, 83% of theory).

LC-MS (Method 7): $R_t$=1.92 min; MS (ESIpos): m/z (%)=436.3 (100) [M+H]$^+$; MS (ESIneg): m/z (%)=434.2 (100) [M–H]$^-$.

$^1$H-NMR (400 MHz, DMSO-d$_6$): δ=2.00 (s, 3H), 2.45 (s, 3H), 6.00 (br. s, 1H), 6.20 (s, 1H), 7.75-7.95 (m, 7H), 8.15 (br. s, 1H).

Example 56

(7R)-7-(4-Cyanophenyl)-2-(ethylamino)-5-methyl-4-[3-(trifluoromethyl)phenyl]-4,7-dihydro-[1,2,4]triazolo[1,5-a]pyrimidine-6-carbonitrile

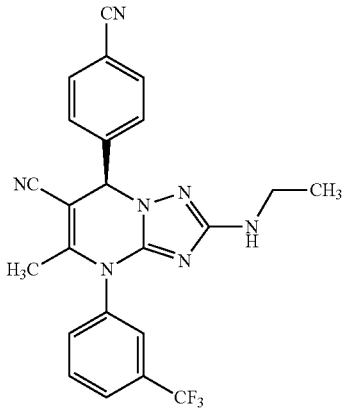 [SMILES: CCNc1nc2n(n1)[C@H](c1ccc(C#N)cc1)C(C#N)=C(C)N2c1cccc(C(F)(F)F)c1]

Under an atmosphere of argon protective gas, benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}(ethyl)carbamate (17.0 mg, 29 µmol) was dissolved in degassed methanol (2 ml). After addition of palladium on activated carbon (10%; 2 mg), the mixture was hydrogenated under a hydrogen atmosphere (~1 atm) at RT for 1 h. The reaction mixture was then filtered, the filtrate was concentrated under reduced pressure and the residue was purified by preparative HPLC (Kromasil C18 column, 50×20 mm; mobile phase: acetonitrile-water-0.1% TFA). After lyophilization, the product was obtained as a solid (10.9 mg, 83% of theory).

LC-MS (Method 2): $R_t$=2.40 min; MS (ESIpos): m/z (%)=450.1 (100) [M+H]$^+$; MS (ESIneg): m/z (%)=448.0 (100) [M−H]$^−$.

$^1$H-NMR (400 MHz, DMSO-d$_6$): δ=0.95 (t, 3H), 1.95 (s, 3H), 2.85 (m, 2H), 6.05 (br. s, 1H), 6.20 (s, 1H), 7.70-7.95 (m, 7H), 8.15 (br. s, 1H).

Example 57

(7R)-2-[(Cyanomethyl)amino]-7-(4-cyanophenyl)-5-methyl-4-[3-(trifluoromethyl)phenyl]-4,7-dihydro[1,2,4]triazolo[1,5-a]pyrimidine-6-carbonitrile

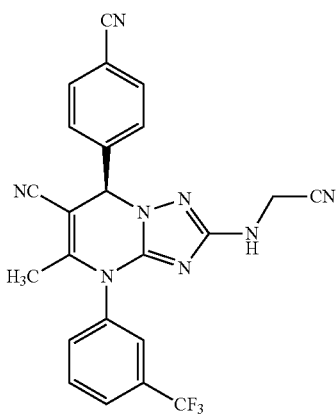 [SMILES: CC1=C(C#N)[C@@H](c2ccc(C#N)cc2)n2nc(NCC#N)nc2N1c1cccc(C(F)(F)F)c1]

Under an atmosphere of argon protective gas, benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}(cyanomethyl)-carbamate (10.0 mg, 17 µmol) was dissolved in degassed methanol (3 ml). After addition of palladium on activated carbon (10%; 2 mg), the mixture was hydrogenated under a hydrogen atmosphere (~1 atm) at RT for 0.5 h. The reaction mixture was then filtered, the filtrate was concentrated under reduced pressure and the residue was purified by preparative HPLC (Kromasil C18 column, 50×20 mm; mobile phase: acetonitrile-water-0.1% TFA). After lyophilization, the product was obtained as a solid (7.4 mg, 96% of theory).

LC-MS (Method 7): $R_t$=1.98 min; MS (ESIpos): m/z (%)=461.1 (100) [M+H]$^+$; MS (ESIneg): m/z (%)=459.1 (100) [M−H]$^−$.

$^1$H-NMR (400 MHz, DMSO-d$_6$): δ=1.95 (s, 3H), 3.90 (m, 2H), 6.30 (s, 1H), 6.90 (br. t, 1H), 7.70-7.95 (m, 7H), 8.15 (br. s, 1H).

Example 58

(7R)-7-(4-Cyanophenyl)-5-methyl-2-(propylamino)-4-[3-(trifluoromethyl)phenyl]-4,7-dihydro-[1,2,4]triazolo[1,5-a]pyrimidine-6-carbonitrile

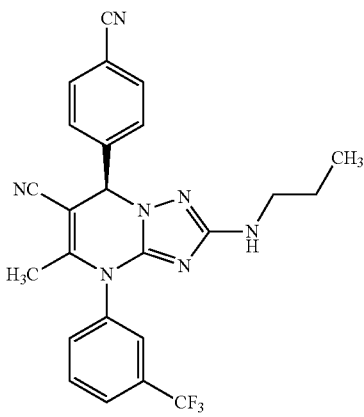 [SMILES: CCCNc1nc2n(n1)[C@H](c1ccc(C#N)cc1)C(C#N)=C(C)N2c1cccc(C(F)(F)F)c1]

Under an atmosphere of argon protective gas, benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}(propyl)carbamate (17.0 mg, 28 µmol) was dissolved in degassed methanol (5 ml). After addition of palladium on activated carbon (10%; 5 mg), the mixture was hydrogenated under a hydrogen atmosphere (~1 atm) at RT for 0.5 h. The reaction mixture was then filtered, the filtrate was concentrated under reduced pressure and the residue was purified by preparative HPLC (Kromasil C18 column, 50×20 mm; mobile phase: acetonitrile-water-0.1% TFA). After lyophilization, the product was obtained as a solid (10.7 mg, 81% of theory).

LC-MS (Method 7): $R_t$=2.19 min; MS (ESIpos): m/z (%)=464.2 (100) [M+H]$^+$; MS (ESIneg): m/z (%)=462.2 (100) [M−H]$^−$.

$^1$H-NMR (400 MHz, DMSO-d$_6$): δ=0.70 (t, 3H), 1.35 (m, 2H), 1.95 (s, 3H), 2.75 (m, 2H), 6.10 (br. s, 1H), 6.20 (s, 1H), 7.70-7.95 (m, 7H), 8.15 (br. s, 1H).

Example 59

(7R)-7-(4-Cyanophenyl)-5-methyl-2-[(2-methylpropyl)amino]-4-[3-(trifluoromethyl)phenyl]-4,7-dihydro[1,2,4]triazolo[1,5-a]pyrimidine-6-carbonitrile

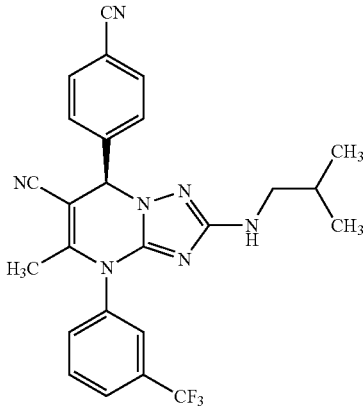

Under an atmosphere of argon protective gas, benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}(2-methylpropyl)-carbamate (25.0 mg, 41 μmol) was dissolved in degassed methanol (5 ml). After addition of palladium on activated carbon (10%; 5 mg), the mixture was hydrogenated under a hydrogen atmosphere (~1 atm) at RT for 0.75 h. The reaction mixture was then filtered, the filtrate was concentrated under reduced pressure and the residue was purified by preparative HPLC (Kromasil C18 column, 50×20 mm; mobile phase: acetonitrile-water-0.1% TFA). After lyophilization, the product was obtained as a solid (13.6 mg, 70% of theory).

LC-MS (Method 7): $R_t$=2.32 min; MS (ESIpos): m/z (%)=478.1 (100) [M+H]$^+$; MS (ESIneg): m/z (%)=476.2 (100) [M−H]$^−$.

$^1$H-NMR (400 MHz, DMSO-d$_6$): δ=0.70 (m, 6H), 1.65 (m, 1H), 1.95 (s, 3H), 2.65 (m, 2H), 6.15 (br. s, 1H), 6.20 (s, 1H), 7.65-7.95 (m, 7H), 8.15 (br. s, 1H).

Example 60

(7R)-7-(4-Cyanophenyl)-2-[(cyclopropylmethyl)amino]-5-methyl-4-[3-(trifluoromethyl)phenyl]-4,7-dihydro[1,2,4]triazolo[1,5-a]pyrimidine-6-carbonitrile

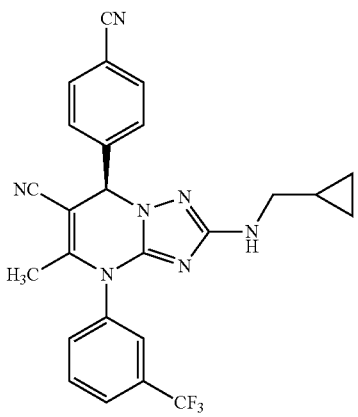 [SMILES: CC1=C(C#N)[C@@H](c2ccc(C#N)cc2)n2nc(NCC3CC3)nc2N1c1cccc(C(F)(F)F)c1]

Under an atmosphere of argon protective gas, benzyl {(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}(cyclopropylmethyl)carbamate (20.0 mg, 33 μmol) was dissolved in degassed methanol (5 ml). After addition of palladium on activated carbon (10%; 5 mg), the mixture was hydrogenated under a hydrogen atmosphere (~1 atm) at RT for 1.75 h. The reaction mixture was then filtered, the filtrate was concentrated under reduced pressure and the residue was purified by preparative HPLC (Kromasil C18 column, 50×20 mm; mobile phase: acetonitrile-water-0.1% TFA). After lyophilization, the product was obtained as a solid (10.9 mg, 70% of theory).

LC-MS (Method 7): $R_t$=2.21 min; MS (ESIpos): m/z (%)=476.1 (100) [M+H]$^+$; MS (ESIneg): m/z (%)=474.2 (100) [M−H]$^−$.

$^1$H-NMR (400 MHz, DMSO-d$_6$): δ=0.05 (m, 2H), 0.25 (m, 2H), 0.80 (m, 1H), 1.95 (s, 3H), 2.65-2.80 (m, 2H), 6.15 (br. s, 1H), 6.20 (s, 1H), 7.65-7.95 (m, 7H), 8.15 (br. s, 1H).

Example 61 tert-Butyl N-{(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}glycinate

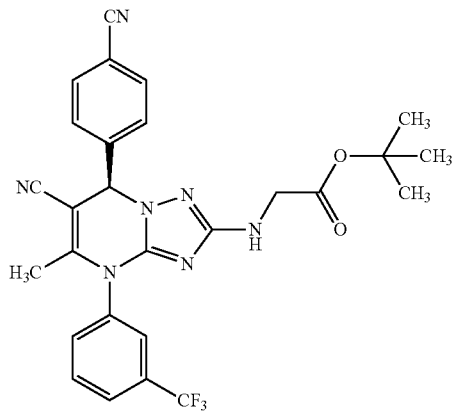 [SMILES: CC1=C(C#N)[C@@H](c2ccc(C#N)cc2)n2nc(NCC(=O)OC(C)(C)C)nc2N1c1cccc(C(F)(F)F)c1]

Under an atmosphere of argon protective gas, tert-butyl N-[(benzyloxy)carbonyl]-N-{(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}glycinate (23.0 mg, 34 μmol) was dissolved in degassed methanol (2.3 ml). After addition of palladium on activated carbon (10%-ig; 15.2 mg), the mixture was hydrogenated under a hydrogen atmosphere (~1 atm) at RT for 0.5 h. The reaction mixture was then filtered, the filtrate was concentrated under reduced pressure and the residue was purified by preparative HPLC (Kromasil C18 column, 50×20 mm; mobile phase: acetonitrile-water-0.1% TFA). After lyophilization, the product was obtained as a solid (21.2 mg, quant.).

LC-MS (Method 7): $R_t$=2.25 min; MS (ESIpos): m/z (%)=480.3 (100), 536.3 (80) [M+H]$^+$; MS (ESIneg): m/z (%)=534.3 (100) [M−H]$^−$.

$^1$H-NMR (400 MHz, DMSO-d$_6$): δ=1.15 (s, 9H), 1.95 (s, 3H), 3.45 (m, 2H), 6.20 (s, 1H), 6.45 (br. t, 1H), 7.65-7.95 (m, 7H), 8.15 (br. s, 1H).

Example 62

N-{(7R)-6-Cyano-7-(4-cyanophenyl)-5-methyl-4-[3-(trifluoromethyl)phenyl]-4,7-dihydro[1,2,4]-triazolo[1,5-a]pyrimidin-2-yl}glycine

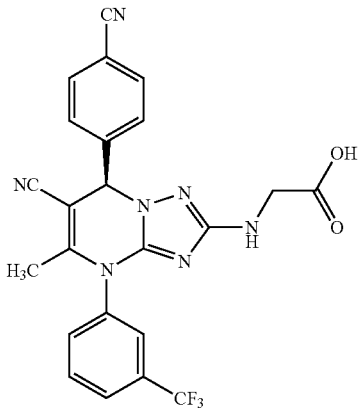 [SMILES: CC1=C(C#N)[C@@H](c2ccc(C#N)cc2)n2nc(NCC(=O)O)nc2N1c1cccc(C(F)(F)F)c1]

Under an atmosphere of argon protective gas, tert-butyl N-{(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}glycinate (18.0 mg, 34 µmol) was dissolved in dry dichloromethane (3.1 ml). At room temperature, trifluoroacetic acid (1.6 ml) was added, and the mixture was stirred for 45 min. More trifluoroacetic acid (2 ml) was then added, and the mixture was stirred for a further 30 min. The reaction mixture was then concentrated under reduced pressure and the residue was purified by preparative HPLC (Gromsil C18 column, 30×250 mm; mobile phase: acetonitrile-water-0.1% TFA). After lyophilization, the product was obtained as a solid (15.2 mg, 94% of theory).

LC-MS (Method 7): $R_t$=1.78 min; MS (ESIpos): m/z (%)=480.2 (100) [M+H]$^+$; MS (ESIneg): m/z (%)=478.2 (100) [M−H]$^-$.

$^1$H-NMR (400 MHz, DMSO-d$_6$): δ=1.95 (s, 3H), 3.55 (s, 2H), 6.20 (s, 1H), 6.40 (br. t, 1H), 7.65-7.95 (m, 7H), 8.15 (br. s, 1H), 12.30 (br. s, 1H).

Example 63

N$^2$-{(7R)-6-Cyano-7-(4-cyanophenyl)-5-methyl-4-[3-(trifluoromethyl)phenyl]-4,7-dihydro-[1,2,4]triazolo[1,5-a]pyrimidin-2-yl}glycinamide

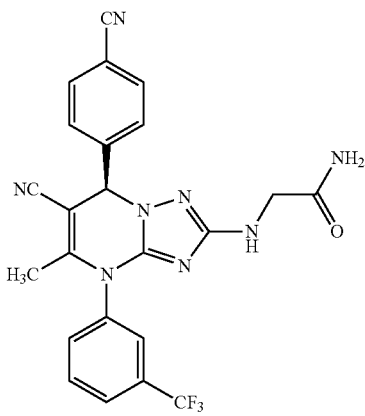 [SMILES: CC1=C(C#N)[C@@H](c2ccc(C#N)cc2)n2nc(NCC(N)=O)nc2N1c1cccc(C(F)(F)F)c1]

Under an atmosphere of argon protective gas and at 0° C., HATU (25 mg, 66 µmol, 3 eq.) and triethylamine (11 mg, 110 µmol, 5 eq.) were added to a solution of N-{(7R)-6-cyano-7-(4-cyanophenyl)-5-methyl-4-[3-(trifluoromethyl)phenyl]-4,7-dihydro[1,2,4]triazolo[1,5-a]pyrimidin-2-yl}glycine (10.5 mg, 22 µmol) in DMF (1 ml). After the reaction mixture has thawed to RT, it was once more cooled to 0° C., and a 0.5 M solution of ammonia in dioxane (0.44 ml, 219 µmol, 10 eq.) was then added. The mixture was stirred for 2 h, during which time it gradually warmed to RT. The reaction mixture was then concentrated under reduced pressure and the residue was purified by preparative HPLC (Kromasil C18 column, 50×20 mm; mobile phase: acetonitrile-water-0.1% TFA). After lyophilization, the product was obtained as a solid (9.2 mg, 88% of theory).

LC-MS (Method 5): $R_t$=1.07 min; MS (ESIpos): m/z (%)=479.2 (100) [M+H]$^+$; MS (ESIneg): m/z (%)=477.5 (100) [M−H]$^-$.

$^1$H-NMR (400 MHz, DMSO-d$_6$): δ=1.95 (s, 3H), 3.40 (d, 2H), 6.25 (s, 1H), 6.90 (br. s, 1H), 7.05 (br. s, 1H), 7.65-7.95 (m, 8H), 8.15 (br. s, 1H).

Example 64

N$^2$-{(7R)-6-Cyano-7-(4-cyanophenyl)-5-methyl-4-[3-(trifluoromethyl)phenyl]-4,7-dihydro[1,2,4]-triazolo[1,5-a]pyrimidin-2-yl}-N,N-dimethylglycinamide

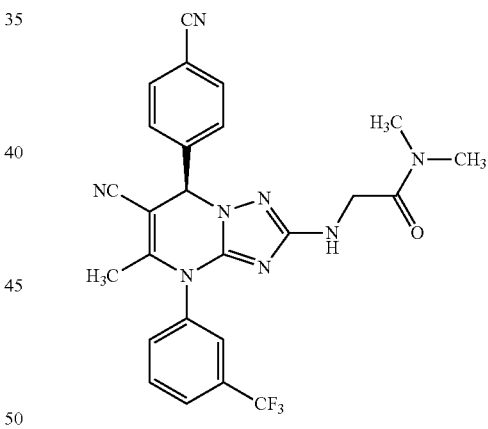

The title compound was obtained as a byproduct in the preparation of the compound from Example 63 and separated off during the HPLC purification described therein. After lyophilization of the appropriate fractions, 1 mg (9% of theory) was obtained as a solid.

LC-MS (Method 5): $R_t$=1.15 min; MS (ESIpos): m/z (%)=507.2 (100) [M+H]$^+$; MS (ESIneg): m/z (%)=505.1 (100) [M−H]$^-$.

$^1$H-NMR (400 MHz, DMSO-d$_6$): δ=1.95 (s, 3H), 2.75 (s, 3H), 2.85 (s, 3H), 3.65 (d, 1H), 3.70 (d, 1H), 5.80 (br. s, 1H), 6.25 (s, 1H), 7.65-7.95 (m, 7H), 8.15 (br. s, 1H).

Example 65

(rac)-7-(4-Cyanophenyl)-2-(methoxymethyl)-5-methyl-4-[3-(trifluoromethyl)phenyl]-4,7-dihydro-[1,2,4]triazolo[1,5-a]pyrimidine-6-carbonitrile

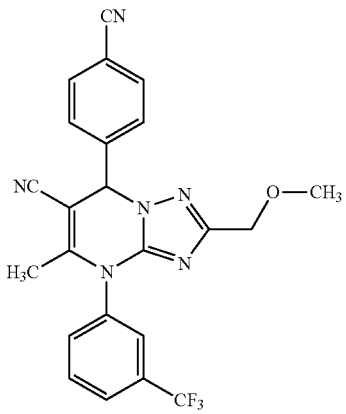

Under an atmosphere of argon protective gas, (rac)-7-(4-cyanophenyl)-2-(methoxymethyl)-5-methyl-4,7-dihydro[1,2,4]triazolo[1,5-a]pyrimidine-6-carbonitrile (35 mg, 114 µmol) was stirred in abs. dichloromethane (30 ml) with molecular sieve (0.5 g, 4 Å) for 1 h. 3-(Trifluoromethyl)phenylboronic acid (65 mg, 343 µmol, 3 eq.), anhydrous copper(II) acetate (62.3 mg, 343 µmol, 3 eq.), abs. pyridine (25 µl) and triethylamine (35 mg, 343 µmol, 3 eq.) were then added, and the mixture was stirred at RT for 12 h. More molecular sieve (0.5 g, 4 Å), 3-(trifluoromethyl)phenylboronic acid (22 mg, 114 µmol, 1 eq.), anhydrous copper(II) acetate (21 mg, 114 µmol, 1 eq.) and abs. pyridine (829 µl) were then added, and the mixture was stirred at RT for a further 3 d. The reaction mixture was then filtered through kieselguhr, the filter residue was washed with dichloromethane and pyridine and the filtrate was concentrated to dryness. The residue was purified by preparative HPLC (Gromsil C18 column, 10 µm; mobile phase: acetonitrile/water+0.1% TFA 10:90→90:10). The product was obtained as a colorless solid (4.4 mg, 9% of theory).

LC-MS (Method 8): $R_t$=2.18 min; MS (ESIpos): m/z (%)=451.3 (100) [M+H]$^+$; MS (ESIneg): m/z (%)=449.1 (100) [M−H]$^−$.

$^1$H-NMR (400 MHz, DMSO-d$_6$): δ=2.00 (s, 3H), 3.15 (s, 2H), 4.15 (s, 3H), 6.50 (s, 1H), 7.70-8.00 (m, 7H), 8.15 (br. s, 1H).

Example 66

(rac)-7-(4-Cyanophenyl)-5-methyl-2-thiophen-2-yl-4-[3-(trifluoromethyl)phenyl]-4,7-dihydro-[1,2,4]triazolo[1,5-a]pyrimidine-6-carbonitrile

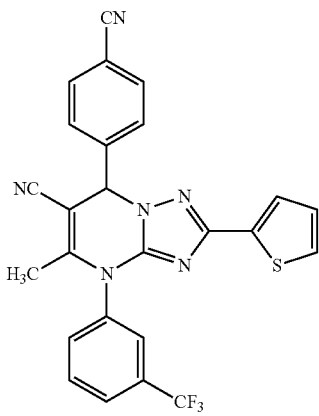 [SMILES: CC1=C(C#N)C(c2ccc(C#N)cc2)n2nc(-c3cccs3)nc2N1c1cccc(C(F)(F)F)c1]

Under an atmosphere of argon protective gas, (rac)-7-(4-cyanophenyl)-5-methyl-2-thiophen-2-yl-4,7-dihydro[1,2,4]triazolo[1,5-a]pyrimidine-6-carbonitrile (70 mg, 230 µmol) was stirred in abs. dichloromethane (60 ml) with molecular sieve (0.5 g, 4 Å) for 1 h. 3-(Trifluoromethyl)phenylboronic acid (131 mg, 690 µmol, 3 eq.), anhydrous copper(II) acetate (125 mg, 690 µmol, 3 eq.), abs. pyridine (1668 µl) and triethylamine (70 mg, 690 µmol, 3 eq.) were then added, and the mixture was stirred at RT for 12 h. More molecular sieve (0.5 g, 4 Å), 3-(trifluoromethyl)phenylboronic acid (44 mg, 230 µmol, 1 eq.), anhydrous copper(II) acetate (42 mg, 230 µmol, 1 eq.) and abs. pyridine (500 µl) were then added, and the mixture was stirred at RT for a further 3 d. The reaction mixture was then filtered through kieselguhr, the filter residue was washed with dichloromethane and pyridine and the filtrate was concentrated to dryness. The residue was purified by preparative HPLC (Gromsil C18 column, 10 µm; mobile phase: acetonitrile/water+0.1% TFA 10:90→90:10). The product was obtained as a colorless solid (40.1 mg, 36% of theory).

LC-MS (Method 8): $R_t$=2.52 min; MS (ESIpos): m/z (%)=489.2 (100) [M+H]$^+$; MS (ESIneg): m/z (%)=487.1 (100) [M−H]$^−$.

$^1$H-NMR (400 MHz, DMSO-d$_6$): δ=2.00 (s, 3H), 6.55 (s, 1H), 7.05 (m, 1H), 7.35 (m, 1H), 7.55 (m, 1H), 7.80-8.00 (m, 7H), 8.20 (br. s, 1H).

Example 67

(rac)-7-(4-Cyanophenyl)-5-methyl-2-(1-methylethyl)-4-[3-(trifluoromethyl)phenyl]-4,7-dihydro-[1,2,4]triazolo[1,5-a]pyrimidine-6-carbonitrile

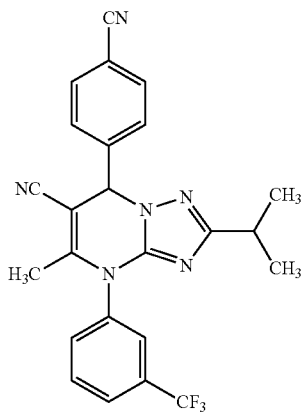 [SMILES: CC1=C(C#N)C(c2ccc(C#N)cc2)n2nc(C(C)C)nc2N1c1cccc(C(F)(F)F)c1]

Under an atmosphere of argon protective gas, (rac)-7-(4-cyanophenyl)-5-methyl-2-(1-methylethyl)-4,7-dihydro[1,2,4]triazolo[1,5-a]pyrimidine-6-carbonitrile (63 mg, 207 µmol) was stirred in abs. dichloromethane (50 ml) with molecular sieve (0.5 g, 4 Å) for 1 h. 3-(Trifluoromethyl)phenylboronic acid (118 mg, 621 µmol, 3 eq.), anhydrous copper(II) acetate (113 mg, 621 µmol, 3 eq.), abs. pyridine (1390 µl) and triethylamine (63 mg, 621 µmol, 3 eq.) were then added, and the mixture was stirred at RT for 12 h. More molecular sieve (0.5 g, 4 Å), 3-(trifluoromethyl)phenylboronic acid (39 mg, 207 µmol, 1 eq.), anhydrous copper(II) acetate (38 mg, 207 µmol, 1 eq.) and abs. pyridine (500 µl) were then added, and the mixture was stirred at RT for a further 3 d. The reaction mixture was then filtered through kieselguhr, the filter residue was washed with dichloromethane and pyridine and the filtrate was concentrated to dryness. The residue was purified by preparative HPLC (Gromsil C18 column, 10 µm; mobile phase: acetonitrile/water+0.1% TFA 10:90→90:10). The product was obtained as a colorless solid (29.8 mg, 64% of theory).

LC-MS (Method 8): $R_t$=2.44 min; MS (ESIpos): m/z (%)=449.3 (100) [M+H]$^+$; MS (ESIneg): m/z (%)=447.1 (70) [M−H]$^−$.

$^1$H-NMR (400 MHz, DMSO-d$_6$): δ=1.0 (m, 6H), 1.95 (s, 3H), 2.70 (m, 1H), 6.45 (s, 1H), 7.70-8.00 (m, 7H), 8.15 (br. s, 1H).

Example 68

(rac)-7-(4-Cyanophenyl)-2-methoxy-5-methyl-4-[3-(trifluoromethyl)phenyl]-4,7-dihydro[1,2,4]-triazolo[1,5-a]pyrimidine-6-carbonitrile

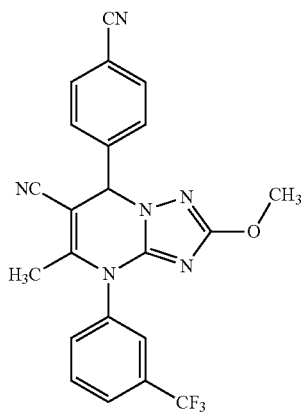

Under an atmosphere of argon protective gas, (rac)-7-(4-cyanophenyl)-2-methoxy-5-methyl-4,7-dihydro[1,2,4]triazolo[1,5-a]pyrimidine-6-carbonitrile (50 mg, 171 μmol) was stirred in abs. dichloromethane (7 ml) with molecular sieve (0.5 g, 4 Å) for 1 h. 3-(Trifluoromethyl)phenylboronic acid (97 mg, 513 μmol, 3 eq.), anhydrous copper(II) acetate (93 mg, 513 μmol, 3 eq.), abs. pyridine (8 ml) and triethylamine (72 μl, 513 μmol, 3 eq.) were then added, and the mixture was stirred at RT for 48 h. More anhydrous copper(II) acetate (31 mg, 171 μmol, 1 eq.) and 2,6-lutidine (60 μl, 513 μmol, 3 eq.) were then added, and the mixture was stirred under an atmosphere of dry air at RT for a further 7 d. The reaction mixture was then concentrated to dryness. The residue was suspended in ethyl acetate (10 ml) and filtered. The filtrate was washed with water (5 ml) and saturated sodium chloride solution, dried over sodium sulfate, filtered and concentrated under reduced pressure. The residue was purified by preparative HPLC (Reprosil C18 column, 10 μm; mobile phase: acetonitrile/water+0.1% TFA 10:90→90:10). The brown solid obtained in this manner was decolorized by filtration through a small silica gel cartridge using a mobile phase mixture of cyclohexane and ethyl acetate (2:1) and then lyophilized. The product was obtained as a solid (10.8 mg, 15% of theory).

LC-MS (Method 5): $R_t$=1.26 min; MS (ESIpos): m/z (%)=437.1 (100) [M+H]$^+$; MS (ESIneg): m/z (%)=435.2 (100) [M−H]$^−$.

$^1$H-NMR (400 MHz, DMSO-d$_6$): δ=1.95 (s, 3H), 3.65 (s, 3H), 6.35 (s, 1H), 7.70-8.00 (m, 7H), 8.15 (br. s, 1H).

Example 69

(rac)-4-(6-Acetyl-5-methyl-4-[3-(trifluoromethyl)phenyl]-4,7-dihydrotetrazolo[1,5-a]pyrimidin-7-yl)benzonitrile

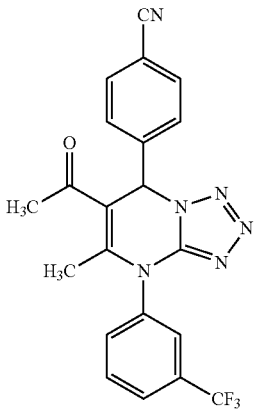 [SMILES: CC(=O)C1=C(C)N(c2cccc(C(F)(F)F)c2)c2nnnn2C1c1ccc(C#N)cc1]

Under an atmosphere of argon protective gas, (rac)-4-(6-acetyl-5-methyl-4,7-dihydrotetrazolo[1,5-a]pyrimidin-7-yl)benzonitrile (50 mg, 178 μmol) was stirred in abs. dichloromethane (3 ml) with molecular sieve (0.5 g, 4 Å) for 1 h. 3-(Trifluoromethyl)phenylboronic acid (101.6 mg, 535 μmol, 3 eq.), anhydrous copper(II) acetate (97.2 mg, 535 μmol, 3 eq.), abs. pyridine (115 μl, 1.43 mmol, 8 eq.) and triethylamine (54.2 mg, 535 μmol, 3 eq.) were then added, and the mixture was stirred at RT for 12 h. More molecular sieve (0.5 g, 4 Å), 3-(trifluoromethyl)phenylboronic acid (33 mg, 178 μmol, 1 eq.), anhydrous copper(II) acetate (32 mg, 178 μmol, 1 eq.), triethylamine (18.1 mg, 178 μmol, 1 eq.) and abs. pyridine (57.5 μl, 715 μmol, 4 eq.) were then added, and the mixture was stirred at RT for a further 12 h. The reaction mixture was then filtered through kieselguhr, the filter residue was washed with dichloromethane and methanol and the filtrate was concentrated to dryness. The residue was purified by preparative HPLC (Gromsil C18 column, 10 μm; mobile phase: acetonitrile/water+0.1% TFA 10:90→90:10). The product was obtained as a colorless solid (14.6 mg, 19% of theory).

LC-MS (Method 2): $R_t$=2.47 min; MS (ESIpos): m/z (%)=425.1 (100) [M+H]$^+$; MS (ESIneg): m/z (%)=423.1 (100) [M−H]$^−$.

$^1$H-NMR (400 MHz, DMSO-d$_6$): δ=2.10 (s, 3H), 2.20 (s, 3H), 7.10 (s, 1H), 7.80-8.00 (m, 7H), 8.20 (br. s, 1H).

Example 70

Ethyl (rac)-7-(4-cyanophenyl)-5-methyl-4-[3-(trifluoromethyl)phenyl]-4,7-dihydrotetrazolo[1,5-a]pyrimidine-6-carboxylate

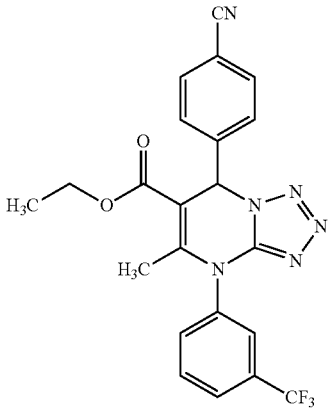 [SMILES: CCOC(=O)C1=C(C)N(c2cccc(C(F)(F)F)c2)c2nnnn2C1c1ccc(C#N)cc1]

Under an atmosphere of argon protective gas, ethyl (rac)-7-(4-cyanophenyl)-5-methyl-4,7-dihydrotetrazolo[1,5-a]pyrimidine-6-carboxylate (600 mg, 1.9 mmol) was stirred in abs. dichloromethane (450 ml) with molecular sieve (0.5 g, 4 Å) for 1 h. 3-(Trifluoromethyl)phenylboronic acid (1.10 g, 5.8 mmol, 3 eq.), anhydrous copper(II) acetate (1.05 g, 5.8 mmol, 3 eq.), abs. pyridine (1.25 ml, 15.5 mmol, 8 eq.) and triethylamine (0.59 g, 5.8 mmol, 3 eq.) were then added, and the mixture was stirred at RT for 12 h. More molecular sieve (0.5 g, 4 Å), 3-(trifluoromethyl)phenylboronic acid (0.37 g, 1.9 mmol, 1 eq.), anhydrous copper(II) acetate (0.35 g, 1.9 mmol, 1 eq.) and abs. pyridine (0.63 ml, 7.73 mmol, 4 eq.) were then added, and the mixture was stirred at RT for a further 12 h. The reaction mixture was then filtered through kieselguhr, the filter residue was washed with dichloromethane and methanol and the filtrate was concentrated to dryness. The residue was purified by preparative HPLC (Gromsil C18 column, 10 μm; mobile phase: acetonitrile/water+0.1% TFA 10:90→90:10). The product was obtained as a colorless amorphous solid (404.6 mg, 46% of theory).

LC-MS (Method 2): $R_t$=2.36 min; MS (ESIpos): m/z (%)=455.1 (100) [M+H]$^+$; MS (ESIneg): m/z (%)=453.2 (100) [M−H]$^−$.

$^1$H-NMR (400 MHz, DMSO-$d_6$): δ=1.00 (t, 3H), 2.20 (s, 3H), 4.00 (q, 2H), 6.90 (s, 1H), 7.80-8.00 (m, 7H), 8.20 (br. s, 1H).

Example 71

Ethyl (7R)-7-(4-cyanophenyl)-5-methyl-4-[3-(trifluoromethyl)phenyl]-4,7-dihydrotetrazolo[1,5-a]-pyrimidine-6-carboxylate

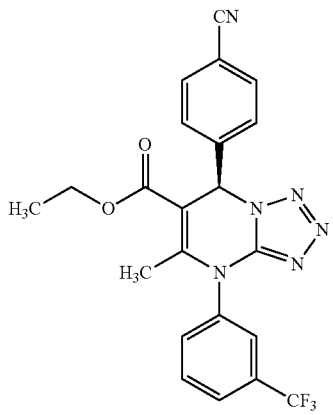 [SMILES: CCOC(=O)C1=C(C)N(c2cccc(C(F)(F)F)c2)c2nnnn2[C@@H]1c1ccc(C#N)cc1]

Ethyl (rac)-7-(4-cyanophenyl)-5-methyl-4-[3-(trifluoromethyl)phenyl]-4,7-dihydrotetrazolo[1,5-a]-pyrimidine-6-carboxylate (443 mg, 0.98 mmol) was separated into the enantiomers by preparative HPLC chromatography on a chiral phase [stationary phase: Daicel Chiralpak IB 5 μm; column dimension: 250×20 mm; sample preparation: solution in 320 ml methanol/MTBE (3:13); injection volume: 0.9 ml; mobile phase: MTBE/methanol 9:1; flow: 15 ml/min; temperature: 30° C.; detection: 220 nm]. This gave 215 mg (97% d. Th., >99.5% ee) of the 7R enantiomer as a colorless amorphous solid.

HPLC [stationary phase: Daicel Chiralpak IB 5 μm; column dimension: 250×4.6 mm; mobile phase: MTBE/methanol 9:1; flow: 1 ml/min; temperature: 25° C.; detection: 220 nm]: $R_t$=4.13 min. (7S enantiomer: $R_t$=3.59 min)

The absolute configuration of the title compound was confirmed by single-crystal X-ray structural analysis.

For further analytical data see the racemic compound (Example 70).

Example 72

(7R)-7-(4-Cyanophenyl)-5-methyl-4-[3-(trifluoromethyl)phenyl]-4,7-dihydrotetrazolo[1,5-a]-pyrimidine-6-carboxylic acid

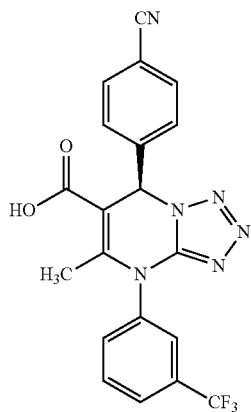 [SMILES: CC1=C(C(=O)O)[C@@H](c2ccc(C#N)cc2)n2nnnc2N1c1cccc(C(F)(F)F)c1]

The reaction was carried out under argon. Solid lithium hydroxide (15.8 mg, 660 μmol, 3 eq.) was added to a solution of ethyl (7R)-7-(4-cyanophenyl)-5-methyl-4-[3-(trifluoromethyl)phenyl]-4,7-dihydrotetrazolo[1,5-a]pyrimidine-6-carboxylate (100 mg, 220 μmol) in an ethanol/THF/water mixture (4:1:0.6, 5.6 ml). The solution was heated at 55° C. for 1.5 h. At 0° C., the mixture was then acidified with 1 N hydrochloric acid (0.66 ml) and then directly purified by preparative HPLC (Kromasil C18 column; mobile phase: acetonitrile/water+0.1% TFA 10:90→90:10). The product was obtained as a colorless amorphous solid (67 mg, 71% of theory).

LC-MS (Method 2): $R_t$=2.36 min; MS (ESIpos): m/z (%)=427.1 (100) [M+H]$^+$; MS (ESIneg): m/z (%)=425.0 (80) [M−H]$^−$.

$^1$H-NMR (400 MHz, DMSO-$d_6$): δ=2.20 (s, 3H), 6.85 (s, 1H), 7.75-8.00 (m, 7H), 8.20 (br. s, 1H), 12.85 (br. s, 1H).

Example 73

(7R)-7-(4-Cyanophenyl)-5-methyl-4-[3-(trifluoromethyl)phenyl]-4,7-dihydrotetrazolo[1,5-a]-pyrimidine-6-carboxamide

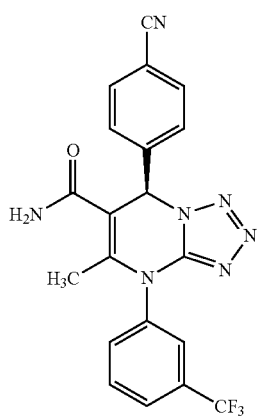 [SMILES: CC1=C(C(N)=O)[C@@H](c2ccc(C#N)cc2)n2nnnc2N1c1cccc(C(F)(F)F)c1]

The reaction was carried out under argon. (7R)-7-(4-Cyanophenyl)-5-methyl-4-[3-(trifluoromethyl)phenyl]-4,7-dihydrotetrazolo[1,5-a]pyrimidine-6-carboxylic acid (62 mg, 145 μmol) and ammonium chloride (116.7 mg, 2.2 mmol, 15 eq.) were initially charged in dry DMF (3.5 ml) at 0° C., and HATU (415 mg, 1.8 mmol, 7.5 eq.) and triethylamine (147 mg, 1.45 mmol, 10 eq.) were added. The mixture was stirred for 12 h, during which time it gradually warmed to RT. The reaction mixture was then concentrated, and the residue was taken up in acetonitrile (with 0.1% TFA) and then purified by preparative HPLC (Gromsil C18 column, 10 μm; mobile phase: acetonitrile/water+0.1% TFA 10:90→90:10). The product was obtained as a colorless amorphous solid (36 mg, 58% of theory).

LC-MS (Method 4): $R_t$=2.86 min; MS (ESIpos): m/z (%)=426.1 (100) [M+H]$^+$; MS (ESIneg): m/z (%)=424.2 (60) [M−H]$^-$.

$^1$H-NMR (400 MHz, DMSO-d$_6$): δ=1.90 (s, 3H), 6.90 (s, 1H), 7.30 (br. s, 1H), 7.55 (br. s, 1H), 7.70-7.95 (m, 7H), 8.10 (br. s, 1H).

Example 74

(rac)-7-(4-Cyanophenyl)-5-methyl-4-[3-(trifluoromethyl)phenyl]-4,7-dihydrotetrazolo[1,5-a]pyrimidine-6-carbonitrile

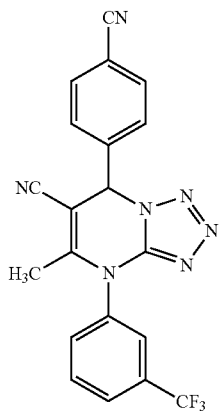 [SMILES: CC1=C(C#N)C(c2ccc(C#N)cc2)n2nnnc2N1c1cccc(C(F)(F)F)c1]

The reaction was carried out under argon. (rac)-7-(4-Cyanophenyl)-5-methyl-4-[3-(trifluoromethyl)phenyl]-4,7-dihydrotetrazolo[1,5-a]pyrimidine-6-carboxamide (10 mg, 24 μmol; prepared analogously to Example 72/73 from Example 70) was initially charged in dry THF (0.6 ml), methoxycarbonylsulfamoyltriethylammonium hydroxide (Burgess reagent; 22 mg, 94 μmol, 4 eq.) was added and the mixture was stirred at RT for 1 h. HPLC showed complete conversion. The reaction mixture was then concentrated and the residue was purified by preparative HPLC (Gromsil C18 column, 10 μm; mobile phase: acetonitrile/water+0.1% TFA 10:90→90:10). The title compound was obtained as a solid (8.3 mg, 87% of theory).

LC-MS (Method 2): $R_t$=2.57 min; MS (ESIpos): m/z (%)=408.1 (100) [M+H]$^+$; MS (ESIneg): m/z (%)=406.1 (100) [M−H]$^-$.

HR-MS (Method 10): $C_{20}H_{13}N_7F_3$ [M+H]$^+$ found 408.1183. calc. 408.1179.

$^1$H-NMR (400 MHz, DMSO-d$_6$): δ=2.05 (s, 3H), 6.90 (s, 1H), 7.85 (br. m, 3H), 8.00 (br. s, 4H), 8.25 (br. s, 1H).

Example 75

(7R)-7-(4-Cyanophenyl)-5-methyl-4-[3-(trifluoromethyl)phenyl]-4,7-dihydrotetrazolo[1,5-a]-pyrimidine-6-carbonitrile

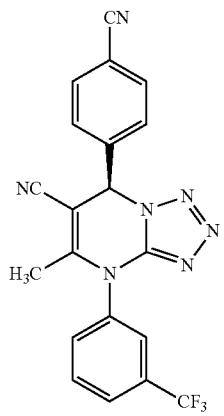 [SMILES: CC1=C(C#N)[C@@H](c2ccc(C#N)cc2)n2nnnc2N1c1cccc(C(F)(F)F)c1]

The reaction was carried out under argon. (7R)-7-(4-Cyanophenyl)-5-methyl-4-[3-(trifluoromethyl)phenyl]-4,7-dihydrotetrazolo[1,5-a]pyrimidine-6-carboxamide (34 mg, 80 μmol) was initially charged in dry THF (1.9 ml), methoxycarbonylsulfamoyltriethylammonium hydroxide (Burgess reagent; 76 mg, 320 μmol, 4 eq.) was added and the mixture was stirred at RT for 1 h. HPLC showed complete conversion. The reaction mixture was then concentrated and the residue was purified by preparative HPLC (Gromsil C18 column, 10 μm; mobile phase: acetonitrile/water+0.1% TFA 10:90→90:10). The title compound was obtained as a solid (29 mg, 89% of theory).

LC-MS (Method 3): $R_t$=3.62 min; MS (ESIpos): m/z (%)=408.3 (30) [M+H]$^+$; MS (ESIneg): m/z (%)=406.2 (100) [M−H]$^-$.

Example 76

4-(6-(2-Methoxyethyl)-7-oxo-4-[3-(trifluoromethyl)phenyl]-5,6,7,8-tetrahydro-4H-pyrrolo[3,4-d]-tetrazolo[1,5-a]pyrimidin-8-yl)benzonitrile

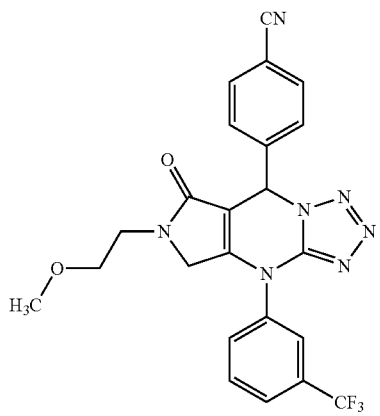 [SMILES: COCCN1CC2=C(C1=O)C(c1ccc(C#N)cc1)n1nnnc1N2c1cccc(C(F)(F)F)c1]

Ethyl 5-(bromomethyl)-7-(4-cyanophenyl)-4-[3-(trifluoromethyl)phenyl]-4,7-dihydrotetrazolo-[1,5-a]pyrimidine-6-carboxylate (35.3 mg, 66.1 µmol) was initially charged in acetone (1.0 ml). 2-Methoxyethylamine (12.4 mg, 4 µl, 165 µmol, 2.5 eq.) was added dropwise, and the mixture was then stirred at RT overnight. After addition of more 2-methoxyethylamine (9.9 mg, 132 µmol, 2 eq.), the mixture was stirred at RT for a further 5 h. The reaction mixture was then concentrated under reduced pressure and the residue was purified by preparative HPLC (Kromasil C18 column, 30×250 mm; mobile phase: acetonitrile-water-0.1% TFA). After lyophilization, the product was obtained as a solid (13 mg, 41% of theory).

LC-MS (Method 4): $R_f$=3.13 min; MS (ESIpos): m/z (%)=482.1 (100) [M+H]$^+$; MS (ESIneg): m/z (%)=480.2 (100) [M−H]$^-$.

$^1$H-NMR (400 MHz, DMSO-d$_6$): δ=3.15 (s, 3H), 3.30-3.50 (m, 4H), 4.15 (dd, 2H), 6.90 (s, 1H), 7.75-8.15 (m, 7H), 8.30 (br. s, 1H).

Example 77

Ethyl (rac)-6-(4-cyanophenyl)-8-methyl-9-[3-(trifluoromethyl)phenyl]-6,9-dihydropyrimido[2,1-f]-purine-7-carboxylate

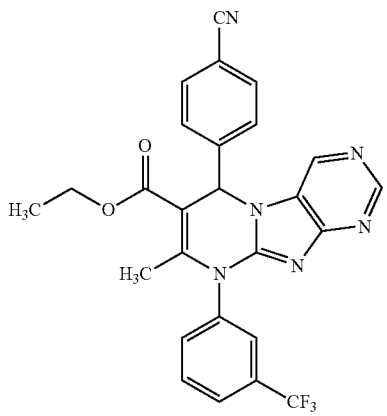 [SMILES: CCOC(=O)C1=C(C)N(c2cccc(C(F)(F)F)c2)c2nc3ncncc3n2C1c1ccc(C#N)cc1]

(rac)-Ethyl 6-(4-cyanophenyl)-8-methyl-6,9-dihydropyrimido[2,1-f]purine-7-carboxylate (30 mg, 0.08 mmol), 3-(trifluoromethyl)phenylboronic acid (31 mg, 0.17 mmol, 2 eq.), anhydrous copper(II) acetate (30 mg, 0.17 mmol, 2 eq.) and molecular sieve (100 mg, 4 Å) were initially charged. Under an atmosphere of argon, abs. dichloromethane (5 ml), pyridine (27 µl, 0.33 mmol, 4 eq.) and triethylamine (23 µl, 0.17 mmol, 2 eq.) were added. After 12 h of stirring, the mixture was filtered over kieselguhr and the filtrate was concentrated under reduced pressure. The residue was purified by preparative HPLC (Gromsil C18 column, 30×250 mm; mobile phase: acetonitrile-water-0.1% TFA). After lyophilization, the product was obtained as a solid (5.6 mg, 13% of theory).

LC-MS (Method 2): $R_f$=2.41 min; MS (ESIpos): m/z (%)=505.2 (100) [M+H]$^+$; MS (ESIneg): m/z (%)=503.2 (100) [M−H]$^-$.

$^1$H-NMR (400 MHz, DMSO-d$_6$): δ=1.1 (t, 3H), 2.2 (s, 3H), 4.05 (m, 2H), 6.9 (s, 1H), 7.85-8.3 (br. m, 8H), 8.7 (br. m, 2H).

Example 78

Ethyl (rac)-9-(4-cyanophenyl)-7-methyl-6-[3-(trifluoromethyl)phenyl]-6,9-dihydropyrimido[1,2-e]-purin-8-carboxylate

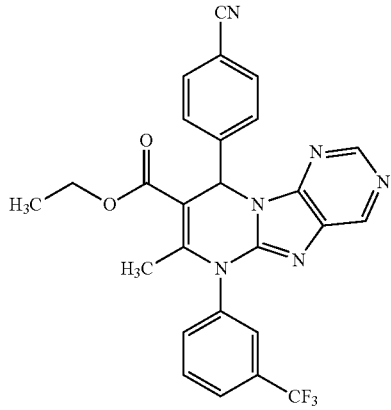 [SMILES: CCOC(=O)C1=C(C)N(c2cccc(C(F)(F)F)c2)c2nc3cncnc3n2C1c1ccc(C#N)cc1]

(rac)-Ethyl 9-(4-cyanophenyl)-7-methyl-6,9-dihydropyrimido[1,2-e]purine-8-carboxylate (20 mg, 55 µmol), 3-(trifluoromethyl)phenylboronic acid (21 mg, 0.11 mmol, 2 eq.), anhydrous copper(II) acetate (20 mg, 0.11 mmol, 2 eq.) and molecular sieve (50 mg, 4 Å) were initially charged. Under an atmosphere of argon, abs. dichloromethane (2 ml), pyridine (18 µl, 0.22 mmol, 4 eq.) and triethylamine (15 µl, 0.11 mmol, 2 eq.) were added. After 12 h of stirring, the mixture was filtered through kieselguhr and the filtrate was concentrated under reduced pressure. The residue was purified by preparative HPLC (Gromsil C18 column, 30×250 mm; mobile phase: acetonitrile-water-0.1% TFA). After lyophilization, the product was obtained as a solid (5.6 mg, 19% of theory).

LC-MS (Method 2): $R_f$=2.64 min; MS (ESIpos): m/z (%)=505.1 (100) [M+H]$^+$; MS (ESIneg): m/z (%)=503.1 (100) [M−H]$^-$.

$^1$H-NMR (400 MHz, DMSO-d$_6$): δ=1.15 (t, 3H), 2.25 (s, 3H), 4.05 (m, 2H), 6.7 (s, 1H), 7.85-8.3 (br. m, 8H), 8.7-8.75 (br. m, 2H).

Example 79

(rac)-Ethyl 7-(4-cyanophenyl)-5-methyl-4-[3-(trifluoromethyl)phenyl]-2-{[3-(trifluoromethyl)-phenyl]amino}-4,7-dihydro[1,2,4]triazolo[1,5-a]pyrimidine-6-carboxylate

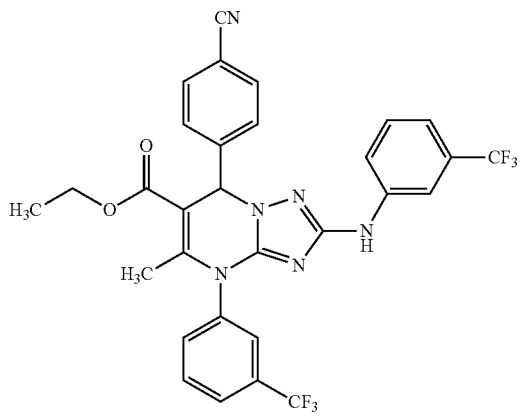 [SMILES: CCOC(=O)C1=C(C)N(c2cccc(C(F)(F)F)c2)c2nc(Nc3cccc(C(F)(F)F)c3)nn2C1c1ccc(C#N)cc1]

(rac)-Ethyl 2-amino-7-(4-cyanophenyl)-5-methyl-4,7-dihydro[1,2,4]triazolo[1,5-a]pyrimidine-6-carboxylate (20 mg, 61 µmol), 3-(trifluoromethyl)phenylboronic acid (23 mg, 0.123 mmol, 2 eq.), anhydrous copper(II) acetate (22 mg, 0.123 mmol, 2 eq.) and molecular sieve (80 mg, 4 Å) were initially charged. Under an atmosphere of argon, abs. dichloromethane (2 ml), pyridine (10 µl, 0.123 mmol, 2 eq.) and triethylamine (17 µl, 0.123 mmol, 2 eq.) were added. After 12 h of stirring, the mixture was filtered through kieselguhr and the filtrate was concentrated under reduced pressure. The residue was purified by preparative HPLC (Gromsil C18 column, 30×250 mm; mobile phase: acetonitrile-water-0.1% TFA). After lyophilization, the product was obtained as a solid (8.5 mg, 8% of theory).

LC-MS (Method 1): $R_t$=3.03 min; MS (ESIpos): m/z (%)=613.3 (100) [M+H]$^+$; MS (ESIneg): m/z (%)=611.3 (100) [M–H]$^-$.

$^1$H-NMR (400 MHz, DMSO-d$_6$): δ=1.0 (t, 3H), 2.2 (s, 3H), 4.0 (q, 2H), 6.45 (s, 1H), 7.05 (m, 1H), 7.35 (m, 1H), 7.45 (m, 1H), 7.75-8.0 (br. m, 8H), 8.2 (br. m, 1H), 9.65 (s, 1H).

Example 80

(rac)-Diethyl 7-(4-cyanophenyl)-5-methyl-4-[3-(trifluoromethyl)phenyl]-4,7-dihydro[1,2,4]triazolo[1,5-a]pyrimidine-2,6-dicarboxylate

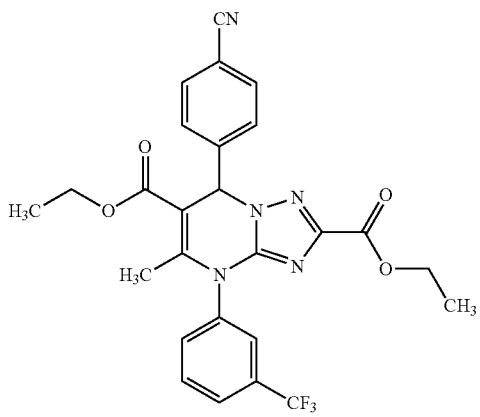 [SMILES: CCOC(=O)C1=C(C)N(c2cccc(C(F)(F)F)c2)c2nc(C(=O)OCC)nn2C1c1ccc(C#N)cc1]

(rac)-Diethyl 7-(4-cyanophenyl)-5-methyl-4,7-dihydro[1,2,4]triazolo[1,5-a]pyrimidine-2,6-dicarboxylate (200 mg, 0.52 mmol), 3-(trifluoromethyl)phenylboronic acid (199 mg, 1.05 mmol, 2 eq.), anhydrous copper(II) acetate (190 mg, 1.05 mmol, 2 eq.) and molecular sieve (500 mg, 4 Å) were initially charged. Under an atmosphere of argon protective gas, abs. dichloromethane (5 ml), pyridine (170 µl, 2.10 mmol, 4 eq.) and triethylamine (146 µl, 1.05 mmol, 2 eq.) were added. After 24 h of stirring, the mixture was filtered through kieselguhr, the filter residue was washed with dichloromethane and the filtrate was concentrated under reduced pressure. The residue was purified by preparative HPLC (Gromsil C18 column, 30×250 mm; mobile phase: acetonitrile-water-0.1% TFA). After lyophilization, the product was obtained as a solid (32.7 mg, 12% of theory).

LC-MS (Method 4): $R_t$=3.83 min; MS (ESIpos): m/z (%)=526.2 (100) [M+H]$^+$; MS (ESIneg): m/z (%)=524.3 (100) [M–H]$^-$.

$^1$H-NMR (400 MHz, DMSO-d$_6$): δ=1.0 (t, 3H), 1.2 (t, 3H), 2.15 (s, 3H), 4.0 (q, 2H), 4.2 (m, 2H), 6.6 (s, 1H), 7.75-7.95 (m, 7H), 8.15 (br. s, 1H).

Example 81

(rac)-Ethyl 7-(4-cyanophenyl)-2,5-dimethyl-4-[3-(trifluoromethyl)phenyl]-4,7-dihydro[1,2,4]triazolo[1,5-a]pyrimidine-6-carboxylate

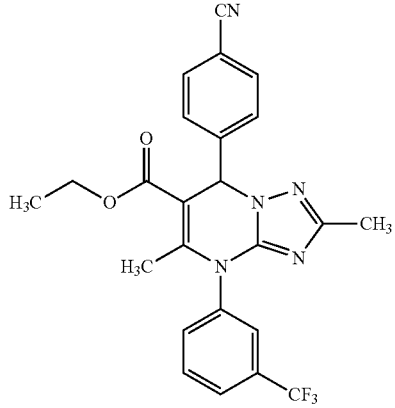 [SMILES: CCOC(=O)C1=C(C)N(c2cccc(C(F)(F)F)c2)c2nc(C)nn2C1c1ccc(C#N)cc1]

(rac)-Ethyl 7-(4-cyanophenyl)-2,5-dimethyl-4,7-dihydro[1,2,4]triazolo[1,5-a]pyrimidine-6-carboxylate (50 mg, 0.15 mmol), 3-(trifluoromethyl)phenylboronic acid (88 mg, 0.46 mmol, 3 eq.), anhydrous copper(II) acetate (140 mg, 0.77 mmol, 5 eq.) and molecular sieve (80 mg, 4 Å) were initially charged. Under an atmosphere of argon protective gas, abs. dichloromethane (4 ml), pyridine (125 µl, 1.55 mmol, 10 eq.) and triethylamine (108 µl, 0.77 mmol, 5 eq.) were added. After 24 h of stirring, the mixture was filtered through kieselguhr and the filtrate was concentrated under reduced pressure. The residue was purified by preparative HPLC (Gromsil C18 column, 30×250 mm; mobile phase: acetonitrile-water-0.05% TFA). After lyophilization, the product was obtained as a solid (4.5 mg, 6% of theory).

LC-MS (Method 1): $R_t$=2.47 min; MS (ESIpos): m/z (%)=468.3 (100) [M+H]$^+$; MS (ESIneg): m/z (%)=466.2 (100) [M–H]$^-$.

$^1$H-NMR (400 MHz, DMSO-d$_6$): δ=1.0 (t, 3H), 2.0 (s, 3H), 2.2 (s, 3H), 4.0 (q, 2H), 6.4 (s, 1H), 7.65 (m, 2H), 7.8-7.9 (m, 5H), 8.1 (br. s, 1H).

Example 82

(rac)-Ethyl 7-(4-cyanophenyl)-2-methoxy-5-methyl-4-[3-(trifluoromethyl)phenyl]-4,7-dihydro-[1,2,4]triazolo[1,5-a]pyrimidine-6-carboxylate

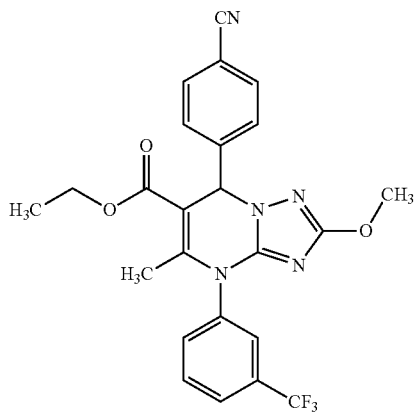 [SMILES: CCOC(=O)C1=C(C)N(c2cccc(C(F)(F)F)c2)c2nc(OC)nn2C1c1ccc(C#N)cc1]

(rac)-Ethyl 7-(4-cyanophenyl)-2-methoxy-5-methyl-4,7-dihydro[1,2,4]triazolo[1,5-a]pyrimidine-6-carboxylate (185 mg, 0.55 mmol), 3-(trifluoromethyl)phenylboronic acid (207 mg, 1.09 mmol, 2 eq.), anhydrous copper(II) acetate (198 mg, 1.09 mmol, 2 eq.) and molecular sieve (80 mg, 4 Å) were initially charged. Under an atmosphere of argon protective gas, abs. dichloromethane (12 ml), pyridine (176 µl, 2.18 mmol, 4 eq.) and triethylamine (152 µl, 1.09 mmol, 2 eq.) were added. After 24 h of stirring, the mixture was filtered through kieselguhr and the filtrate was concentrated under reduced pressure. The residue was purified by preparative HPLC (Gromsil C18 column, 30×250 mm; mobile phase: acetonitrile-water-0.05% TFA). After lyophilization, the product was obtained as a solid (103 mg, 39% of theory).

LC-MS (Method 1): $R_t$=2.57 min; MS (ESIpos): m/z (%)=484.3 (100) [M+H]$^+$; MS (ESIneg): m/z (%)=482.3 (100) [M−H]$^−$.

$^1$H-NMR (400 MHz, DMSO-d$_6$): δ=1.05 (t, 3H), 2.15 (s, 3H), 3.65 (s, 3H), 4.0 (q, 2H), 6.35 (s, 1H), 7.65 (m, 2H), 7.8-7.9 (m, 5H), 8.1 (br. s, 1H).

Example 83

(rac)-Ethyl 7-(4-cyanophenyl)-5-methyl-4-[3-(trifluoromethyl)phenyl]-4,7-dihydro[1,2,4]triazolo-[1,5-a]pyrimidine-6-carboxylate

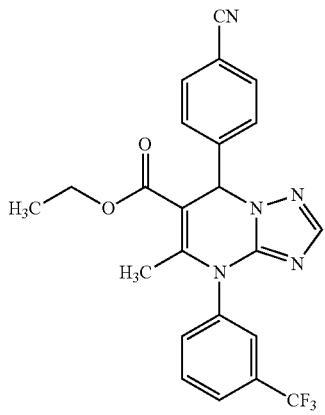 [SMILES: CCOC(=O)C1=C(C)N(c2cccc(C(F)(F)F)c2)c2ncnn2C1c1ccc(C#N)cc1]

(rac)-Ethyl 7-(4-cyanophenyl)-5-methyl-4,7-dihydro[1,2,4]triazolo[1,5-a]pyrimidine-6-carboxylate (20 mg, 64 µmol), 3-(trifluoromethyl)phenylboronic acid (25 mg, 0.13 mmol, 2 eq.), anhydrous copper(II) acetate (23 mg, 0.13 mmol, 2 eq.) and molecular sieve (100 mg, 4 Å) were initially charged. Under an atmosphere of argon protective gas, abs. dichloromethane (2 ml), pyridine (10 µl, 0.13 mmol, 2 eq.) and triethylamine (18 µl, 0.13 mmol, 2 eq.) were added. After 24 h of stirring, the mixture was filtered through kieselguhr and the filtrate was concentrated under reduced pressure. The residue was purified by preparative HPLC (Gromsil C18 column, 30×250 mm; mobile phase: acetonitrile-water-0.05% TFA). After lyophilization, the product was obtained as a solid (10.5 mg, 36% of theory).

LC-MS (Method 3): $R_t$=3.8 min; MS (ESIpos): m/z (%)=454.2 (100) [M+H]$^+$; MS (ESIneg): m/z (%)=452.2 (100) [M−H]$^−$.

$^1$H-NMR (400 MHz, DMSO-d$_6$): δ=1.05 (t, 3H), 2.2 (s, 3H), 4.0 (q, 2H), 6.55 (s, 1H), 7.6 (s, 1H), 7.7 (m, 2H), 7.8-7.9 (m, 5H), 8.1 (br. s, 1H).

Example 84

(7R)-6-Cyano-7-(4-cyanophenyl)-N,5-dimethyl-4-[3-(trifluoromethyl)phenyl]-4,7-dihydro[1,2,4]-triazolo[1,5-a]pyrimidine-2-sulfonamide

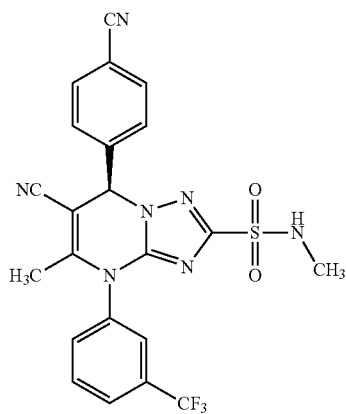

Under an atmosphere of argon, abs. THF (3 ml) was stirred with molecular sieve (4 Å, 30 mg) for 30 min. (7R)-6-Cyano-7-(4-cyanophenyl)-5-methyl-4-[3-(trifluoromethyl)phenyl]-4,7-dihydro-[1,2,4]triazolo[1,5-a]pyrimidine-2-sulfonyl chloride (63%, 50 mg, 62 µmol), methylamine (2 M solution in THF; 94 µl, 0.19 mmol, 3 eq.) and triethylamine (9 µl, 62 µmol, 1 eq.) were added and the mixture was stirred at RT for 12 h. The reaction solution was then concentrated under reduced pressure and the residue was purified by preparative HPLC (Reprosil C18 column, 30×250 mm; mobile phase: acetonitrile-water-0.1% TFA). After lyophilization, the product was obtained as a solid (23 mg, 73% of theory).

LC-MS (Method 9): $R_t$=1.07 min; MS (ESIpos): m/z (%)=500.3 (100) [M+H]$^+$; MS (ESIneg): m/z (%)=498.3 (100) [M−H]$^−$.

$^1$H-NMR (400 MHz, DMSO-d$_6$): δ=2.0 (s, 3H), 2.45 (d, 3H), 6.65 (s, 1H), 7.85 (m, 3H), 7.9-8.05 (m, 5H), 8.2 (br. s, 1H).

Example 85

(7R)-6-Cyano-7-(4-cyanophenyl)-5-methyl-4-[3-(trifluoromethyl)phenyl]-4,7-dihydro[1,2,4]triazolo[1,5-a]pyrimidine-2-sulfonamide

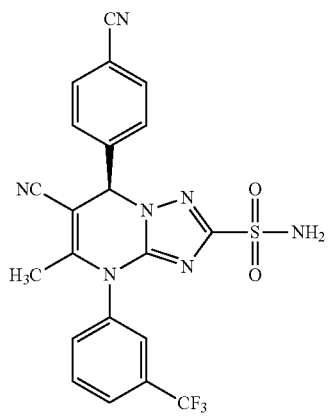 [SMILES: CC1=C(C#N)[C@@H](c2ccc(C#N)cc2)n2nc(S(N)(=O)=O)nc2N1c1cccc(C(F)(F)F)c1]

Under an atmosphere of argon, abs. dioxane (5 ml) was stirred with molecular sieve (4 Å, 30 mg) for 30 min. (7R)-6-Cyano-7-(4-cyanophenyl)-5-methyl-4-[3-(trifluoromethyl)phenyl]-4,7-dihydro-[1,2,4]triazolo[1,5-a]pyrimidine-2-sulfonyl chloride (63%, 60 mg, 75 μmol) was added and the solution was cooled to 7° C. Dry ammonia gas was then introduced for 15 min, and the mixture was then cooled to 0° C. Triethylamine (11 μl, 75 μmol, 1 eq.) was added, and the reaction was then stirred for 12 h, during which time the mixture gradually warmed to RT. The solvent was then distilled off under reduced pressure, and the residue was purified by preparative HPLC (Reprosil C18 column, 30×250 mm; mobile phase: acetonitrile-water-0.1% TFA). After lyophilization, the product was obtained as a solid (33 mg, 90% of theory).

LC-MS (Method 9): $R_t$=1.02 min; MS (ESIpos): m/z (%)=486.3 (100) [M+H]$^+$; MS (ESIneg): m/z (%)=484.3 (100) [M−H]$^−$.

$^1$H-NMR (400 MHz, DMSO-d$_6$): δ=2.0 (s, 3H), 6.6 (s, 1H), 7.75 (s, 2H), 7.85 (m, 3H), 7.9-8.05 (m, 4H), 8.25 (br. s, 1H).

Example 86

(7R)-6-Cyano-7-(4-cyanophenyl)-N-ethyl-5-methyl-4-[3-(trifluoromethyl)phenyl]-4,7-dihydro-[1,2,4]triazolo[1,5-a]pyrimidine-2-sulfonamide

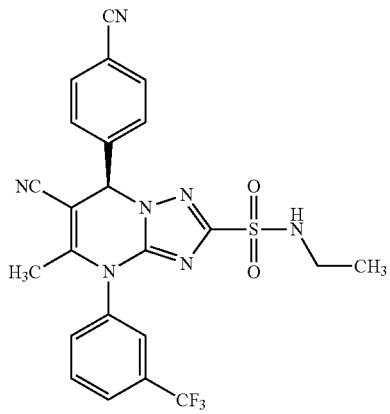 [SMILES: CCNS(=O)(=O)c1nc2n(n1)[C@H](c1ccc(C#N)cc1)C(C#N)=C(C)N2c1cccc(C(F)(F)F)c1]

Under an atmosphere of argon, abs. THF (3 ml) was stirred with molecular sieve (4 Å, 30 mg) for 30 min. (7R)-6-Cyano-7-(4-cyanophenyl)-5-methyl-4-[3-(trifluoromethyl)phenyl]-4,7-dihydro-[1,2,4]triazolo[1,5-a]pyrimidine-2-sulfonyl chloride (63%, 50 mg, 62 μmol), ethylamine (2 M solution in THF; 94 μl, 0.19 mmol, 3 eq.) and triethylamine (9 μl, 62 μmol, 1 eq.) were added, and the mixture was stirred at RT for 12 h. The reaction solution was then concentrated under reduced pressure, and the residue was purified by preparative HPLC (Reprosil C18 column, 30×250 mm; mobile phase: acetonitrile-water-0.1% TFA). After lyophilization, the product was obtained as a solid (29.9 mg, 93% of theory).

LC-MS (Method 9): $R_t$=1.24 min; MS (ESIpos): m/z (%)=514.0 (100) [M+H]$^+$; MS (ESIneg): m/z (%)=512.9 (100) [M−H]$^−$.

$^1$H-NMR (400 MHz, DMSO-d$_6$): δ=0.9 (t, 3H), 2.0 (s, 3H), 2.8 (m, 2H), 6.65 (s, 1H), 7.85 (m, 3H), 7.9-8.0 (m, 4H), 8.05 (t, 1H), 8.2 (br. s, 1H).

Example 87

(7R)-6-Cyano-7-(4-cyanophenyl)-N-cyclopropyl-5-methyl-4-[3-(trifluoromethyl)phenyl]-4,7-dihydro[1,2,4]triazolo[1,5-a]pyrimidine-2-sulfonamide

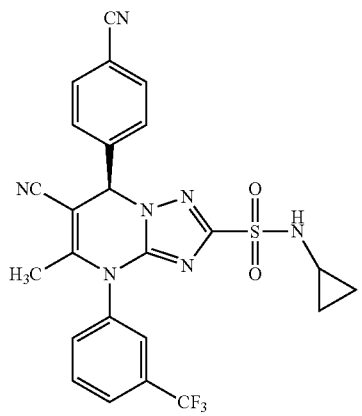 [SMILES: CC1=C(C#N)[C@@H](c2ccc(C#N)cc2)n2nc(S(=O)(=O)NC3CC3)nc2N1c1cccc(C(F)(F)F)c1]

Under an atmosphere of argon, abs. THF (3 ml) was stirred with molecular sieve (4 Å, 30 mg) for 30 min. (7R)-6-Cyano-7-(4-cyanophenyl)-5-methyl-4-[3-(trifluoromethyl)phenyl]-4,7-dihydro-[1,2,4]triazolo[1,5-a]pyrimidine-2-sulfonyl chloride (63%, 50 mg, 62 μmol), cyclopropylamine (13 μl, 0.19 mmol, 3 eq.) and triethylamine (9 μl, 63 μmol, 1 eq.) were added, and the mixture was stirred at RT for 12 h. The reaction solution was then concentrated under reduced pressure and the residue was purified by preparative HPLC (Reprosil C18 column, 30×250 mm; mobile phase: acetonitrile-water-0.1% TFA). After lyophilization, the product was obtained as a solid (27 mg, 82% of theory).

LC-MS (Method 9): $R_t$=1.11 min; MS (ESIpos): m/z (%)=526.3 (100) [M+H]$^+$; MS (ESIneg): m/z (%)=524.3 (100) [M−H]$^−$.

$^1$H-NMR (400 MHz, DMSO-d$_6$): δ=0.3-0.45 (m, 4H), 2.0 (s, 3H), 2.25 (m, 1H), 6.65 (s, 1H), 7.85 (m, 3H), 7.9-8.0 (m, 4H), 8.25 (br. s, 1H), 8.4 (d, 1H).

Example 88

(7R)-7-(4-Cyanophenyl)-5-methyl-4-[3-(trifluoromethyl)phenyl]-4,7-dihydro[1,2,4]triazolo[1,5-a]-pyrimidine-6-carbonitrile

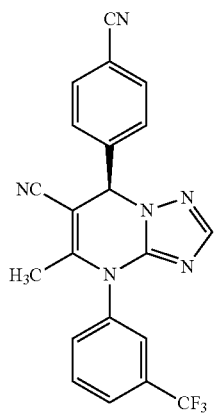 [SMILES: CC1=C(C#N)[C@@H](c2ccc(C#N)cc2)n2ncnc2N1c1cccc(C(F)(F)F)c1]

The title compound was obtained as a byproduct in the preparation of (7R)-6-cyano-7-(4-cyanophenyl)-5-methyl-4-[3-(trifluoromethyl)phenyl]-4,7-dihydro[1,2,4]triazolo[1,5-a]pyrimidine-2-sulfonyl chloride (Example 29A). The product was isolated by preparative HPLC (Kromasil 5μ column, 50×20 mm; mobile phase: acetonitrile-water-0.1% TFA) and, after lyophilization of the appropriate fractions, obtained as a solid (3 mg, 4% of theory).

LC-MS (Method 9): R$_t$=1.11 min; MS (ESIpos): m/z (%)=407.3 (100) [M+H]$^+$; MS (ESIneg): m/z (%)=405.3 (100) [M−H]$^−$.

$^1$H-NMR (400 MHz, DMSO-d$_6$): δ=2.0 (s, 3H), 6.55 (s, 1H), 7.70 (s, 1H), 7.75 (m, 2H), 7.85 (m, 1H), 7.95 (m, 4H), 8.15 (br. s, 1H).

Example 89

(rac)-Ethyl 5-(4-cyanophenyl)-7-methyl-8-[3-(trifluoromethyl)phenyl]-5,8-dihydroimidazo[1,2-a]-pyrimidine-6-carboxylate

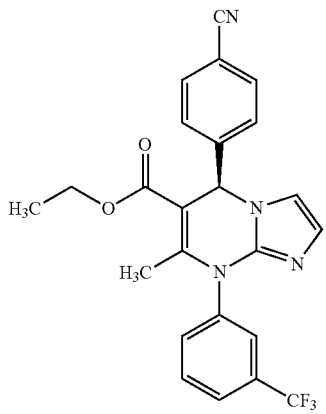 [SMILES: CCOC(=O)C1=C(C)N(c2cccc(C(F)(F)F)c2)c2nccn2[C@@H]1c1ccc(C#N)cc1]

(rac)-Ethyl 5-(4-cyanophenyl)-7-methyl-5,8-dihydroimidazo[1,2-a]pyrimidine-6-carboxylate (152 mg, 0.49 mmol), 3-(trifluoromethyl)phenylboronic acid (187 mg, 0.1 mmol, 2 eq.), anhydrous copper(II) acetate (181 mg, 0.1 mmol, 2 eq.) and molecular sieve (200 mg, 4 Å) were initially charged. Under an atmosphere of argon protective gas, abs. dichloromethane (5 ml), pyridine (80 μl, 0.1 mmol, 2 eq.) and triethylamine (137 μl, 0.1 mmol, 2 eq.) were added. After 12 h of stirring, more anhydrous copper(II) acetate (181 mg, 0.1 mmol, 2 eq.) and triethylamine (137 μl, 0.1 mmol, 2 eq.) were added, and the mixture was stirred for a further 48 h. The reaction was then filtered through kieselguhr, and the filtrate was concentrated under reduced pressure. The residue was purified by preparative HPLC (Gromsil C18 column, 30×250 mm; mobile phase: acetonitrile-water-0.05% TFA). After lyophilization, the product was obtained as a solid (26 mg, 12% of theory).

LC-MS (Method 11): R$_t$=2.48 min; MS (ESIpos): m/z (%)=453.1 (100) [M+H]$^+$; MS (ESIneg): m/z (%)=451.2 (100) [M−H]$^−$.

$^1$H-NMR (400 MHz, DMSO-d$_6$): δ=1.05 (t, 3H), 2.2 (s, 3H), 4.0 (q, 2H), 6.5 (s, 1H), 6.75 (br. s, 1H), 6.95 (s, 1H), 7.7 (m, 2H), 7.8-7.95 (m, 5H), 8.1 (s, 1H).

Example 90

Ethyl (5R)-5-(4-cyanophenyl)-7-methyl-8-[3-(trifluoromethyl)phenyl]-5,8-dihydroimidazo[1,2-a]-pyrimidine-6-carboxylate

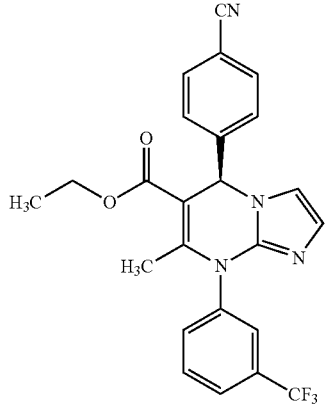

(rac)-Ethyl 5-(4-cyanophenyl)-7-methyl-8-[3-(trifluoromethyl)phenyl]-5,8-dihydroimidazo[1,2-a]-pyrimidine-6-carboxylate (210 mg) was separated into the enantiomers by preparative HPLC chromatography on a chiral phase [stationary phase: Daicel Chiralpak AS-H, 5μ, 250×20 mm; sample preparation: solution in 7 ml of isopropanol; flow: 15 ml/min; detection: 260 nm; injection volume: 1 ml; temperature: 40° C.; mobile phase: isopropanol/isohexane 1:1]. The title compound was obtained as a solid (85 mg, 81% of theory). The enantiomeric excess (ee) was determined chromatographically [column: Daicel Chiralpak AS-H, 5μ, 250×4.6 mm; mobile phase: isopropanol/isohexane 7:3; flow: 1 ml/min; temperature: 30° C.; detection: 215 nm; R$_t$=5.46 min; ee>99.5%].

LC-MS (Method 1): R$_t$=2.33 min; MS (ESIpos): m/z (%)=453.1 (100) [M+H]$^+$; MS (ESIneg): m/z (%)=451.2 (100) [M−H]$^−$.

$^1$H-NMR (500 MHz, CDCl$_3$): δ=1.15 (t, 3H), 2.25 (s, 3H), 4.10 (q, 2H), 6.40 (s, 1H), 6.50 (s, 1H), 6.75 (s, 1H), 7.40 (m, 2H), 7.60-7.80 (m, 6H).

Example 91

(rac)-3-Amino-5-(4-cyanophenyl)-7-methyl-8-[3-(trifluoromethyl)phenyl]-5,8-dihydro[1,2,4]triazolo[4,3-a]pyrimidine-6-carbonitrile hydrochloride

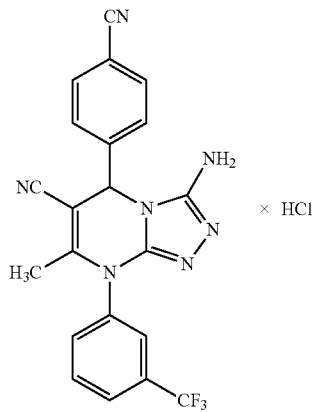 [SMILES: CC1=C(C#N)C(c2ccc(C#N)cc2)n2c(N)nnc2N1c1cccc(C(F)(F)F)c1 ; Cl]

Under an atmosphere of argon, (rac)-4-(4-cyanophenyl)-2-hydrazinyl-6-methyl-1-[3-(trifluoromethyl)phenyl]-1,4-dihydropyrimidine-5-carbonitrile trifluoroacetate (10 mg, 23.1 µmol) was initially charged in abs. methanol (2.5 ml) with molecular sieve (4 Å, 10 mg). Cyanogen bromide (12 µl, 115 µmol, 5 eq.) was added, and the mixture was stirred at RT for 12 h. The reaction solution was then concentrated under reduced pressure and the residue was purified by preparative HPLC (Kromasil C18 column, 20×50 mm; mobile phase: acetonitrile-water-0.1% TFA). After lyophilization, the product was obtained in the form of the free base as a solid (4 mg, 48% of theory). The substance was suspended in 0.5 ml of a 4 N solution of hydrogen chloride in dioxane, and the mixture was once more concentrated to dryness under reduced pressure. This procedure was repeated once more. Finally, water was added to the residue, and the mixture was lyophilized again.

LC-MS (Method 9): $R_t$=0.90 min; MS (ESIpos): m/z (%)=422.3 (100) [M+H]$^+$; MS (ESIneg): m/z (%)=420.3 (100) [M−H]$^-$.

$^1$H-NMR (400 MHz, DMSO-d$_6$): δ=1.95 (s, 3H), 3.5 (m, 2H), 6.15 (s, 1H), 7.65 (m, 2H), 7.85-8.00 (m, 5H), 8.10 (br. s, 1H).

Example 92

N-{6-Cyano-5-(4-cyanophenyl)-7-methyl-8-[3-(trifluoromethyl)phenyl]-5,8-dihydro[1,2,4]triazolo-[4,3-a]pyrimidin-3-yl}cyclopropanecarboxamide

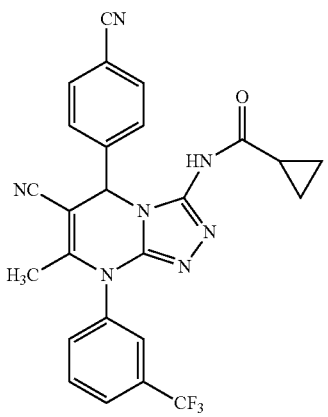 [SMILES: CC1=C(C#N)C(c2ccc(C#N)cc2)n2c(NC(=O)C3CC3)nnc2N1c1cccc(C(F)(F)F)c1]

Under an atmosphere of argon protective gas, 3-amino-5-(4-cyanophenyl)-7-methyl-8-[3-(trifluoromethyl)phenyl]-5,8-dihydro[1,2,4]triazolo[4,3-a]pyrimidine-6-carbonitrile hydrochloride (5 mg, 11 µmol) was dissolved in abs. pyridine (0.5 ml). At room temperature, cyclopropanecarbonyl chloride (2.3 mg, 21.8 µmol, 2 eq.) in abs. THF (50 µl) was added. After 12 h, analysis of the reaction by HPLC showed substantial conversion. The reaction mixture was concentrated under reduced pressure and purified by preparative HPLC (Kromasil C18 column 5 µm, 20×50 mm; mobile phase: acetonitrile-water-0.1% TFA). After lyophilization, the product was obtained as a solid (2.2 mg, 41% of theory).

LC-MS (Method 9): $R_t$=0.98 min; MS (ESIpos): m/z (%)=490.2 (100) [M+H]$^+$; MS (ESIneg): m/z (%)=488.2 (100) [M−H]$^-$.

$^1$H-NMR (400 MHz, DMSO-d$_6$): δ=0.65-1.00 (br. m, 4H), 1.45 (m, 1H), 1.95 (s, 3H), 6.10 (s, 1H), 7.60 (m, 2H), 7.85 (m, 1H), 7.95 (m, 4H), 8.20 (br. s, 1H), 10.50 (br. s, 1H).

B. Assessment of the Pharmacological Activity

The pharmacological effect of the compounds of the invention can be shown in the assays described below:

Abbreviations

AMC 7-amido-4-methylcoumarin
BNP brain natriuretic peptide
BSA bovine serum albumin
HEPES N-(2-hydroxyethyl)piperazine-N'-2-ethanesulphonic acid
HNE humane neutrophil elastase
IC inhibitory concentration
MeOSuc methoxysuccinyl
NADP nicotinamide adenine dinucleotide phosphate
v/v volume to volume ratio (of a solution)
w/v weight to volume ratio (of a solution)

B-1. In Vitro HNE Inhibition Assay

The potency of the compounds of the invention is ascertained in an in vitro inhibition assay. The HNE-mediated amidolytic cleavage of a suitable peptide substrate leads in this connection to an increase in the fluorescent light. The signal intensity of the fluorescent light is directly proportional to the enzyme activity. The effective concentration of a test compound at which half the enzyme is inhibited (50% signal intensity of the fluorescent light) is indicated as IC$_{50}$.

Procedure:

Enzyme (80 pM HNE; from Serva, Heidelberg) and substrate (20 µM MeOSuc-Ala-Ala-Pro-Val-AMC; from Bachem, Weil am Rhein) are incubated in an assay volume of in total 50 µl of assay buffer (0.1 M HEPES pH 7.4, 0.5 M NaCl, 0.1% w/v BSA, 1% v/v DMSO) in a 384-well microtiter plate in the presence and absence of the test substance at 37° C. for 2 hours. The intensity of the fluorescent light from the assay mixtures is measured (Ex. 380 nm, Em. 460 nm). The IC$_{50}$ values are determined by plotting the intensity of the fluorescent light against the active substance concentration.

Representative IC$_{50}$ values for the compounds of the invention (at an HNE concentration of 80 pM) are shown in Table A below:

TABLE A

| Inhibition of human neutrophil elastase (HNE) | |
| --- | --- |
| Exemplary embodiment No. | IC$_{50}$ [nM] |
| 5 | <0.3 |
| 9 | <0.3 |
| 23 | <0.3 |
| 35 | <0.3 |
| 50 | <0.3 |
| 53 | <0.3 |
| 56 | <0.3 |
| 67 | 85.0 |
| 78 | 3.0 |
| 90 | 6.5 |

B-2. Animal Model of Pulmonary Arterial Hypertension

The monocrotaline-induced pulmonary hypertension in rats is a widely used animal model of pulmonary arterial hypertension. The pyrrolizidine alkaloid monocrotaline is metabolized after subcutaneous injection to the toxic monocrotalinepyrrole in the liver and leads within a few days to endothelial damage in the pulmonary circulation, followed by a remodeling of the small pulmonary arteries (media hypertrophy, de novo muscularization). A single subcutaneous injection is sufficient to induce pronounced pulmonary hypertension in rats within 4 weeks [Cowan et al., *Nature Med.* 6, 698-702 (2000)].

Male Sprague-Dawley rats are used for the model. On day 0, the animals receive a subcutaneous injection of 60 mg/kg monocrotaline. Treatment of the animals begins no earlier than 14 days after the monocrotaline injection and extends over a period of at least 14 days. At the end of the study, the animals undergo hemodynamic investigations, and the arterial and central venous oxygen saturation are determined. For the hemodynamic measurement, the rats are initially anesthetized with pentobarbital (60 mg/kg). The animals are then tracheotomized and artificially ventilated (rate: 60 breaths/min; inspiration to expiration ratio: 50:50; positive end-expiratory pressure: 1 cm $H_2O$; tidal volume: 10 ml/kg of body weight; $FIO_2$: 0.5). The anesthesia is maintained by isoflurane inhalation anesthesia. The systemic blood pressure is determined in the left carotid artery using a Millar microtip catheter. A polyethylene catheter is advanced through the right jugular vein into the right ventricle to determine the right ventricular pressure. The cardiac output is determined by thermodilution. Following the hemodynamics, the heart is removed and the ratio of right to left ventricle including septum is determined. In addition, plasma samples are obtained to determine biomarkers (for example proBNP) and plasma substance levels.

B-3. Animal Model of Acute Lung Failure

Elastase-induced lung failure in mice, rats or hamsters is a widely used animal model of acute lung failure (also: "acute lung injury", "acute respiratory distress syndrome") [Tremblay et al., *Chest* 121, 582-588 (2002); Kuraki et al., *Am. J. Resp. Crit. Care Med.* 166, 596-500 (2002)]. The animals are treated 1 hour prior to orotracheal instillation of human neutrophil elastase (HNE). 2 hours after orotracheal HNE instillation, a bronchoalveolar lavage is carried out, and the hemoglobin content and the differential cell picture of the lavage are determined.

B-4. Animal Model of Pulmonary Emphysema

Elastase-induced pulmonary emphysema in mice, rats or hamsters is a widely used animal model of pulmonary emphysema [Sawada et al., *Exp. Lung Res.* 33, 277-288 (2007)]. The animals receive an orotracheal instillation of porcine pancreas elastase. The treatment of the animals starts at the day of the instillation of the porcine pancreas elastase and extends over a period of 3 weeks. At the end of the study, the pulmonary compliance is determined, and an alveolar morphometry is carried out.

C. Exemplary Embodiments of Pharmaceutical Compositions

The compounds of the invention can be converted into pharmaceutical preparations in the following ways:

Tablet:
Composition:
100 mg of the compound of the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm.
Production:
The mixture of compound of the invention, lactose and starch is granulated with a 5% strength solution (m/m) of the PVP in water. The granules are mixed with the magnesium stearate for 5 minutes after drying. This mixture is compressed with a conventional tablet press (see above for format of the tablet). A guideline compressive force for the compression is 15 kN.

Suspension which can be Administered Orally:
Composition:
1000 mg of the compound of the invention, 1000 mg of ethanol (96%), 400 mg of Rhodigel® (xanthan gum from FMC, Pennsylvania, USA) and 99 g of water.

10 ml of oral suspension corresponds to a single dose of 100 mg of the compound of the invention.
Production:
The Rhodigel is suspended in ethanol, and the compound of the invention is added to the suspension. The water is added while stirring. The mixture is stirred for about 6 h until the swelling of the Rhodigel is complete.

Solution which can be Administered Orally:
Composition:
500 mg of the compound of the invention, 2.5 g of polysorbate and 97 g of polyethylene glycol 400.20 g of oral solution corresponds to a single dose of 100 mg of the compound according to the invention.
Production:
The compound of the invention is suspended in the mixture of polyethylene glycol and polysorbate with stirring. The stirring process is continued until the compound according to the invention has completely dissolved.

i.v. Solution:
The compound of the invention is dissolved in a concentration below the saturation solubility in a physiologically tolerated solvent (e.g. isotonic saline solution, 5% glucose solution and/or 30% PEG 400 solution). The solution is sterilized by filtration and used to fill sterile and pyrogen-free injection containers.

The invention claimed is:

1. A compound of formula (I)

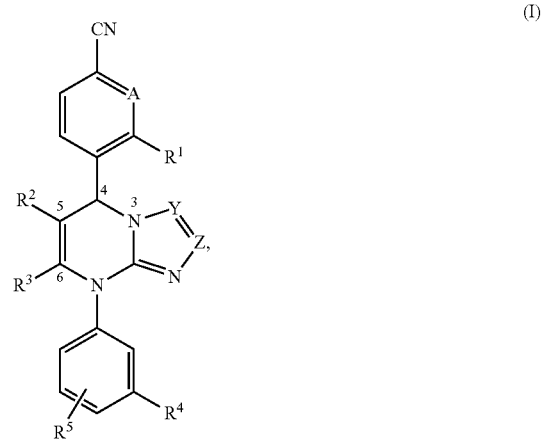

in which
A represents CH
Y represents C—$R^7$ or N in which
　$R^7$ represents hydrogen, ($C_1$-$C_6$)-alkyl, amino or a group of the formula —NH—C(=O)—$R^8$ or —NH—$SO_2$—$R^8$ in which
　　$R^8$ represents ($C_1$-$C_6$)-alkyl, ($C_3$-$C_6$)-cycloalkyl or phenyl,
　　　where ($C_1$-$C_6$)-alkyl may be substituted by hydroxyl, ($C_1$-$C_4$)-alkoxy, ($C_3$-$C_6$)-cycloalkyl or phenyl and up to three times by fluorine and where
the cycloalkyl groups mentioned may be substituted up to two times by identical or different substituents from the group consisting of ($C_1$-$C_4$)-alkyl and up to two times by fluorine
and
the phenyl groups mentioned may be substituted up to two times by identical or different substituents from the group consisting of fluorine, chlorine, cyano, ($C_1$-$C_4$)-alkyl, difluoromethyl, trifluoromethyl, ($C_1$-$C_4$)-alkoxy, difluoromethoxy and trifluoromethoxy, Z represents N $R^1$ represents hydrogen
or
represents a group of the formula —S(O)$_n$—$R^{20}$ in which
$R^{20}$ represents ($C_1$-$G_6$)-alkyl
and
N represents the number 0, 1 or 2, $R^2$ represents cyano or a group of the formula —C(=O)—$R^{21}$, —C(=O)—O—$R^{21}$ or —C(=O)—NH—$R^{21}$ in which
$R^{21}$ represents hydrogen, ($C_1$-$C_6$)-alkyl, ($C_3$-$C_6$)-alkenyl or ($C_3$-$C_6$)-cycloalkyl,
where ($C_1$-$C_6$)-alkyl and ($C_3$-$C_6$)-cycloalkyl for their part may be substituted up to two times by identical or different substituents from the group consisting of hydroxyl, ($C_1$-$C_4$)-alkoxy, hydroxycarbonyl, ($C_1$-$C_4$)-alkoxycarbonyl, amino, mono- and di-($C_1$-$C_4$)-alkylamino and in ($C_1$-$C_6$)-alkyl and ($C_3$-$C_6$)-cycloalkyl in each case one CH$_2$ group may be replaced by an oxygen atom provided this results in a chemically stable compound, $R^3$ represents methyl or ethyl
or
$R^2$ and $R^3$ are attached to one another and together form a fused group of the formula

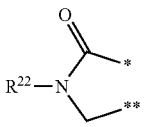

in which
* denotes the point of attachment to the 5-position, marked in formula (I), of the dihydropyrimidine ring
and
** denotes the point of attachment to the 6-position, marked in formula (I), of the dihydropyrimidine ring
and
$R^{22}$ represents hydrogen, ($C_1$-$C_6$)-alkyl or ($C_3$-$C_6$)-cycloalkyl,
where ($C_1$-$C_6$)-alkyl may be substituted by hydroxyl, ($C_1$-$C_4$)-alkoxy, aminocarbonyl, aminocarbonylamino, ($C_1$-$C_4$)-acylamino or ($C_3$-$C_6$)-cycloalkyl, $R^4$ represents nitro or trifluoromethyl
and
$R^5$ represents hydrogen, fluorine or chlorine,
or a salt thereof.

2. The compound of claim 1 in which
A represents CH,
Y represents C—$R^7$ or N,
in which
$R^7$ represents hydrogen, amino or a group of the formula —NH—C(=O)—$R^8$ or —NH—SO$_2$—$R^8$ in which
$R^8$ represents ($C_1$-$C_4$)-alkyl or ($C_3$-$C_6$)-cycloalkyl,
where ($C_1$-$C_4$)-alkyl may be substituted by hydroxyl, ($C_1$-$C_4$)-alkoxy or ($C_3$-$C_6$)-cycloalkyl and up to three times by fluorine
and
the cycloalkyl groups mentioned may be substituted up to two times by identical or different substituents from the group consisting of ($C_1$-$C_4$)-alkyl and up to two times by fluorine, Z represents N, $R^1$ represents hydrogen, or a group of the formula —SO$_2$—$R^{20}$ in which
$R^{20}$ represents ($C_1$-$C_4$)-alkyl $R^2$ represents cyano or a group of the formula —C(=O)—$R^{21}$ or —C(=O)—O—$R^{21}$ or C(=O)—NH—$R^{21}$ in which
$R^{21}$ represents hydrogen, methyl, ethyl or 2-hydroxyethyl, $R^3$ represents methyl,
$R^4$ represents trifluoromethyl
and
$R^5$ represents hydrogen,
or
$R^2$ and $R^3$ are attached to one another and together form a fused group of the formula

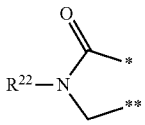

in which
* denotes the point of attachment to the 5-position, marked in formula (I), of the dihydropyrimidine ring
and
** denotes the point of attachment to the 6-position, marked in formula (I), of the dihydropyrimidine ring
and
$R^{22}$ represents hydrogen, ($C_1$-$C_6$)-alkyl or ($C_3$-$C_6$)-cycloalkyl, where ($C_1$-$C_6$)-alkyl may be substituted by hydroxyl, ($C_1$-$C_4$)-alkoxy;
or a salt thereof.

3. The compound of claim 1 in which
A represents CH,
Y represents C—$R^7$ or N,
in which
$R^7$ represents amino or a group of the formula —NH—C(=O)—$R^8$ in which
$R^8$ represents ($C_1$-$C_4$)-alkyl or ($C_3$-$C_6$)-cycloalkyl,
where ($C_1$-$C_4$)-alkyl may be substituted by hydroxyl, methoxy, ethoxy or ($C_3$-$C_6$)-cycloalkyl and up to three times by fluorine and
the cycloalkyl groups mentioned may be substituted up to two times by methyl and up to two times by fluorine, Z represents N, $R^1$ represents hydrogen, methyl sulfonyl or trifluoromethyl-sulfonyl, $R^2$ represents cyano, acetyl, ethoxycarbonyl, carboxyl, or aminocarbonyl $R^3$ represents methyl, $R^4$ represents trifluoromethyl and
R⁵ represents hydrogen,
or a salt thereof.

4. The compound of claim 1, wherein
A represents CH,
Y represents C—R⁷ or N,
whererein,
R⁷ represents amino or a group of the formula —NH—C(=O)—R⁸ in which
R⁸ represents (C₃-C₆)-cycloalkyl,
[where the cycloalkyl groups mentioned may be substituted up to two times by methyl and up to two times by fluorine,]
Z represents N,
R¹ represents hydrogen,
R² represents cyano, acetyl, ethoxycarbonyl, carboxyl, or aminocarbonyl,
R³ represents methyl,
or
R² and R³ are attached to one another and together form a fused group of the formula

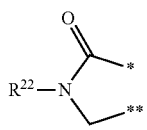

in which
* denotes the point of attachment to the 5-position, marked in formula (I), of the dihydropyrimidine ring
and
** denotes the point of attachment to the 6-position, marked in formula (I), of the dihydropyrimidine ring
and
R²² represents (C₁-C₆)-alkyl,
where (C1-C6)-alkyl is substituted by (C1-C4)-alkoxy,
R⁴ represents trifluoromethyl
and
R⁵ represents hydrogen,
or a salt thereof.

5. The compound of claim 1, selected from the group consisting of:

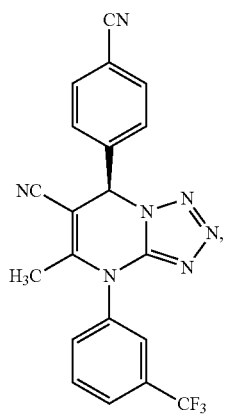

-continued

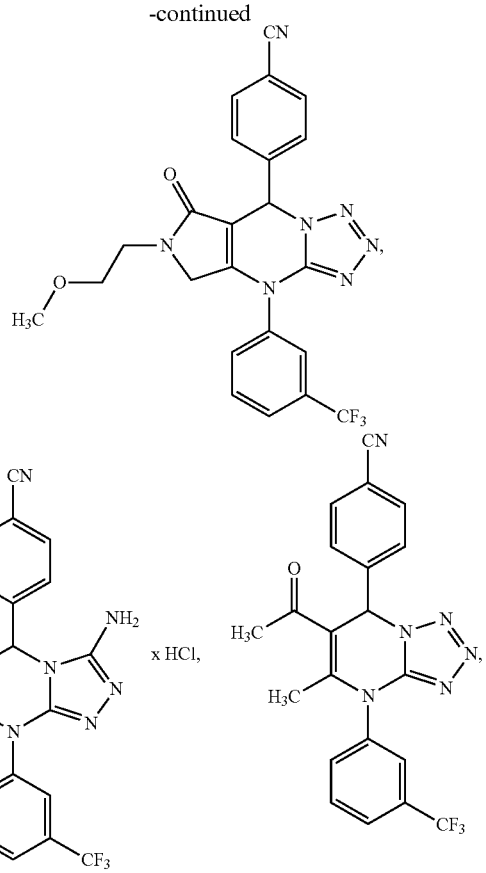

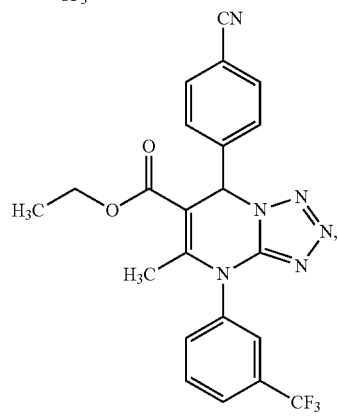

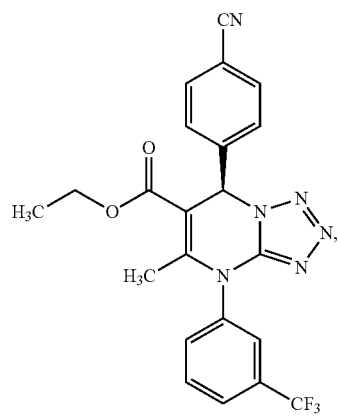

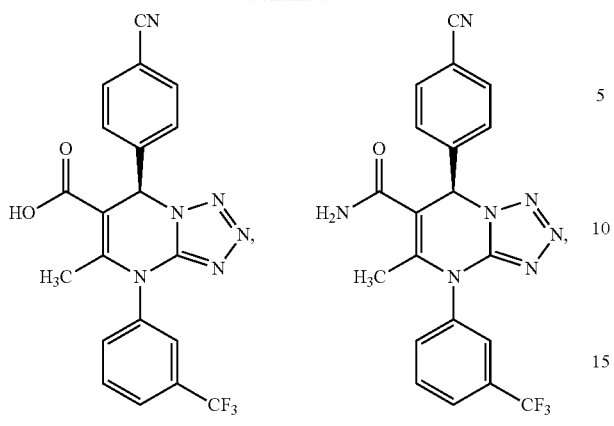

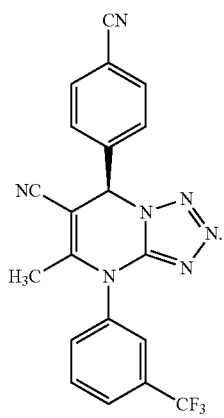

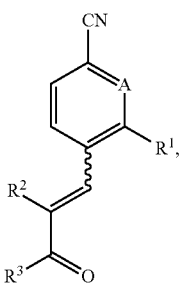

and

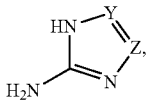

.

6. A compound of the formula:

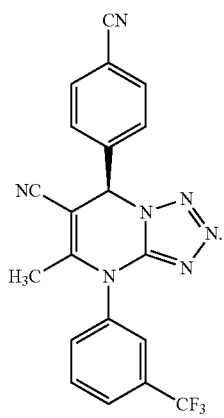

7. A pharmaceutical composition comprising a compound of claim 1 and at least one inert non-toxic pharmaceutically acceptable excipient.

8. The pharmaceutical composition of claim 7 further comprising at least one active compound selected from the group consisting of a kinase inhibitor, a stimulator and activator of soluble guanylate cyclase, a prostacyclin analog, an endothelin receptor antagonist, a phosphodiesterase inhibitor, a beta-adrenergic receptor agonist, an anticholinergic, and a glucocorticoid.

9. A process for preparing a compound of claim 1, comprising reacting a compound of formula (II)

(II)

in which A, R¹, R² and R³ each have the meanings given in claim 1, in the presence of a base with a compound of formula (III)

(III)

in which Y and Z have the meanings given in claim 1, to give an intermediate of formula (IV)

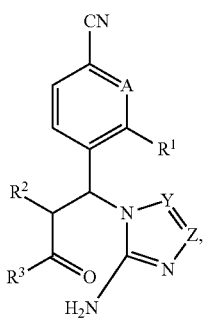

(IV)

in which A, Y, Z, $R^1$, $R^2$ and $R^3$ each have the meanings given above, cyclizing the intermediate of formula (IV) in situ or in a separate acid-catalyzed reaction step to give a compound of formula (V)

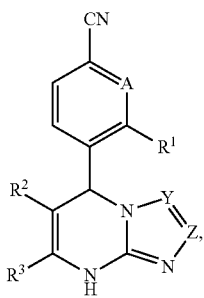

(V)

in which A, Y, Z, $R^1$, $R^2$ and $R^3$ each have the meanings given above, coupling the compound of formula (V) in the presence of a copper(II) catalyst and a base with a phenylboronic acid of formula (VI)

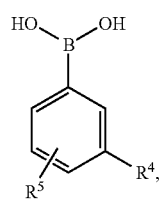

(VI)

in which $R^4$ and $R^5$ have the meanings given in claim 1, to give the compound of formula (I).

10. The process of claim 9, wherein more than one enantiomer or diastereomer of a compound of formula (I) is produced, the process further comprising a step of separating the enantiomers or diastereomers.

11. The process of claim 9, wherein the compound of formula (I) is converted with an appropriate (i) solvents and/or (ii) bases or acids into a salt thereof.

12. A method for the treatment of pulmonary arterial hypertension (PAH) and other forms of pulmonary hypertension (PH), of chronic-obstructive pulmonary diseases (COPD), of acute lung injury (ALI), of acute respiratory distress syndrome (ARDS), of bronchiectasis, of Bronchiolitis obliterans, of pulmonary emphysema, of alpha-1 antitrypsin deficiency (AATD) and of cystic fibrosis (CF) comprising administering to a human or animal in need thereof an effective amount of a compound of claim 1.

\* \* \* \* \*